(12) United States Patent
Blumstock et al.

(10) Patent No.: US 12,691,130 B2
(45) **Date of Patent: *Jul. 28, 2026**

(54) COMPOSITIONS AND METHODS FOR IMPROVING COGNITIVE FUNCTION

(71) Applicant: Diamond Therapeutics Inc., Toronto (CA)

(72) Inventors: Judith Blumstock, Toronto (CA); William James Tyler, Chelsea, AL (US)

(73) Assignee: Diamond Therapeutics Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/814,163

(22) Filed: Aug. 23, 2024

(65) Prior Publication Data

US 2026/0053831 A1 Feb. 26, 2026

Related U.S. Application Data

(63) Continuation of application No. 18/053,648, filed on Nov. 8, 2022, now abandoned, which is a
(Continued)

(51) Int. Cl.
*A61K 31/675* (2006.01)
*A61K 9/127* (2025.01)
(Continued)

(52) U.S. Cl.
CPC ............ *A61K 31/675* (2013.01); *A61K 9/127* (2013.01); *A61K 9/2009* (2013.01);
(Continued)

(58) Field of Classification Search
CPC .................................................... A61K 31/675
See application file for complete search history.

(56) References Cited

U.S. PATENT DOCUMENTS 3,183,172 A 5/1965 Roger et al.
3,192,111 A 6/1965 Albert et al.
(Continued)

FOREIGN PATENT DOCUMENTS

CA 3179290 A1 12/2021
CA 3133547 A1 4/2023
(Continued)

OTHER PUBLICATIONS

Md. K. Anwer et al. "Preparation, Evaluation and Bioavailability Studies of Eudragit Coated PLGA Nanoparticles for Sustained Release of Eluxadoline for the Treatment of Irritable Bowel Syndrome." Frontiers in Pharmacology, vol. 8, Article 844, Nov. 2017, pp. 1-11. (Year: 2017).*
(Continued)

*Primary Examiner* — Isaac Shomer
(74) *Attorney, Agent, or Firm* — WILSON SONSINI GOODRICH & ROSATI

(57) ABSTRACT

Disclosed herein are methods for managing disorders or conditions, or treating symptoms of disorders or conditions, comprising administering 5HT receptor agonists. The disorders may involve cognitive function and the methods of improving may comprise administering low doses of 5HT receptor agonists to subjects in need thereof. Improvement of the symptoms of a disorder involving cognitive function can be achieved where the disorders comprise mood, cognitive, anxiety, and depression disorders. Also disclosed herein are pharmaceutical compositions, formulations, and dosage forms of 5HT receptor agonists.

5 Claims, 6 Drawing Sheets

Related U.S. Application Data continuation of application No. 17/427,037, filed as application No. PCT/IB2020/000052 on Jan. 29, 2020, now abandoned.

(60) Provisional application No. 62/799,010, filed on Jan. 30, 2019, provisional application No. 62/798,998, filed on Jan. 30, 2019.

(51) Int. Cl.

| | |
|---|---|
| ***A61K 9/20*** | (2006.01) |
| ***A61K 9/51*** | (2006.01) |
| ***A61K 31/12*** | (2006.01) |
| ***A61K 31/137*** | (2006.01) |
| ***A61K 31/38*** | (2006.01) |
| ***A61K 31/4045*** | (2006.01) |
| ***A61K 31/4164*** | (2006.01) |
| ***A61K 31/422*** | (2006.01) |
| ***A61K 31/4439*** | (2006.01) |
| ***A61K 31/454*** | (2006.01) |
| ***A61K 31/48*** | (2006.01) |
| ***A61K 31/496*** | (2006.01) |
| ***A61K 31/5415*** | (2006.01) |
| ***A61K 31/5513*** | (2006.01) |
| ***A61K 31/554*** | (2006.01) |
| ***A61K 31/573*** | (2006.01) |
| ***A61K 31/685*** | (2006.01) |
| ***A61K 33/06*** | (2006.01) |
| ***A61K 36/258*** | (2006.01) |
| ***A61P 25/28*** | (2006.01) |

(52) U.S. Cl.

CPC .......... *A61K 9/2013* (2013.01); *A61K 9/2027* (2013.01); *A61K 9/5123* (2013.01); *A61K 9/5153* (2013.01); *A61K 31/12* (2013.01); *A61K 31/137* (2013.01); *A61K 31/38* (2013.01); *A61K 31/4045* (2013.01); *A61K 31/4164* (2013.01); *A61K 31/422* (2013.01); *A61K 31/4439* (2013.01); *A61K 31/454* (2013.01); *A61K 31/48* (2013.01); *A61K 31/496* (2013.01); *A61K 31/5415* (2013.01); *A61K 31/5513* (2013.01); *A61K 31/554* (2013.01); *A61K 31/573* (2013.01); *A61K 31/685* (2013.01); *A61K 33/06* (2013.01); *A61K 36/258* (2013.01); *A61P 25/28* (2018.01)

(56) References Cited

U.S. PATENT DOCUMENTS

| | | | | |
|---|---|---|---|---|
| 7,229,784 | B2 | 6/2007 | Holtzman et al. | |
| 10,064,856 | B2 | 9/2018 | Bosse et al. | |
| 10,519,175 | B2 | 12/2019 | Londesbrough et al. | |
| 10,596,378 | B2 | 3/2020 | Rustick | |
| 10,729,706 | B2 | 8/2020 | Kucuksen et al. | |
| 10,738,268 | B2 | 8/2020 | Leo | |
| 10,947,257 | B2 | 3/2021 | Londesbrough et al. | |
| 10,954,259 | B1 | 3/2021 | Londesbrough et al. | |
| 11,364,221 | B2 | 6/2022 | Liechti | |
| 11,717,517 | B2 | 8/2023 | Liechti et al. | |
| 11,766,445 | B2 | 9/2023 | LaRosa et al. | |
| 11,801,256 | B2 | 10/2023 | Liechti et al. | |
| 11,896,670 | B2 | 2/2024 | Trachsel et al. | |
| 11,963,946 | B2 | 4/2024 | Liechti | |
| 12,590,110 | B2 | 3/2026 | Blumstock et al. | |
| 2005/0261237 | A1* | 11/2005 | Boojamra ............ | C07F 9/6561 514/47 |
| 2007/0129385 | A1 | 6/2007 | Sharma et al. | |
| 2012/0108510 | A1 | 5/2012 | Young et al. | |
| 2012/0159656 | A1 | 6/2012 | Gerber et al. | |
| 2014/0052474 | A1 | 2/2014 | Madan et al. | |
| 2014/0114904 | A1 | 4/2014 | Choo et al. | |
| 2016/0138111 | A1 | 5/2016 | Knudsen | |
| 2016/0270656 | A1 | 9/2016 | Samec et al. | |
| 2017/0039344 | A1 | 2/2017 | Bitran et al. | |
| 2017/0216219 | A1* | 8/2017 | Dhar ................. | A61K 47/6937 |
| 2017/0283884 | A1 | 10/2017 | Knudsen | |
| 2018/0021326 | A1* | 1/2018 | Stamets ............ | A61K 31/4045 424/195.15 |
| 2018/0032698 | A1 | 2/2018 | Lau et al. | |
| 2018/0221396 | A1 | 8/2018 | Chadeayne | |
| 2019/0105313 | A1 | 4/2019 | Stamets | |
| 2019/0142851 | A1 | 5/2019 | Chadeayne | |
| 2019/0192498 | A1 | 6/2019 | Stamets | |
| 2019/0350949 | A1 | 11/2019 | Kucuksen et al. | |
| 2020/0085816 | A1 | 3/2020 | Raz | |
| 2020/0147038 | A1 | 5/2020 | Russ et al. | |
| 2020/0199161 | A1 | 6/2020 | Londesbrough et al. | |
| 2020/0215297 | A1 | 7/2020 | Rabin et al. | |
| 2020/0331939 | A1 | 10/2020 | Londesbrough et al. | |
| 2021/0033618 | A1 | 2/2021 | Innocenzi et al. | |
| 2021/0236523 | A1 | 8/2021 | Schindler et al. | |
| 2021/0267977 | A1 | 9/2021 | Liechti | |
| 2021/0315884 | A1 | 10/2021 | Liechti et al. | |
| 2021/0346341 | A1 | 11/2021 | Liechti | |
| 2021/0386704 | A1 | 12/2021 | Liechti et al. | |
| 2022/0040150 | A1 | 2/2022 | Liechti | |
| 2022/0096429 | A1 | 3/2022 | Liechti | |
| 2022/0096504 | A1 | 3/2022 | Blumstock et al. | |
| 2022/0151986 | A1 | 5/2022 | Liechti et al. | |
| 2022/0265582 | A1 | 8/2022 | Liechti | |
| 2022/0267252 | A1 | 8/2022 | Trachsel et al. | |
| 2022/0273628 | A1 | 9/2022 | Liechti et al. | |
| 2022/0280501 | A1 | 9/2022 | Liechti et al. | |
| 2022/0323405 | A1 | 10/2022 | Liechti | |
| 2022/0347169 | A1 | 11/2022 | Liechti et al. | |
| 2022/0387456 | A1 | 12/2022 | Liechti et al. | |
| 2023/0000799 | A1 | 1/2023 | Liechti | |
| 2023/0039395 | A1 | 2/2023 | Liechti et al. | |
| 2023/0066171 | A1 | 3/2023 | Trachsel et al. | |
| 2023/0091369 | A1 | 3/2023 | Trachsel et al. | |
| 2023/0113351 | A1* | 4/2023 | Blumstock .......... | A61K 31/496 514/77 |
| 2023/0150906 | A1 | 5/2023 | Liechti et al. | |
| 2023/0201160 | A1 | 6/2023 | Liechti | |
| 2023/0218568 | A1 | 7/2023 | Liechti | |
| 2023/0227398 | A1 | 7/2023 | Trachsel et al. | |
| 2023/0233688 | A1 | 7/2023 | Liechti et al. | |
| 2023/0248705 | A1 | 8/2023 | Gobbi et al. | |
| 2023/0285327 | A1 | 9/2023 | Trachsel et al. | |
| 2023/0285384 | A1 | 9/2023 | Liechti et al. | |
| 2023/0330085 | A1 | 10/2023 | Liechti et al. | |
| 2023/0355575 | A1 | 11/2023 | Liechti et al. | |
| 2023/0414583 | A1 | 12/2023 | Trachsel et al. | |
| 2024/0115710 | A1 | 4/2024 | Trachsel et al. | |
| 2024/0120053 | A1 | 4/2024 | Blumstock et al. | |
| 2024/0174594 | A1 | 5/2024 | Trachsel et al. | |
| 2024/0307345 | A1 | 9/2024 | Liechti | |
| 2024/0360161 | A1 | 10/2024 | Blumstock et al. | |
| 2025/0152565 | A1 | 5/2025 | Liechti et al. | |
| 2025/0171472 | A1 | 5/2025 | Blumstock et al. | |
| 2025/0176904 | A1 | 6/2025 | Blumstock et al. | |
| 2025/0182901 | A1 | 6/2025 | Tyler et al. | |
| 2025/0312309 | A1 | 10/2025 | Trachsel et al. | |

FOREIGN PATENT DOCUMENTS

| | | | | |
|---|---|---|---|---|
| CN | 108619214 A | | 10/2018 | |
| EP | 3675137 A1 | | 7/2020 | |
| JP | 2007525405 A | | 9/2007 | |
| WO | WO-2014140925 A2 | | 9/2014 | |
| WO | WO-2016138138 A1 | | 9/2016 | |
| WO | WO-2018067571 A2 | * | 4/2018 | ........... C12Q 1/6883 |
| WO | WO-2018135943 A1 | | 7/2018 | |
| WO | WO-2018148605 A1 | | 8/2018 | |
| WO | WO-2018195455 A1 | | 10/2018 | |
| WO | WO-2019079742 A1 | | 4/2019 | |
| WO | WO-2019161050 A1 | | 8/2019 | |

(56) References Cited

FOREIGN PATENT DOCUMENTS

| | | | | |
|---|---|---|---|---|
| WO | WO-2019180309 A1 | | 9/2019 | |
| WO | WO-2019246532 A1 | | 12/2019 | |
| WO | WO-2020041329 A1 | | 2/2020 | |
| WO | WO-2020157569 A1 | | 8/2020 | |
| WO | WO-2020181194 A1 | | 9/2020 | |
| WO | WO-2020212951 A1 | | 10/2020 | |
| WO | WO-2020212952 A1 | * | 10/2020 | ........... A61K 31/661 |
| WO | WO-2021003467 A1 | | 1/2021 | |
| WO | WO-2021019023 A1 | | 2/2021 | |
| WO | WO-2021030571 A1 | | 2/2021 | |
| WO | WO-2021059202 A1 | | 4/2021 | |
| WO | WO-2021072530 A1 | | 4/2021 | |
| WO | WO-2021108911 A1 | | 6/2021 | |
| WO | WO-2022016289 A1 | | 1/2022 | |
| WO | WO-2022023812 A1 | | 2/2022 | |
| WO | WO-2022023813 A1 | | 2/2022 | |
| WO | WO-2022189855 A1 | | 9/2022 | |
| WO | WO-2022243285 A1 | | 11/2022 | |
| WO | WO-2023078604 A1 | | 5/2023 | |
| WO | WO-2023170441 A1 | | 9/2023 | |
| WO | WO-2023227941 A1 | | 11/2023 | |
| WO | WO-2023237930 A1 | | 12/2023 | |
| ZA | 200002311 B | | 11/2001 | |

OTHER PUBLICATIONS

Kuypers, Kim PC, et al. Microdosing psychedelics: More questions than answers? An overview and suggestions for future research. Journal of Psychopharmacology 33(9):1039-1057 (2019). (Year: 2019).*

Sercl et al.: Clinical Experiences with Psilocybin (CY 39 Sandoz). Psychiat Neurol. 142:137-146 doi:10.1159/000131157 (English Google Machine Translation included) (1961) (Year: 1961).*

Felix Hasler, Ulrike Grimberg, Marco A. Benz, Theo Huber, and Franz X. Vollenweider. "Acute psychological and physiological effects of psilocybin in healthy humans: a double-blind, placebo-controlled dose-effect study." Psychopharmacology, vol. 172, 2004, pp. 145-156. (Year: 2004).*

Toronto Research Chemicals Inc. "Safety Data Sheet—Version 5.0." Psilocybin-d4. Preparation date: Aug. 21, 2013, pp. 1-6. (Year: 2013).*

Roland R. Griffiths et al. "Psilocybin produces substantial and sustained decreases in depression and anxiety in patients with life-threatening cancer: A randomized double-blind trial." Journal of Psychopharmacology, vol. 30(12), 2016, pp. 1181-1197. (Year: 2016).*

Petter Grahl Johnstad. "Powerful substances in tiny amounts: An interview study of psychedelic microdosing." Nordic Studies on Alcohol and Drugs, vol. 31(1), 2018, pp. 39-51. (Year: 2018).*

Roman Goff et al. "Determination of psilocybin and psilocin content in multiple Psilocybe cubensis mushroom strains using liquid chromatography—tandem mass spectrometry." Analytica Chimica Acta, vol. 1288, 2024, 342161, pp. 1-9. (Year: 2024).*

30 Day Microdosing Experiment. Thestonedyogagirl, Reddit, Aug. 22, 2019; [retrieved on Jul. 22, 2024]. Available at URL:https://www.reddit.com/r/microdosing/comments/ctkz2k/30_day_microdosing_experiment pp. 1-2.

Aghajanian et al.: Serotonin and Hallucinogens. Neuropsychopharmacology. 21(2 Suppl): 16S-23S (1999).

Akbari, Jafar et al. Development and evaluation of buccoadhesive propranolol hydrochloride tablet formulations: effect of fillers. Farmaco 59(2):155-161 (2004).

Anderson, Thomas, et al. Psychedelic microdosing benefits and challenges: an empirical codebook. Harm Reduction Journal 16(1):1-10 (2019).

Andersson et al.: Psychoactive substances as a last resort-a qualitative study of self-treatment of migraine and cluster headaches. Harm Reduct J. 2017 14(1):60, pp. 1-10 doi:10.1186/s12954-017-0186-6 (2017).

Ansel, Howard C. et al. Pharmaceutical Dosage Forms and Drug Delivery System, Seventh Edition. Lippincott Wiliams (1999).

Anxiety Disorders. Mayo Clinic, Nov. 14, 2018; [retrieved on Jul. 22, 2024]. Available at URL:https://web.archive.org/web/20181114083639/https:/www.mayoclinic.org/diseases-conditions/anxiety/symptoms-causes/syc-20350961 pp. 1-5.

Aronson: Plant Poisons and Traditional Medicines. Manson's Tropical Infectious Diseases (Twenty-Third Edition),pp. 1128-115010.e6 doi:10.1016/B978-0-7020-5101-2.00077-7 (2014).

Artusi, M. et al. Buccal delivery of thiocolchicoside: in vitro and in vivo permeation studies. International journal of pharmaceutics 250(1):203-213 (2003).

Berge, Stephen M. et al. Pharmaceutical Salts. Journal of Pharmaceutical Sciences 66(1):1-19 (1977).

Bershad et al.: Preliminary Report on the Effects of a Low Dose of LSD on Resting-State Amygdala Functional Connectivity. Biol Psychiatry Cogn Neurosci Neuroimaging 5(4):461-467 doi:10.1016/j.bpsc.2019.12.007 (2020).

Bogenschutz et al.: Psilocybin-assisted treatment for alcohol dependence: a proof-of-concept study. J Psychopharmacol 29(3):289-299 doi:10.1177/0269881114565144 (2015).

Boyd, medically reviewed by Miller: Lack of motivation: common causes, related health conditions, and more. pp. 1-4. URL:https://www.everlywell.com/blog/testosterone/lack-of-motivation-common-causes/ [retrieved online Mar. 15, 2023] (2019).

Buchborn et al.: Repeated lysergic acid diethylamide in an animal model of depression: Normalisation of learning behaviour and hippocampal serotonin 5-HT2 signalling. J Psychopharmacol. 28(6):545-552 doi:10.1177/0269881114531666 (2014).

Bundgaard, Hans. Chapter 5: Design and Application of Prodrugs. Textbook of Drug Design and Development 113-191 (1991).

Bundgaard, Hans. Design of Prodrugs. Elsevier 7(9):1-31 (1985).

Bundgaard, Hans. Means to Enhance Penetration: Prodrugs as a Means to Improve the Delivery of Peptide Drugs. Advanced Drug Delivery Review 8:1-38 (1992).

Cameron et al. Chronic, Intermittent Microdoses of the Psychedelic N, N-Dimethyltryptamine (DMT) Produce Positive Effects on Mood and Anxiety in Rodents. CS Chem Neurosci. 10(7):3261-3270 (2019).

Carhart-Harris et al.: Neural correlates of the psychedelic state as determined by fMRI studies with psilocybin. Proc Natl Acad Sci USA 109(6):2138-2143 doi:10.1073/pnas.1119598109 (2012).

Carhart-Harris et al.: Psilocybin with psychological support for treatment-resistant depression: an open-label feasibility study. Lancet Psychiatry 3: 619-627 (2016).

Carhart-Harris et al.: Psilocybin with psychological support for treatment-resistant depression: six-month follow-up. Psychopharmacology (Berl). 235(2):399-408 (2018).

Cavanna et al.: Microevidence for microdosing with psilocybin mushrooms: a double-blind placebo-controlled study of subjective effects, behavior, creativity, perception, cognition, and brain activity. bioRxiv pre-print, pp. 1-36 doi:10.1101/2021.11.30.470657 (2021).

Collett, John H, et al., Dosage Regimens. Aultons Pharmaceutics :7 Pages (2016).

Co-pending U.S. Appl. No. 18/764,635, inventors Blumstock; Judith et al., filed Jul. 5, 2024.

Co-pending U.S. Appl. No. 18/840,679, inventors Joel; Liederman et al., filed Aug. 22, 2024.

Daniel et al.: Clinical potential of psilocybin as a treatment for mental health conditions. Ment Health Clin [Internet]. 7(1): 24-28 (2017).

De Gregorio et al.: Hallucinogens in Mental Health: Preclinical and Clinical Studies on LSD, Psilocybin, MDMA, and Ketamine. J Neurosci. 41(5):891-900 doi:10.1523/JNEUROSCI.1659-20.2020 (2021).

De Gregorio et al.: Lysergic acid diethylamide (LSD) promotes social behavior through mTORC1 in the excitatory neurotransmission. PNAS USAS 118(5):e2020705118 doi:10.1073/pnas.2020705118 [1-9] (2021).

Desert Hope Treatment Center, Oral drug use: Signs, effects, & types. Retrieved from the Internet on Dec. 19, 2023.

(56) References Cited

OTHER PUBLICATIONS

Dolder et al.: Pharmacokinetics and Concentration-Effect Relationship of Oral LSD in Humans. Int J. Neuropsychopharmacol 19(1):pyv072, pp. 1-7 doi:10.1093/ijnp/pyv072 (2015).
Dos Santos et al.: Antidepressive, anxiolytic, and antiaddictive effects of ayahuasca, psilocybin and lysergic acid diethylamide (LSD): a systematic review of clinical trials published in the last 25 years. Ther Adv Psychopharmacol. 6(3):193-213 doi:10.1177/2045125316638008 (2016).
Engelhardt, Eliasz, et al. Neuropsychiatric symptoms in brain diseases. Dement. Neuropsychol. 14(3):324-328 (2020).
EP Application No. 20748736.4 Extended European Search Report dated Aug. 9, 2022.
EP21848825.2 Partial Supplemental European Search Report dated Aug. 14, 2024.
EP21848826.0 Extended European Search Report dated Jul. 15, 2024.
Erritzoe et al.: Effects of psilocybin therapy on personality structure. Acta Psychiatr Scand. 138(5):368-378 doi:10.1111/acps.12904 (2018).
Fadiman et al., Might microdosing psychedelics be safe and beneficial? An initial exploration. Journal of Psychoactive Drugs 51(2):118-122 (2019).
Family et al.: Safety, tolerability, pharmacokinetics, and pharmacodynamics of low dose lysergic acid diethylamide (LSD) in healthy older volunteers. Psychopharmacology (Berl). 237(3):841-853 doi:10.1007/s00213-019-05417-7 (2020).
Flanagan et al.: Psychedelics as anti-inflammatory agents. Int Rev Psychiatry. 30(4):363-375 doi:10.1080/09540261.2018.1481827 (2018).
GAD-7 Anxiety. Jun. 3, 2020; [retrieved on Jul. 22, 2024]. Available at URL: https://web.archive.org/web/20200603023323/https:/adaa.org/sites/default/files/GAD-7_Anxiety-updated_0.pdf p. 1.
Gennaro, Alfonso R. et al. Remington's Pharmaceutical Sciences, latest edition. Mack Publishing Co, Easton PA (1991).
Gennaro, Alfonso R. Remington: Practice of The Science and Pharmacy, 19th Edition. Mack Publishing Company (1995).
Greenan et al., Preparation and characterization of novel crystalline solvates and polymorphs of psilocybin and identification of solid forms suitable for clinical development. Feb. 13, 2020 (Retrieved from https://www.researchgate.net/publication/33923871029).
Griffiths et al.: Psilocybin Occasioned Mystical-Type Experiences: Immediate and Persisting Dose-Related Effects. Psychopharmacology 218(4):649-665 (2011).
Griffiths et al.: Psilocybin Produces Substantial And Sustained Decreases In Depression And Anxiety In Patients With Life-threatening Cancer: A Randomized Double-blind Trial. Journal of Psychopharmacology 30(12): 1181-1197 (2016).
Halberstadt et al. Behavioral Neurobiology of Psychedelic Drugs. Springer 36:161 (2018).
Hasler et al.: Determination of psilocin and 4-hydroxyindole-3-acetic acid in plasma by HPLC-ECD and pharmacokinetic profiles of oral and intravenous psilocybin in man. Pharm Acta Helv. 72(3):175-184 (1997).
Hibicke et al. Psychedelics, but Not Ketamine, Produce Persistent Antidepressant-like Effects in a Rodent Experimental System for the Study of Depression. ACS Chem Neurosci. 11(6):864-871 (2020).
Higgins et al.: Low Doses of Psilocybin and Ketamine Enhance Motivation and Attention in Poor Performing Rats: Evidence for an Antidepressant Property. Front Pharmacol. 12:640241:1-19 doi:10.3389/fphar.2021.640241 (2021).
Higgins, Guy A. et al. Rodent Test of Attention and Impulsivity: The 5-Choice Serial Reaction Time Task. Current Protocols Pharmacology 78:5.49.1-5.49.34 doi: 10.1002/cpph.27 (2017).
Hofmann, Albert et al. Psilocybin und Psilocin, zwei psychotrope Wirkstoffe aus mexikanischen Rauschpilzen. Helvetica Chimica Acta 42(5):1557-1572 (1959) (English Summary).
Hoover, John E. et al. Remington's Pharmaceutical Sciences. Mack Publishing Company 1-5 (1975).
Horsley, Rachel R., et al. Psilocin and ketamine microdosing: effects of subchronic intermittent microdoses in the elevated plus-maze in male Wistar rats. Behavioural Pharmacology 29(6):530-536 (2018).
Hutten et al., Motives and side-effects of microdosing with psychedelics among users. International Journal of Neuropsychopharmacology. 22(7):426-434 (2019).
Hutten et al., Self-rated effectiveness of microdosing with psychedelics for mental and physical health problems among microdosers. Frontiers in Psychiatry. 10:1-9 (2019).
IV LSD experience reports. ResidentPurple, Reddit, Dec. 4, 2018; [retrieved on Jul. 22, 2024]. Available at https://www.reddit.com/r/LSD/comments/a2yrk1/IV_lsd_experience_reports p. 1.
Jacques, Jean et al. Enantiomers, Racemates and Resolutions. John Wiley and Sons (1981).
Johns Hopkins Medicine, Obsessive-Compulsive Disorder. Retrieved from the Internet on Dec. 19, 2023: https://www.hopkinsmedicine.org/health/conditions-and-diseases/obsessivecompulsive-disorder.
Johnstad: Powerful substances in tiny amounts: An interview study of psychedelic microdosing. Nordisk Alkohol Nark 35(1):39-51 doi:10.1177/1455072517753339 (2018).
Kargbo, Robert B. et al. Direct Phosphorylation of Psilocin Enables Optimized cGMP Kilogram-Scale Manufacture of Psilocybin. ACS Omega 5(27):16959-16966 (2020).
Kryptonite: A Glorious New Year: LSD & MDMA (Ecstasy). Erowid, pp. 1-3 URL: https://erowid.org/experiences/exp.php?ID=58609 [retrieved online Jul. 29, 2022] (2009).
Lea et al., Perceived outcomes of psychedelic microdosing as self-managed therapies for mental and substance use disorders. Psychopharmacology 237:1521-1532 (2020).
Lea, Toby, et al. Microdosing psychedelics: Motivations, subjective effects and harm reduction. International Journal of Drug Policy 75:1-9 (2019).
Lee, Jaehwi. at al. Combined effect of oleic acid and polyethylene glycol 200 on buccal permeation of [D-ala2, D-leu5]enkephalin from a cubic phase of glyceryl monooleate. International Journal of Pharmaceutics 204(12):137-144 (2000).
Lieberman, Herbert A, and Leon Lachman. Pharmaceutical Dosage Forms: Tablets. Marcel Decker (1980).
Lindenblatt et al.: Quantitation of psilocin in human plasma by high-performance liquid chromatography and electrochemical detection: comparison of liquid-liquid extraction with automated on-line solid-phase extraction. J Chromatogr B Biomed Sci Appl. 709(2):255-263 doi:10.1016/s0378-4347(98)00067-x (1998).
Livescience, The weight of the world: Researchers weigh human population (2023) Retrieved from the Internet on Dec. 19, 2023: https://deserthopetreatment.com/addiction-guide/administration-methods/orally/.
Lopez-Gimenez et al.: Hallucinogens and Serotonin 5-HT 2A Receptor-Mediated Signaling Pathways. Curr Top Behav Neurosci. 36: 45-73 (2018).
Madsen et al.: Psychedelic effects of psilocybin correlate with serotonin 2A receptor occupancy and plasma psilocin levels. Neuropsychopharmacology 44(7):1328-1334 (2019).
Mahalingam, Ravichandran. et al. Transbuccal delivery of 5-aza-2-deoxycytidine: effects of drug concentration, buffer solution, and bile salts on permeation. AAPS PharmSciTech 8(3):E55 1-6 (2007).
Mental Health Conditions: Depression and Anxiety. Centers for Disease control and prevention, Web Archive, Dec. 31, 2019; [retrieved on Jul. 22, 2024]. Available at https://web.archive.org/web/20181231203416/https:/www.cdc.gov/tobacco/campaign/tips/diseases/depression-anxiety.html pp. 1-4.
Mertens et al., Therapeutic mechanisms of psilocybin: Changes in amygdala and prefrontal functional connectivity during emotional processing after psilocybin for treatment-resistant depression. Journal of Psychopharmacology 34(2):167-180 (2020).
Microdosing for Anxiety and Depression. Tetrisdroi, Erowid Experience Vaults, May 23, 2018; [retrieved on Jul. 22, 2024]. Available at URL:https://erowid.org/experiences/exp.php?ID=108178 pp. 1-2.
Moreno et al.: Safety, tolerability, and efficacy of psilocybin in 9 patients with obsessive-compulsive disorder. J Clin Psychiatry. 67(11):1735-1740 doi:10.4088/jcp.v67n1110 (2006).

(56) References Cited

OTHER PUBLICATIONS

Murray et al.: Low doses of LSD reduce broadband oscillatory power and modulate event-related potentials in healthy adults. Psychopharmacology (Berl) 239(6):1735-1747 doi:10.1007/s00213-021-05991-9 (2022).
Nagapudi et al.: Amorphous Active Pharmaceutical Ingredients in Preclinical Studies: Preparation, Characterization, and Formulation. Current Bioactive Compounds 400(4):213-224 doi:10.2174/157340708786847852 (2008).
Nichols, David E and Stewart Frescas. Improvements to the Synthesis of Psilocybin and a Facile Method for Preparing the O-Acetyl Prodrug of Psilocin. Synthesis 1999(6):935-938 (1999).
Nichols et al.: Serotonin Receptors. Chem. Rev. 108: 1614-1641 (2008).
Nicolazzo, Joseph A. et al. Modification of buccal drug delivery following pretreatment with skin penetration enhancers. Journal of pharmaceutical sciences 93(8):2054-2063 (2004).
Nielson et al.: The Psychedelic Debriefing in Alcohol Dependence Treatment: Illustrating Key Change Phenomena through Qualitative Content Analysis of Clinical Sessions. Front Pharmacol. 9(132):1-13 doi:10.3389/fphar.2018.00132 (2018).
Passie: The Science of Microdosing Psychedelics: Microdosing Other Psychedelics. The Psychedelic Press, Chapter 15, pp. 199-206 ISBN 978-0992808884 (2019).
Passie, Torsten, et al. The pharmacology of lysergic acid diethylamide: A review. CNS Neurosci. Ther. 14(4):295-314 (2008).
Patient Health Questionnaire (PHQ-9). Pfizer Inc, Jun. 19, 2018; [retrieved on Jul. 22, 2024]. Available at URL: https://web.archive.org/web/20180619082559/https:/med.stanford.edu/fastlab/research/imapp/msrs/_jcr_content/main/accordion/accordion_content3/download_256324296/file.res/PHQ9%20id%20date%2008.03.pdf pp. 1-2.
PCT/IB2020/000052 International Search Report and Written Opinion dated Jun. 4, 2020.
PCT/IB2021/000488 International Search Report and Written Opinion dated Dec. 6, 2021.
PCT/IB2021/000494 International Search Report and Written Opinion dated Nov. 24, 2021.
PCT/IB2022/000103 International Search Report and Written Opinion dated Jul. 4, 2022.
PCT/IB2022/000513 International Search Report and Written Opinion dated Jan. 27, 2023.
PCT/IB2023/000292 International Search Report and Written Opinion mailed on Oct. 17, 2023.
PCT/IB2023/000349 International Search Report and Written Opinion dated Oct. 26, 2023.
Polito, Vince, and Richard J Stevenson. A systematic study of microdosing psychedelics. PLoS one 14(2):e0211023, 1-26 (2019).
Prochazkova, Luisa, et al., Exploring the Effect of Microdosing Psychedelics on Creativity in an Open-label Natural Setting. Psychopharmacology 235(12):3401-3413 (2018).
Rijckevorsel: Cognitive problems related to epilepsy syndromes, especially malignant epilepsies. Seizure 15(4):227-234 doi:10.1016/j.seizure.2006.02.019 (2006).
Ross et al.: Rapid and sustained symptom reduction following psilocybin treatment for anxiety and depression in patients with life-threatening cancer: a randomized controlled trial. J Psychopharmacol 30(12):1165-1180 doi:10.1177/0269881116675512 (2016).
Sakloth et al.: Effects of acute and repeated treatment with serotonin 5-HT2A receptor agonist hallucinogens on intracranial self-stimulation in rats. Exp Clin Psychopharmacol. 27(3):215-226 doi:10.1037/pha0000253 (2019).
Sandri, Giuseppina et al. Mucoadhesive and penetration enhancement properties of three grades of hyaluronic acid using porcine buccal and vaginal tissue, Caco-2 cell lines, and rat jejunum. Journal of Pharmacy and Pharmacology 56(9):1083-1090 (2004).
Schenberg: Psychedelic-Assisted Psychotherapy: A Paradigm Shift in Psychiatric Research and Development. Front Pharmacol. 9(733):1-11 doi:10.3389/fphar.2018.00733 (2018).
Schott Lab 960 Conductivity Bench Laoratory Meter. CV Gihon Juma Sentosa, Jul. 18, 2024; [retrieved on Jul. 19, 2024]. Available at URL:https://en.gihonjumasentosa.com/product/schott-lab-960-conductivity-bench-laoratory-meter-p718127.aspx pp. 1-4.
Senel, Sevda, and Atilla Hincal et al. Drug permeation enhancement via buccal route: possibilities and limitations. Journal of Controlled Release 72(1-3):133-144 (2001).
Sercl et al.: Clinical Experiences with Psilocybin (CY 39 Sandoz). Psychiat Neurol. 142:137-146 doi:10.1159/000131157 (English Google Machine Translation included) (1961).
Sessa et al.: Underground MDMA-, LSD- and 2-CB-assisted individual and group psychotherapy in Zurich: Outcomes, implications and commentary. Drug Science, Policy and Law 2(0):1-8 (2015).
Sherwood, Alexander M. et al. An Improved, Practical, and Scalable Five-Step Synthesis of Psilocybin. Synthesis 52(5):688-694 (2020).
Shirota et al., Concise Large-Scale Synthesis of Psilocin and Psilocybin, Principal Hallucinogenic Constituents of "Magic Mushroom". J. Nat. Prod. 66(6):885-887 (2003).
Stahl, P Heinrich, and Camille G. Wermuth. Handbook of Pharmaceutical Salts: Properties, Selection, and Use. Verlag Helvetica Chimica Acta and Wiley-VCH (2002).
Starokadomskyy P.L. and Dubey I.Ya. New absorption promoter for the buccal delivery: preparation and characterization of lysalbinic acid. International Journal of Pharmacy 308(1-2):149-154 (2006).
Sudhakar, Yajaman et al. Buccal bioadhesive drug delivery—A promising option for orally less efficient drugs. Journal of Controlled Release 114(1):15-40 (2006).
The Freelance Writer Using LSD for Depression. The Cut, Web Archive, Oct. 24, 2017; [retrieved on Jul. 22, 2024]. Available at URL:https://www.thecut.com/2017/10/microdosing-lsd-depression-coping-diaries.html pp. 1-3.
Timmermann et al.: Neural correlates of the DMT experience assessed with multivariate EEG. Sci Rep. 9(1):16324:1-13 doi:10.1038/s41598-019-51974-4 (2019).
U.S. Appl. No. 17/427,037 Notification of Third-Party Pre-Issuance Submission mailed Jul. 22, 2022.
U.S. Appl. No. 18/053,648 Final Office Action dated Apr. 24, 2023.
U.S. Appl. No. 18/053,648 Non-Final Office Action dated Mar. 7, 2023.
U.S. Appl. No. 62/574,307, filed Oct. 19, 2017.
U.S. Appl. No. 18/053,648 Office Action dated Apr. 30, 2024.
U.S. Appl. No. 18/053,648 Office Action dated Jan. 9, 2024.
U.S. Appl. No. 18/102,268 Notice of Third-party Submission dated Jan. 22, 2024.
U.S. Appl. No. 18/764,635 Restriction Requirement dated Sep. 26, 2024.
Usona Institute, A randomized, double-blind, support-of-concept phase 2 study of single-dose psilocybin for major depressive disorder (MDD). Study record first posted Mar. 5, 2019. https://clinicaltrials.gov/study/NCT03866174.
Vaupel et al.: The inhibition of food intake in the dog by LDS, mescaline, psilocin, d-amphetamine and phenylisopropylamine derivatives. Life Sci. 24(26):2427-2431 doi:10.1016/0024-3205(79)90451-x (1979).
Voineskos et al., Management of treatment-resistant depression: Challenges and strategies. Neuropsychiatric Disease and Treatment 16:221-234 (2020).
Widder, Kenneth J, and Ralph Green. Method in Enzymology. Academic Press 112:309-396 (1985).
Xiuting et al.: Hallucinogenic Mushrooms: From God's Messenger to Human Medicine. Nanfang Daily, Edition 013, Medicine & Public Health, Newsweek Tech Visibility, pp. 1-3. China Academic Journal Electronic Publishing House. China Academic Journal Electronic Publishing House. [URL: http://www.cnki.net/KCMS/detail/detail.aspx?dbcode=CCND&dbname=CCNDLAST2014&filename=NFRB201409270130&uniplatform=OVERSEA&v=wDuBzelq46BeFwRM2MloyS-iDtu6ApnMcntTt8Tz2x-ebUksdocz3MTUOulTqKDNwEt9dTBajuo%3d] (Sep. 27, 2014).
Yaden et al., The Subjective Effects of Psychedelics are Necessary for Their Enduring Therapeutic Effects. ACS Pharmacol. Transl. Sci. 4(2): 568-572 (2021).
Psychedelic Science Review. Sandoz Parmaceutical Begins Selling Psilocybin Under the Trade Name Indocybin (2025) [retrieved on

(56) References Cited

OTHER PUBLICATIONS

Feb. 27, 2025]. Available at URL: https://psychedelicreview.com/event/sandoz-parmaceutical-manufactures-indocybin/ pp. 1-4.
Stielow, Marlena, et al. The Bioavailability of Drugs—The Current State of Knowledge. Molecules 28:8038 (2023) (19 pages).
Banerjee, Emili, et al. Does serotonin deficit mediate susceptibility to ADHD? Neurochemistry International 82:52-68 (2015).
ClinicalTrials.gov. A Study of Psilocybin for Major Depressive Disorder (MDD). ClinicalTrials.gov Identifier: NCT03866174. First Posted Mar. 7, 2019. 11 pages. Search results downloaded on Jan. 8, 2024 from the Internet at URL: https://clinicaltrials.gov/study/NCT03866174.
Co-pending U.S. Appl. No. 18/812,812, inventors Blumstock; Judith et al., filed Aug. 22, 2024.
Co-pending U.S. Appl. No. 18/812,843, inventors Blumstock; Judith et al., filed Aug. 22, 2024.
Co-pending U.S. Appl. No. 18/812,847, inventors Blumstock; Judith et al., filed Aug. 22, 2024.
Co-pending U.S. Appl. No. 18/813,959, inventors Blumstock; Judith et al., filed Aug. 23, 2024.
Co-pending U.S. Appl. No. 18/814,172, inventors Blumstock; Judith et al., filed Aug. 23, 2024.
Co-pending U.S. Appl. No. 18/814,182, inventors Blumstock; Judith et al., filed Aug. 23, 2024.
Co-pending U.S. Appl. No. 18/841,530, inventors Blumstock; Judith et al., filed Aug. 26, 2024.
Co-pending U.S. Appl. No. 19/030,518, inventors Blumstock; Judith et al., filed Jan. 17, 2025.
EP21848825.2 Extended European Search Report dated Nov. 6, 2024.
EP22766444.8 Extended European Search Report dated Dec. 23, 2024.
Greenan, Catherine, et al. Preparation and characterization of novel crystalline solvates and polymorphs of psilocybin and identification of solid forms suitable for clinical development. Published Feb. 13, 2020. DOI: 10.13140/RG.2.2.32357.14560, pp. 1-29.
Johns Hopkins Medicine, Health. Obsessive-Compulsive Disorder. Retrieved from the Internet on Dec. 19, 2023 (Year: 2023): https://www.hopkinsmedicine.org/health/conditions-and-diseases/obsessivecompulsive-disorder-ocd pp. 1-5.
Kuypers, Kim PC, et al. Microdosing psychedelics: More questions than answers? An overview and suggestions for future research. Journal of Psychopharmacology 33(9):1039-1057 (2019).
Rettner, Rachael. The Weight of the World: Researchers Weigh Human Population. Live Science, Future US Inc., New York, NY. Published May 30, 2013 (Year: 2023). Retrieved from the Internet on Dec. 19, 2023 at URL: https://www.livescience.com/36470-human-population-weight.html pp. 1-9. (Retrieved on Jan. 6, 2025. Retrieved from Internet (Wayback Machine): https://web.archive.org/web/20231004012405/https://www.livescience.com/36470-human-population-weight.html).
Rossa, Marley. Titrating your trip: Microdosing and mental health. Neuwrite San Diego, Apr. 12, 2018. Retrieved from the Internet: URL: https://neuwritesd.org/2018/04/12/titrating-your-trip-microdosing-and-mental-health/.
Sandison, R. A., et al. The Therapeutic Value of Lysergic Acid Diethylamide in Mental Illness. Journal of Mental Science 100(419):491-507 (1954).
Stevanovic, D. Quality Of Life Enjoyment And Satisfaction Questionnaire-Short Form For Quality Of Life Assessments In Clinical Practice: A Psychometric Study. Journal of Psychiatric and Mental Health Nursing 18(8):744-750 (2011).
U.S. Appl. No. 18/764,635 Office Action dated Dec. 16, 2024.
U.S. Appl. No. 18/812,847 Office Action dated Jan. 16, 2025.
U.S. Appl. No. 18/813,959 Office Action dated Jan. 16, 2025.
U.S. Serial No. 18/814, 172 Office Action dated Jan. 3, 2025.
U.S. Serial No. 18/814,182 Restriction Requirement dated Dec. 27, 2024.
Webster, Adrienne, LAC. Oral Drug Use: Signs, Effects & Types. Desert Hope Treatment Center. Updated: Nov. 14, 2022 (Year: 2023). Retrieved from the Internet on Dec. 19, 2023 at URL: https://deserthopetreatment.com/addiction-guide/administration-methods/orally/ pp. 1-5. (Retrieved on Jan. 6, 2025. Retrieved from Internet (Wayback Machine): https://web.archive.org/web/20230928004820/https://deserthopetreatment.com/addiction-guide/administration-methods/orally/).
Weston, Neil M., et al. Historic psychedelic drug trials and the treatment of anxiety disorders. Depression and Anxiety 37(12):1261-1279 (2020).
Catlow, Briony J. et al. Effects of psilocybin on hippocampal neurogenesis and extinction of trace fear conditioning. Experimental Brain Research 228(4):481-491 (2013).
Gasser, Peter. et al. LSD-assisted psychotherapy for anxiety associated with a life-threatening disease: A qualitative study of acute and sustained subjective effects. Journal of Psychopharmacology 29(1):57-68 (2015).
Hasler et al. Acute psychological and physiological effects of psilocybin in healthy humans: a double-blind, placebo-controlled dose-effect study. Psychopharmacology (Berl). Mar. 2004;172(2):145-56. doi: 10.1007/s00213-003-1640-6. Epub Nov. 13, 2003.
Sekssaoui, Mehdi, et al. Antidepressant-like effects of psychedelics in a chronic despair mouse model: is the 5-HT2A receptor the unique player? Neuropsychopharmacology 49:747-756 (2024).
U.S. Appl. No. 18/102,296 Office Action dated Jul. 3, 2025.
U.S. Appl. No. 18/764,635 Office Action dated Apr. 9, 2025.
U.S. Appl. No. 18/813,959 Office Action dated May 29, 2025.
U.S. Appl. No. 18/814,172 Office Action dated May 1, 2025.
U.S. Appl. No. 18/814,182 Office Action dated Mar. 31, 2025.
U.S. Appl. No. 19/030,518 Office Action dated Aug. 26, 2025.
Yu, Lian. Amorphous pharmaceutical solids: preparation, characterization and stabilization. Advanced Drug Delivery Reviews 48(1):27-42 (2001).
Becker, Stephen P. Cognitive disengagement syndrome: A construct at the crossroads. The American psychologist 80(5):812-834 (2025).
Dittrich, A. The Standardized Psychometric Assessment of Altered States of Consciousness (ASCs) in Humans. Pharmacopsychiatry 31 (Suppl. 2):80-84 (1998).
Ferhaha, Gagan et al. Motivational deficits in major depressive disorder: Cross-sectional and longitudinal relationships with functional impairment and subjective well-being. Comprehensive psychiatry 66:31-38 (2016).
Folk, Jim. Lack of Motivation and Anxiety. anxietycentre, Nov. 4, 2025; Available at URL: https:/www.anxietycentre.com/anxiety-disorders/symptoms/lack-of-motivation/ pp. 1-15.
Gennaro, Alfonso R. Remington: The Science And Practice of Pharmacy, 19th Edition. Mack Publishing Company :1-6 (1995).
Griffiths, Roland R., et al. Psilocybin occasioned mystical-type experiences: immediate and persisting dose-related effects. Psychopharmacology (Berl). 218(4):649-665 (2011). doi: 10.1007/s00213-011-2358-5.
Halberstadt, Adam L., et al. Behavioral Neurobiology of Psychedelic Drugs, vol. 36, Springer (434 pages) (2018).
Higgins, Guy A., et al. Low Doses of Psilocybin and Ketamine Enhance Motivation and Attention in Poor Performing Rats: Evidence for an Antidepressant Property. Frontiers in Pharmacology 12(640241) (2021), 19 pages.
Howlett Jr and Stein MB. Chapter 16: Post-Traumatic Stress Disorder. Translational Research in Traumatic Brain Injury :1-8 (2016).
Nall, Rachel. Tips for finding motivation with depression. MedicalNewsToday, Aug. 12, 2019; [retrieved on Dec. 4, 2025]. Available at URL: https://www.medicalnewstoday.com/articles/315862 pp. 1-16.
Palfreyman, Michael G. et al. Modification of natural tryptamines for the treatment of neuropsychiatric diseases. Journal of Psychopharmacology 39(12):1338-1350 (2025).
Pedzich, Bazej D. et al. Psychedelic-Induced Serotonin 2A Receptor Downregulation Does Not Predict Swim Stress Coping in Mice. International journal of molecular sciences 23(23):15284 1-17 (2022).
Spiegel, David R. et al. Disorders of diminished motivation: what they are, and how to treat them. Curr Psychiatry 17(1):11-18, 20 (2018).

(56) References Cited

OTHER PUBLICATIONS

Studerus, Erich, et al. Acute, subacute and long-term subjective effects of psilocybin in healthy humans: A pooled analysis of experimental studies. J. Psychophamracol. 25:1434-1452 (2011).
Studerus, Erich, et al. Psychometric Evaluation of the Altered States of Consciousness Rating Scale (OAV). PLoS One 5(8):312412 (19 pages) (2010).
Tsujikawa, Kenji et al. Morphological and chemical analysis of magic mushrooms in Japan. Forensic science international 138(1-3):85-90 (2003).
Volkow, N D. et al. Motivation deficit in ADHD is associated with dysfunction of the dopamine reward pathway. Molecular psychiatry 16(11):1147-1154 (2011).
Weast, Robert C., Ph.D., et al., CRC Handbook of Chemistry and Physics, 70th Edition, 1989-1990, po. 8-228 (Year: 1989).
EP23811237.9 Extended European Search Report dated Apr. 13, 2026.
Haijen, Eline C. H. M., et al. Predicting Responses to Psychedelics: A Prospective Study. Frontiers in Pharmacology 9:1-20 (2018).
Hancock, B C, and M Parksl. What is the True Solubility Advantage for Amorphous Pharmaceuticals? Pharmaceutical. Research 17(4):397-404 (2000).
Studerus, Erich, et al. Prediction of Psilocybin Response in Healthy Volunteers. PLOS ONE 7(2):e30800, 12 pages (2012).

* cited by examiner

COMPOSITIONS AND METHODS FOR IMPROVING COGNITIVE FUNCTION

BACKGROUND

The serotonin (5HT) receptors are a group of G protein-coupled receptors (GPCRs) and ligand-gated ion channels found in the central and peripheral nervous systems. Activation of 5HT receptors can substantially influence brain function.

Many people worldwide are afflicted with psychological or mood disorders, such as depression, anxiety, compulsion, and post-traumatic stress disorders, among others. Many of these conditions are believed to involve a person's serotonin system, including interactions between (A) the neurotransmitter serotonin and (B) several different subtypes of serotonin neurotransmitter receptors found in the human body.

A variety of compositions are known to modulate activity at the serotonin receptors. A number of pharmaceuticals (antidepressants, serotonin reuptake inhibitors, selective serotonin reuptake inhibitors, etc.) have become commercially available. Many leading commercial pharmaceutical products for treating mood disorders (such as depression, obsessive-compulsive disorder, and/or anxiety disorders) target serotonin pathways.

However, despite their popularity and commercial success, these pharmaceutical products are characterized by their long onset times, severe side-effects, and poor efficacy. In many cases, these drugs are harmful to the user. For example, many people taking prescription drugs targeting serotonin report feeling suicidal thoughts, sexual dysfunction, fatigue, elevated blood pressure, blurred vision, abnormal heart rate, nausea, and weight gain.

Psilocybin (also known as 4-phosphoryloxy-N,N-dimethyltryptamine or [3-(2-trimethylaminoethyl)-1H-indol-4-yl] dihydrogen phosphate) is considered to be the most abundant psychoactive compound within a "magic mushroom." Psilocybin has also been tested for its potential in developing prescription drugs to treat drug dependence, anxiety and mood disorders. However, therapeutic applications of psilocybin to date are tied with its adverse side effects, including hallucinations, panic attacks, psychosis, nausea, vomiting, muscle weakness, and lack of coordination. Accordingly, there is a need to develop pharmaceutical compositions of psilocybin for treating disorders associated with 5HT receptors without the adverse side effects.

SUMMARY

Provided herein in certain embodiments are methods and compositions for the treatment of psychological, cognitive, behavioral, and/or mood disorders. In some embodiments, a disorder described herein is treated by administration of a therapeutically effective amount of a agent described herein, such as a 5HT agonist (such as an active 5HT agonist itself (e.g., psilocin), or a salt, solvate, metabolite, derivative, or prodrug thereof (e.g., psilocybin)). In certain embodiments, such agents are administered at (or are present in a composition provided herein in) an amount or level high enough to provide a therapeutic effect, e.g., but high enough to avoid an adverse effect (e.g., hallucinogenic or other adverse effect, such as panic attacks, psychosis, nausea, vomiting, muscle weakness, or lack of coordination) (e.g., a low dose, therapeutically effective amount). In certain instances, such low dose therapeutics (and/or compositions or methods provided herein) provide improved motivation, attention, accuracy, speed of response, perseveration, and/or cognitive engagement. In some embodiments such low dose therapeutics (and/or compositions or methods provided herein) are used in the treatment of behavioral and/or cognitive disorders, such as where motivation, attention, accuracy, speed of response, perseverance, and/or cognitive engagement play a role. In certain embodiments, compositions provided herein are useful in or used in the treatment depression, anxiety, apathy and/or low motivation, attention disorders, disorders of executive function and/or cognitive engagement, obsessive compulsive disorder, and/or neurocognitive disorders.

Provided herein in some embodiments is a method for treating or managing a mental, a behavioral, or a neuropsychiatric condition, or, the symptoms thereof, in an individual in need thereof, comprising administering to the individual a (e.g., therapeutically) effective amount of one or more modulator of an a-amino-3-hydroxy-5-methyl-5-isoxazole-propionic acid (AMPA) receptor and a 5-hydroxytryptamine (e.g., 5-hydroxytryptamine 2A (5-HT2A)) receptor (e.g., lysergic acid (LSD)), or a pharmaceutically acceptable salt, solvate, metabolite, derivative, or prodrug thereof (e.g., for an extended period of time (e.g., for repeating days)).

Also provided herein in some embodiments is a method of managing a neurological condition or one or more symptoms thereof in a subject in need thereof, comprising administering to the subject a pharmaceutical composition comprising:

a) a therapeutically effective amount of one or more 5HT receptor agonist (e.g., psilocin) or a pharmaceutically acceptable salt, solvate, metabolite, derivative, or prodrug thereof (e.g., psilocybin); and
b) a pharmaceutically acceptable excipient.

In some embodiments, the therapeutically effective amount of the 5HT receptor agonist or a pharmaceutically acceptable salt, solvate, metabolite, derivative, or prodrug thereof is provided to the subject in need thereof in an amount insufficient to provide an adverse side effect, such as hallucinogenic experience.

Also provided herein is a method of treating the symptoms of a neurological condition in a subject suffering from or susceptible to the neurological condition, comprising administering to the subject a pharmaceutical composition comprising:

a) a therapeutically effective amount of one or more 5HT receptor agonist (e.g., psilocin) or a pharmaceutically acceptable salt, solvate, metabolite, derivative, or prodrug thereof (e.g., psilocybin); and
b) a pharmaceutically acceptable excipient.

In specific embodiments, the therapeutically effective amount of the 5HT receptor agonist or a pharmaceutically acceptable salt, solvate, metabolite, derivative, or prodrug thereof is provided to the subject in need thereof in an amount insufficient to provide an adverse side effect, such as hallucinogenic experience.

In some embodiments, the 5HT receptor agonist or a pharmaceutically acceptable salt, solvate, metabolite, derivative, or prodrug thereof is present in an amount of from about 0.1 mg to about 50 mg (e.g. about 0.1 mg to about 10 mg, about 0.2 mg to about 5 mg, about 10 mg to about 50 mg, or the like).

In some embodiments, the 5HT receptor agonist or a pharmaceutically acceptable salt, solvate, metabolite, derivative, or prodrug thereof is present in an amount of from about 0.1 mg to about 2 mg.

In some embodiments, the 5HT receptor agonist or a pharmaceutically acceptable salt, solvate, metabolite, derivative, or prodrug thereof is present in an amount of from about 1 mg to about 15 mg.

In some embodiments, the pharmaceutical composition is a low-dose pharmaceutical composition.

In some embodiments, the pharmaceutical composition comprises a controlled release component.

In some embodiments, the pharmaceutical composition comprises a controlled release component and an immediate release component.

In some embodiments, the therapeutically effective amount of 5HT receptor agonist (e.g., psilocin) or a pharmaceutically acceptable salt, solvate, metabolite, derivative, or prodrug thereof (e.g., psilocybin) is provided to a subject in need thereof in an amount and/or formulation insufficient to provide a maximum plasma concentration ($C_{max}$) of (e.g. active form of the) 5HT receptor agonist (e.g., psilocin) or a pharmaceutically acceptable salt, solvate, metabolite, derivative, or prodrug thereof of 6 ng/ml or more.

In some embodiments, the therapeutically effective amount of 5HT receptor agonist or a pharmaceutically acceptable salt, solvate, metabolite, derivative, or prodrug (e.g., psilocybin) thereof is provided to a subject in need thereof in an amount and/or formulation to provide a maximum plasma concentration ($C_{max}$) of (e.g. active form of the) 5HT receptor agonist (e.g., psilocin) or a pharmaceutically acceptable salt, solvate, metabolite, derivative, or prodrug thereof of about 0.1 ng/ml or more and less than 6 ng/mL (e.g. at least 0.5 ng/ml and less than 6 ng/ml, about 1 ng/mL to about 5.5 ng/mL, about 2 ng/mL to about 5 ng/ml, or the like).

In some embodiments, the therapeutically effective amount of 5HT receptor agonist (e.g., psilocin) or a pharmaceutically acceptable salt, solvate, metabolite, derivative, or prodrug thereof is provided to a subject in need thereof in an amount and/or formulation to provide a plasma concentration of (e.g. active form of the) 5HT receptor agonist (e.g., psilocin) or a pharmaceutically acceptable salt, solvate, metabolite, derivative, or prodrug thereof of at least 0.1 ng/mL (e.g. at least 0.2 ng/ml, at least 0.3 ng/ml, at least 0.5 ng/mL, or the like) after at least 6 hours (e.g. at least 12 hours, at least 24 hours, at least 36 hours, at least 48 hours, at least 72 hours, at least 96 hours, at least 120 hours, at least 144 hours, or the like).

In some embodiments, the 5HT receptor agonist is a 5HT2 receptor agonist. In some embodiments, the 5HT receptor agonist is psilocybin or a pharmaceutically acceptable salt, solvate, metabolite, derivative, or prodrug thereof.

Also disclosed herein is a pharmaceutical composition comprising:

a) a therapeutically effective amount of one or more 5HT receptor agonist (e.g., psilocin) or a pharmaceutically acceptable salt, solvate, metabolite, derivative, or prodrug thereof (e.g., psilocybin),
b) a pharmaceutically acceptable excipient, and
c) (e.g., optionally) one or more agents selected from the group consisting of surfactants, preservatives, flavoring agents, sweetening agents, and antifoaming agents.

Also disclosed herein is a pharmaceutical composition comprising:

a) a therapeutically effective amount of one or more 5HT receptor agonist (e.g., psilocin) or a pharmaceutically acceptable salt, solvate, metabolite, derivative, or prodrug thereof (e.g., psilocybin),
b) a pharmaceutically acceptable excipient, and
c) (e.g., optionally) one or more agents selected from the group consisting of surfactants, preservatives, flavoring agents, sweetening agents, and antifoaming agents;

In some embodiments, a pharmaceutical composition provided herein is a low-dose pharmaceutical composition. In some embodiments, following administration to an individual in need thereof, a pharmaceutical composition provided herein provides a maximum plasma concentration ($C_{max}$) of the 5HT receptor agonist (e.g., psilocin) (or a pharmaceutically acceptable salt, solvate, metabolite, derivative, or prodrug (e.g., psilocybin) thereof) of less than 6 ng/ml (e.g., the active form of the 5HT receptor agonist, regardless of the form administered) in the individual in need thereof. In some embodiments, the 5HT receptor agonist is psilocin or a pharmaceutically acceptable salt, solvate, metabolite, derivative, or prodrug thereof. In some embodiments, the 5HT receptor agonist is psilocybin or a pharmaceutically acceptable salt, solvate, metabolite, derivative, or prodrug thereof.

Also disclosed herein is a pharmaceutical composition comprising an oral dosage form, the oral dosage form comprising an immediate-release top layer and a controlled release core. In some embodiments, the immediate-release layer comprising (i) one or more 5HT receptor agonist or a pharmaceutically acceptable salt, solvate, metabolite, derivative, or prodrug thereof and (ii) one or more second agent. In some embodiments, the one or more second agent being a stimulant, an antihistamine, an antiemetic, an antidepressant, an anti-inflammatory, a growth factor, a lithium compound, resveratrol, phosphatidylcholine, curcumin, magnesium, melatonin, pregnenolone, ginseng, or lysergic acid diethylamide. In certain embodiments, the controlled release core comprises (a) one or more 5HT receptor agonist or a pharmaceutically acceptable salt, solvate, metabolite, derivative, or prodrug thereof; (b) at least one pharmaceutically acceptable excipient; and (c) optionally one or more agents selected from the group consisting of surfactants, preservatives, flavoring agents, sweetening agents, and antifoaming agents. In some embodiments, the pharmaceutical composition is a low-dose pharmaceutical composition. In certain embodiments, following administration to an individual in need thereof, the pharmaceutical composition provides a maximum plasma concentration ($C_{max}$) of the 5HT receptor agonist (or a pharmaceutically acceptable salt, solvate, metabolite, derivative, or prodrug thereof) of less than 6 ng/ml (e.g., the active form of the 5HT receptor agonist, regardless of the form administered) in the individual in need thereof.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

5HT (or serotonin) Receptors

Figure 1:
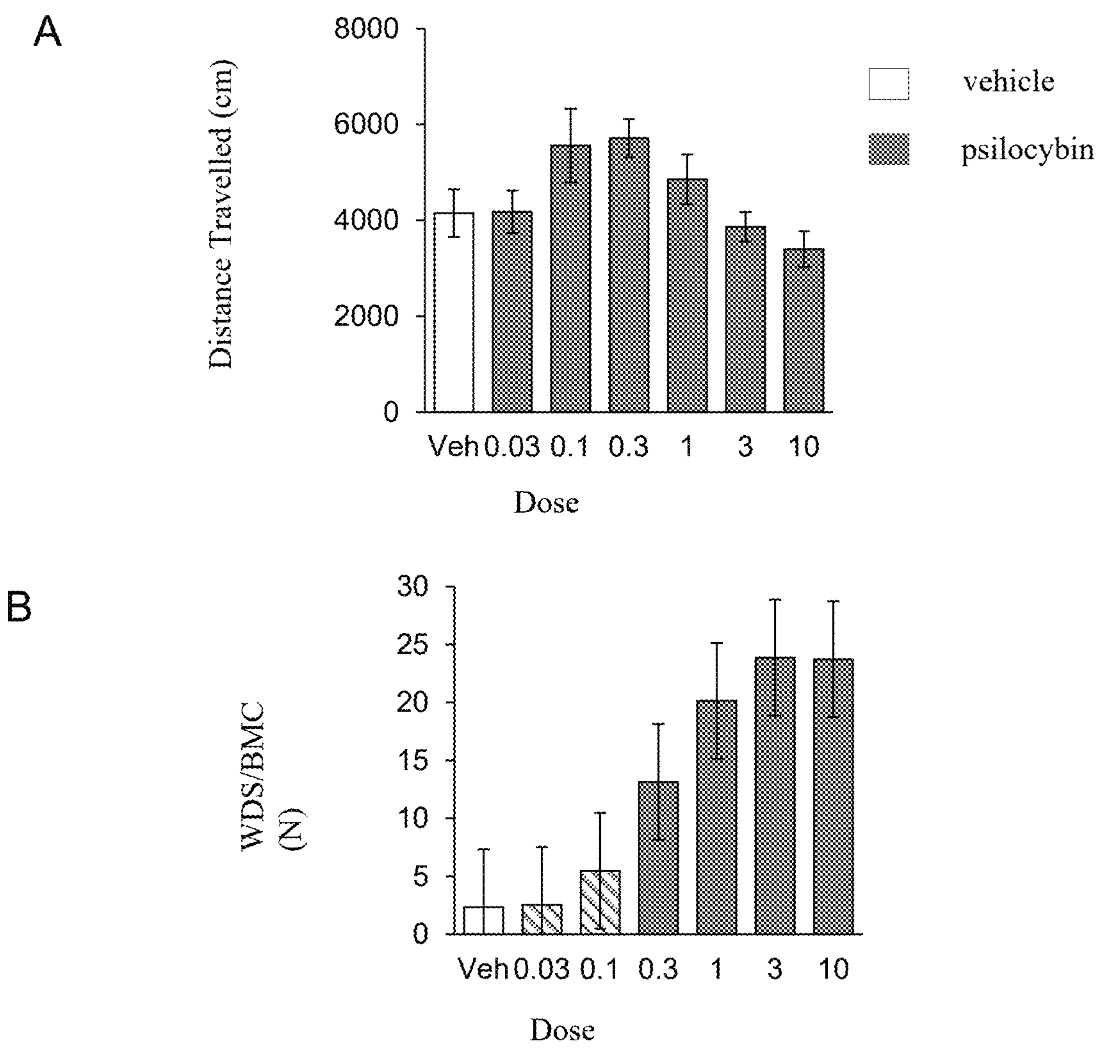
FIG. 1 shows the effects of psilocybin on locomotor activity and behavior signs in treated rats. A) Graph shows distance traveled (measured in cm) against doses of psilocybin ranging from 0.03-10 mg/kg. B) Graph shows effects of psilocybin dosing on $5\text{-HT}_{2A}$-related behaviors. The total number (N) of wet dog shakes (WDS) and back muscle contractions (BMC) is plotted against dose (mg/kg). Hatched shading indicates psilocybin doses which evoked statistically identical WDS and BMC behaviors as Vehicle.

The 5HT (or serotonin) receptors are a group of G protein-coupled receptors (GPCR) and ligand-gated ion channels. 5HT is short for 5-hydroxy-tryptamine, the chemical name for serotonin:

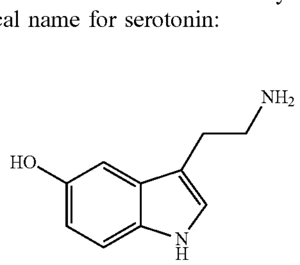

Serotonin

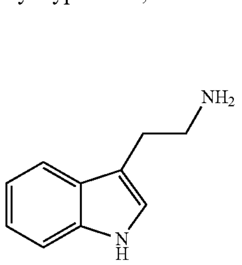

Tryptamine

The serotonin receptors are activated by serotonin, their natural ligand, and mediate both excitatory and inhibitory neurotransmission. They modulate the release of many neurotransmitters, including glutamate, GABA, dopamine, epinephrine/norepinephrine and acetylcholine, as well as many hormones, including oxytocin, prolactin, vasopressin, cortisol, corticotropin and substance P. The serotonin receptors influence various biological and neurological processes such as aggression, anxiety, appetite, cognition, learning, memory, mood, nausea, sleep, and thermoregulation.

The 5HT receptors are divided into 7 families of G protein-coupled receptors. $5HT_1$, $5HT_2$, $5HT_3$ are the major families; the others, $5HT_4$, $5HT_5$, $5HT_6$ and $5HT_7$, for the most part, work in a similar fashion to either $5HT_1$ or $5HT_2$ receptors. The 5HT receptors work with a G protein to modify an ion channel or membrane enzyme.

In certain embodiments, the 5HT agonist of a formulation, composition, method, or the like described herein is a $5HT_1$ agonist. $5HT_1$ receptors have strong binding affinity for serotonin. Typically, when serotonin binds to a $5HT_1$ receptor, a G-protein is activated, opening an ion channel and allowing potassium ions to exit the neuron. This generally causes the neuron to become more negatively charged, making it more difficult to trigger an action potential, i.e. serotonin binding to $5HT_1$ receptors is an inhibitory effect.

In some preferred embodiments, the 5HT agonist of a formulation, composition, method, or the like described herein is a $5HT_2$ agonist. In certain embodiments, the $5HT_2$ agonist has a relatively high affinity for $5HT_2$ receptors (e.g. relative to $5HT_1$ receptors and/or other 5HT receptors, such as $5HT_3$, $5HT_4$, $5HT_5$, $5HT_6$, $5HT_7$, or all or some combination thereof, such as 2×, 3×, 5×, 10×, 20×, 50×, or the like greater affinity). $5HT_2$ receptors have weaker affinity for serotonin. As such, serotonin prefers to bind $5HT_1$ receptors, typically only binding $5HT_2$ receptors once the $5HT_1$ receptors are at least partially (or wholly) saturated. Serotonin binding of $5HT_2$ receptors typically activates a G-protein closing a potassium channel resulting in potassium ion build up. This generally causes depolarization, making it easier to reach the neuron's excitation threshold. Thus, when serotonin binds to $5HT_2$ receptors, it typically has an excitatory effect.

| Family | Type | Mechanism | Potential |
|---|---|---|---|
| $5HT_1$ | Protein coupled | Decreasing cellular levels of cAMP | Inhibitory |
| $5HT_2$ | Protein coupled | Increasing cellular levels of $IP_3$ and DAG | Excitatory |
| $5HT_3$ | Ligand-gated $Na^+$ and $K^+$ cation channel | Depolarizing plasma membrane | Excitatory |

-continued

| Family | Type | Mechanism | Potential |
|---|---|---|---|
| $5HT_4$ | Protein coupled | Increasing cellular levels of cAMP | Excitatory |
| $5HT_5$ | Protein coupled | Decreasing cellular levels of cAMP | Inhibitory |
| $5HT_6$ | Protein coupled | Increasing cellular levels of cAMP | Excitatory |
| $5HT_7$ | Protein coupled | Increasing cellular levels of cAMP | Excitatory |

The seven serotonin receptor families include fourteen receptor subtypes, distributed throughout the body as shown in the table below:

| 5HT Receptor | Blood vessels | Central nervous system | Peripheral nervous system | GI Tract | Platelets | Smooth Muscle |
|---|---|---|---|---|---|---|
| 1A | ✓ | ✓ | | | | |
| 1B | ✓ | ✓ | | | | |
| 1D | ✓ | ✓ | | | | |

-continued

| 5HT Receptor | Blood vessels | Central nervous system | Peripheral nervous system | GI Tract | Platelets | Smooth Muscle |
|---|---|---|---|---|---|---|
| 1E | ✓ | ✓ | | | | |
| 1F | | ✓ | | | | |
| 2A | ✓ | ✓ | ✓ | ✓ | ✓ | ✓ |
| 2B | ✓ | ✓ | ✓ | ✓ | ✓ | ✓ |
| 2C | ✓ | ✓ | ✓ | ✓ | ✓ | ✓ |
| 3 | | ✓ | ✓ | ✓ | | |
| 4 | | ✓ | ✓ | ✓ | | |
| 5A | | ✓ | | | | |
| 5B | | | | | | |
| 6 | | ✓ | | | | |
| 7 | ✓ | ✓ | | ✓ | | |

$5HT_2$ Receptors

In general, $5HT_2$ receptors are characterized by having lower affinity for serotonin (and other indole alkylamines), and are linked to the Go/phospholipase C pathway of signal transduction. In various instances, such receptors mediate a variety of physiological and behavioral functions via three distinct subtypes: $5HT_{2A}$, $5HT_{2B}$ and $5HT_{2C}$.

| Receptor | |
|---|---|
| | Physiological/behavioral function |
| $5HT_{2A}$ | Addiction, Anxiety, Appetite, Cognition, Imagination, Learning, Memory, Mood, Perception, Sexual Behavior, Sleep, Thermoregulation, Vasoconstriction |
| $5HT_{2B}$ | Anxiety, Appetite, Cardiovascular Function, GI Motility, Sleep, Vasoconstriction |
| $5HT_{2C}$ | Addiction, Anxiety, Appetite, GI Motility, Locomotion, Mood, Penile Erection, Sexual Behavior, Sleep, Thermoregulation, Vasoconstriction |
| | Uses of drugs that act on this receptor |
| $5HT_{2A}$ | Antipsychotics, Psychedelics, Noradrenergic and Specific Serotonergic Antidepressants (NaSSAs), Sleeping aids |
| $5HT_{2B}$ | Migraines |
| $5HT_{2C}$ | Antidepressant, Orexigenic, Anorectic, Antipsychotic |
| | Drugs acting on receptor |
| $5HT_{2A}$ | Agonists<br>Bufotenin, Ergonovine, Lisuride, LSD, Mescaline, Myristicin, Psilocin, Psilocybin, DMT, DOM, PNU-22394, TFMPP, 25I-NBOMe, 2C-B, 5-MeO-DMT, BZP<br>Antagonists<br>Atypical antipsychotics , Clozapine, Olanzapine, Quetiapine, Risperidone, Ziprasidone, Aripiprazole, Asenapine, Amitriptyline, Clomipramine, Cyproheptadine, Eplivanserin, Etoperidone, Haloperidol, Hydroxyzine, Iloperidone, Ketanserin, Methysergide, Mianserin, Mirtazapine, Nefazodone, Pimavanserin, Pizotifen, Ritanserin, Trazodone, Yohimbine |
| $5HT_{2B}$ | Agonists<br>Fenfluramine, MDMA, Norfenfluramine, Methylphenidate<br>6-APB, BW-723C86, PNU-22394, Ro60-0175<br>Antagonists<br>Agomelatine, Asenapine, Ketanserin, Methysergide, Ritanserin, Tegaserod, Yohimbine, BZP, RS-127,445 |
| $5HT_{2C}$ | Agonists<br>Aripiprazole, Ergonovine, Lorcaserin, Trazodone<br>PNU-22394, Ro60-0175, TFMPP, YM-348, A-372, 159, AL-38022A<br>Antagonists<br>Agomelatine, Amitriptyline, Asenapine, Clomipramine, Clozapine, Cyproheptadine, Dimebolin, Eltoprazine, Etoperidone, Fluoxetine, Haloperidol, Iloperidone, Ketanserin, Lisuride, Methysergide, Mianserin, Mirtazapine, Nefazodone, Olanzapine, Paroxetine, Quetiapine, Risperidone, Ritanserin, Tramadol, Trazodone, Ziprasidone, SB-242084 |

$5HT_{2A}$ is an important excitatory serotonin receptor subtype. In some instances, physiological processes mediated by the receptor include, by way of non-limiting example:

- central nervous system-neuronal excitation, behavioral effects, learning, anxiety, and pro-nociception
- smooth muscle contraction (in bronchi and gastrointestinal tract)
- vasoconstriction/vasodilation
- platelet aggregation
- role in memory and learning
- anti-inflammatory activity
- hormone (oxytocin, prolactin, ACTH, corticosterone, renin) regulation
- mood regulation (depressed patients have more $5HT_{2A}$ receptors than otherwise normal individuals implying $5HT_{2A}$ is involved in the pathogenesis of depression)

In some instances, agonism of $5HT_{2A}$ agonism facilitates treatment or management of disorders involving cognitive function and social interaction, or the symptoms thereof, as evidenced by the extensive localization of the $5HT_{2A}$ receptor in brain areas that mediate cognitive functions and social interaction. In some instances, disorders in which the $5HT_{2A}$ receptor are involved include, but are not limited to schizophrenia, depression/suicide, anxiety, obsessive compulsive disorders (OCD), bipolar disorders, attention deficit hyperactivity disorder (ADHD), eating disorders such as anorexia nervosa, autism and autism spectrum disorders, Asperger's, neuropsychiatric diseases and disorders, sexual disorders such as erectile dysfunction, neurodegenerative diseases, inflammatory diseases, autoimmune diseases, metabolic diseases such as obesity and diabetes, central nervous system disorders, peripheral nervous system disorders, Alzheimer's disease, snoring, sleep apnea (obstructive sleep apnea, central sleep apnea), insomnia, sleep deprivation, restless legs syndrome, parasomnia, nightmares, night terrors, sleepwalking, hypersomnia (daytime sleepiness), narcolepsy and pain.

Any suitable 5HT (e.g. $5HT_2$, such as $5HT_{2A}$) agonist is utilized in any composition, formulation, method, therapy, or the like described herein. In some preferred embodiments, the 5HT agonist of a formulation, composition, method, or the like described herein is a $5HT_{2A}$ agonist. In certain embodiments, the $5HT_{2A}$ agonist has a relatively high affinity for $5HT_{2A}$ receptors (e.g. relative to $5HT_1$, $5HT_3$, $5HT_4$, $5HT_5$, $5HT_6$, $5HT_7$, $5HT_{2B}$, $5HT_{2C}$, or all or some combination thereof, such as 2×, 3×, 5×, 10×, 20×, 50×, or the like greater affinity). In some instances, $5HT_{2A}$ agonists increase dopamine levels in the prefrontal cortex. In certain embodiments, the $5HT_{2A}$ agonist provided herein is one of the following classes of $5HT_{2A}$ agonists: the ergolines, tryptamines and phenethylamines. In specific embodiments, a 5HT (e.g. $5HT_{2A}$) receptor agonist utilized herein is an ergoline:

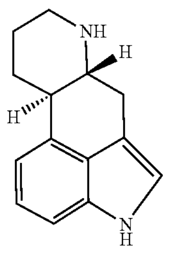

Ergoline

In some instances, ergonovine and ergotamine, synthetic derivatives include the oxytocic methergine, the anti-migraine drugs dihydroergotamine and methysergide, hydergine (a mixture of dihydroergotoxine mesylates, INN: ergoline mesylates), and bromocriptine. In certain instances, synthetic ergolines include pergolide and lisuride.

In certain instances, the ergoline is an ergoline derivative, such as a lysergic acid amide or a peptide alkaloid, such as described below. In some instances, the ergoline isa clavine (examples include festuclavine, fumigaclavine A, fumigaclavine B and fumigaclavine C) and other derivatives that do not fall into these categories, such as cabergoline, pergolide, lisuride.

Lysergic Acid Amides

Exemplary lysergic acid amides include Ergine (LSA, D-lysergic acid amide), Ergonovine (ergobasine), Methergine (ME-277), Methysergide (UML-491), LSD (D-lysergic acid diethylamide), LSH (D-lysergic acid α-hydroxyethylamide). The table below summarizes their structural formula and relationships.

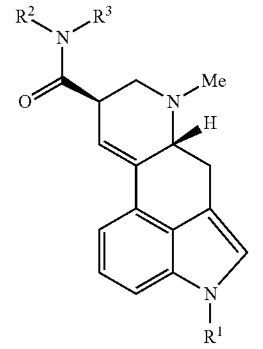

| Name | $R^1$ | $R^2$ | $R^3$ |
|---|---|---|---|
| Ergine | H | H | H |
| Ergonovine | H | $CH(CH_3)CH_2OH$ | H |
| Methergine | H | $CH(CH_2CH_3)CH_2OH$ | H |
| Methysergide | $CH_3$ | $CH(CH_2CH_3)CH_2OH$ | H |
| LSD | H | $CH_2CH_3$ | $CH_2CH_3$ |
| LSH | H | $CH(OH)CH_3$ | H |

Peptide Alkaloids

Exemplary peptide alkaloids include peptide ergot alkaloids (ergopeptines or ergopeptides), which are ergoline derivatives containing a tripeptide structure (attached at the same position as the amide group of the lysergic acid derivatives) comprising proline and two other α-amino acids. Examples include:

- Ergotoxines (valine at $R^2$)—Ergocristine, Ergocornine, α-Ergocryptine, β-Ergocryptine
- Ergotamines (alanine at $R^2$)—Ergotamine, Ergovaline, α-Ergosine, β-Ergosine

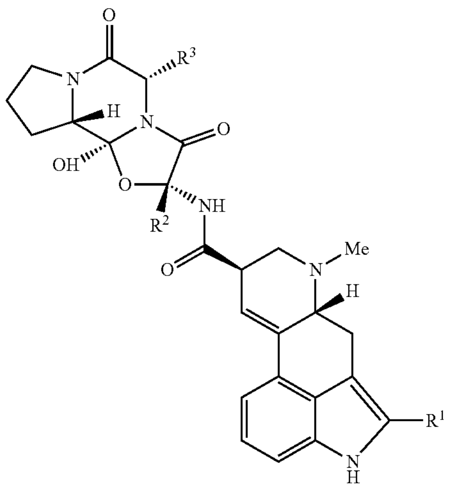

-continued

| Name | $R^1$ | $R^2$ | $R^3$ | $R^3$ Amino acid |
|---|---|---|---|---|
| Ergocristine | | $CH(CH_3)_2$ | benzyl | Phenylalanine |
| Ergocornine | | $CH(CH_3)_2$ | $CH(CH_3)_2$ | Valine |
| α-Ergocryptine | | $CH(CH_3)_2$ | $CH_2CH(CH_3)_2$ | Leucine |
| β-Ergocryptine | | $CH(CH_3)_2$ | (S)-$CH(CH_3)CH_2CH_3$ | Isoleucine |
| Ergotamine | | $CH_3$ | benzyl | Phenylalanine |
| Ergovaline | | $CH_3$ | $CH(CH_3)_2$ | Valine |
| α-Ergosine | | $CH_3$ | $CH_2CH(CH_3)_2$ | Leucine |
| β-Ergosine | | $CH_3$ | (S)-$CH(CH_3)CH_2CH_3$ | Isoleucine |
| Bromocriptine | Br | $CH(CH_3)_2$ | $CH_2CH(CH_3)_2$ | Leucine |

Tryptamines

Tryptamine (2-(1H-Indol-3-yl) ethanamine) comprises an indole ring attached to an aminoethylene group. Substituted tryptamines are substituted with any suitable group, such as being modified on the indole ring ($R^1$, $R^2$), the ethylene chain ($R^3$) and/or on the amino group ($R^4$, $R^5$) as illustrated below, and are collectively referred to herein as tryptamines.

Examples of tryptamines include serotonin, melatonin, psilocybin and N,N-dimethyltryptamine. Additionally, the tryptamine structure may comprise part of a more complex compound, for example: LSD, ibogaine, mitragynine, yohimbine, etc.

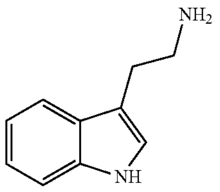

Tryptamine

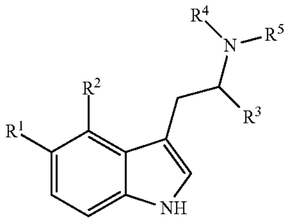

Substituted tryptamines

Examples of naturally occurring substituted tryptamines include, by way of non-limiting example:

| Short/Common Name | Full Name | $R^1$ | $R^2$ | $R^3$ | $R^4$ | $R^5$ |
|---|---|---|---|---|---|---|
| Tryptamine | 3-(2-aminoethyl)indole 2-(1H-indol-3-yl)ethanamine | H | H | H | H | H |
| Bufotenin | 5-hydroxy-N,N-dimethyltryptamine | OH | H | H | $CH_3$ | $CH_3$ |
| Nω-Methylserotonin (norbufotenin) | 5-hydroxy-N-methyltryptamine | OH | H | H | $CH_3$ | H |
| Serotonin | 5-hydroxytryptamine | OH | H | H | H | H |
| NMT | N-methyltryptamine | H | H | H | H | $CH_3$ |
| 5-MeO-NMT | 5-methoxy-N-methyltryptamine | $OCH_3$ | H | $CH_3$ | H | H |
| DMT | N,N-dimethyltryptamine | H | H | H | $CH_3$ | $CH_3$ |
| 5-Bromo-DMT | 5-bromo-N,N-dimethyltryptamine | Br | H | H | $CH_3$ | $CH_3$ |
| 5-MeO-DMT | 5-methoxy-N,N-dimethyltryptamine | $OCH_3$ | H | H | $CH_3$ | $CH_3$ |
| Melatonin | 5-methoxy-N-acetyltryptamine | $OCH_3$ | H | H | $C(O)CH_3$ | H |
| N-Acetylserotonin | 5-hydroxy-N-acetyltryptamine | OH | H | H | $C(O)CH_3$ | H |
| Norbaeocystin | 4-phosphoryloxy-tryptamine | H | $OPO_3H_2$ | H | H | H |
| Baeocystin | 4-phosphoryloxy-N-methyl-tryptamine | H | $OPO_3H_2$ | H | $CH_3$ | H |
| Psilocybin | 4-phosphoryloxy-N,N-dimethyltryptamine | H | $PO_4$ | H | $CH_3$ | $CH_3$ |
| Psilocin | 4-hydroxy-N,N-dimethyltryptamine | H | OH | H | $CH_3$ | $CH_3$ |
| Tryptophan | α-carboxyltryptamine | H | H | COOH | H | H |

Examples of synthetic substituted tryptamines include, by way of non-limiting example:

| Short Name | Name | $R^1$ | $R^2$ | $R^3$ | $R^4$ | $R^5$ |
|---|---|---|---|---|---|---|
| αET | α-ethyltryptamine | H | H | $CH_2CH_3$ | H | H |
| αMT | α-methyltryptamine | H | H | $CH_3$ | H | H |
| DALT | N,N-diallyltryptamine | H | H | H | $H_2C=CH-CH_2$ | $H_2C=CH-CH_2$ |
| DET | N,N-diethyltryptamine | H | H | H | $CH_2CH_3$ | $CH_2CH_3$ |
| DiPT | N,N-diisopropyltryptamine | H | H | H | $CH(CH_3)_2$ | $CH(CH_3)_2$ |
| DPT | N,N-dipropyltryptamine | H | H | H | $CH_2CH_2CH_3$ | $CH_2CH_2CH_3$ |
| 5-MeO-αMT | 5-methoxy-α methyltryptamine | $OCH_3$ | H | $CH_3$ | H | H |
| 5-MeO-DALT | 5-methoxy-N,N-diallyltryptamine | $OCH_3$ | H | H | $H_2C=CH-CH_2$ | $H_2C=CH-CH_2$ |
| 5-MeO-MALT | 5-methoxy-N-Methyl-N-allyltryptamine | $OCH_3$ H | H | H | $H_2C=CH-CH_2$ | $CH_3$ |
| 4-HO-DET | 4-hydroxy-N,N-diethyltryptamine | H | OH | H | $CH_2CH_3$ | $CH_2CH_3$ |
| 4-AcO-DMT | 4-acetoxy-N,N-dimethyltryptamine | H | $OCOCH_3$ | H | $CH_3$ | $CH_3$ |

-continued

| Short Name | Name | $R^1$ | $R^2$ | $R^3$ | $R^4$ | $R^5$ |
|---|---|---|---|---|---|---|
| 4-HO-MET | 4-hydroxy-N-methyl-N-ethyltryptamine | H | OH | H | $CH_3$ | $CH_2CH_3$ |
| 4-HO-DIPT | 4-hydroxy-N,N-diisopropyltryptamine | H | OH | H | $CH(CH_3)_2$ | $CH(CH_3)_2$ |
| 5-MeO-DIPT | 5-methoxy-N,N-diisopropyltryptamine | $OCH_3$ | H | H | $CH(CH_3)_2$ | $CH(CH_3)_2$ |
| 5-MeO-MiPT | 5-methoxy-N,N-methylisopropyltryptamine | $OCH_3$ | H | H | $CH_3$ | $CH(CH_3)_2$ |
| 4-HO-MiPT | 4-hydroxy-N-isopropyl-N-methyltryptamine | H | OH | H | $CH(CH_3)_2$ | $CH_3$ |
| Sumatriptan | 5-(methylamino sulfonylmethylene)-N,N-dimethyltryptamine | $CH_2SO_2NHCH_3$ | H | H | $CH_3$ | $CH_3$ |
| Zolmitriptan | 5-( 4-(S)-1,3-oxazolidin-2-one)-N,N-dimethyl-tryptamine | $CHNHC(O)OCH_2$ | H | H | $CH_3$ | $CH_3$ |

Phenethylamines

Phenethylamine comprises a phenyl ring attached to an aminoethylene group; substituted phenethylamines are optionally substituted in any suitable manner, such as they are optionally modified by substitution on the phenyl ring ($R^1$, $R^2$, $R^3$, $R^4$ and/or $R^5$), the ethylene chain ($R^6$ and/or $R^7$) and/or on the amino group ($R^8$, and/or $R^9$), such as illustrated below.

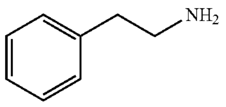

Phenethylamine

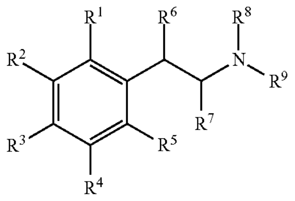

Substituted phenethylamines $R^1$, $R^2$, $R^3$, $R^4$ and/or $R^5$ = phenyl substituted
$R^6$ and/or $R^7$ = ethylene substituted
$R^8$ and/or $R^9$ = amino substituted Examples of phenethylamines include, but are not limited to those presented in the table below:

| | | Substitution | | | |
|---|---|---|---|---|---|
| Short Name | Full Name | Amino | Ethylene | Phenyl | Biological activity |
| Amphetamine | α-methylphenethylamine | | ✓ | | Stimulant |
| β-Methyl phenethylamine | β-methylphenethylamine | | ✓ | | Stimulant |
| Mephedrone | 4-methylmethcathinone | ✓ | ✓ | ✓ | Stimulant |
| Ethcathinone | N-ethylcathinone | ✓ | ✓ | | Stimulant |
| Ephedrine/ Pseudoephedrine | N-methyl-β-hydroxyamphetamine | ✓ | ✓ | | Stimulant; decongestant |
| Methamphetamine | N-methylamphetamine | ✓ | ✓ | | Stimulant; neurotoxin |
| Phentermine | α-methylamphetamine | | ✓ | | Stimulant, anorectic |
| Ortetamine | 2-methylamphetamine | | ✓ | ✓ | Stimulant, anorectic |
| Amfepramone (diethylpropion) | N-diethyl-β-ketoamphetamine | ✓ | ✓ | | Anorectic |
| Phenylephrine | β,3-dihydroxy-N-methylphenethylamine | ✓ | ✓ | ✓ | Decongestant |
| Methylphenidate | N,α-butylene-β-methoxy carbonylphenethylamine | ✓ | ✓ | | Stimulant; NDRI |
| Dopamine | 3,4-dihydroxyphenethylamine | | | ✓ | Catecholamine neurotransmitter |
| 6-Hydroxydopamine | 2,4,5-trihydroxy phenethylamine | | | ✓ | Neurotoxic agent |

-continued

| Short Name | Full Name | Substitution Amino | Ethylene | Phenyl | Biological activity |
|---|---|---|---|---|---|
| Epinephrine (Adrenaline) | β-3,4-trihydroxy-N-methylphenethylamine | ✓ | ✓ | ✓ | Catecholamine neurotransmitter |
| Norepinephrine (Noradrenaline) | β-3,4-trihydroxy phenethylamine | | ✓ | ✓ | Catecholamine neurotransmitter |
| para-Octopamine | β-4-dihydroxy phenethylamine | | ✓ | ✓ | Trace aminergic α-adrenoceptor agonist |
| Salbutamol | β-4-dihydroxy-3-hydroxymethyl-N-tert-butylphenethylamine | ✓ | ✓ | ✓ | Short-action β2-adrenergic agonist |
| N-Methyl phenethylamine | N-methylphenethylamine | ✓ | | | Amphetamine isomer |
| Cathine | d-β-hydroxyamphetamine | | ✓ | | Releasing agent |
| Cathinone | β-ketoamphetamine | | ✓ | | Releasing agent |
| Methcathinone | N-methylcathinone | ✓ | ✓ | | Releasing agent |
| Bupropion | 3-chloro-N-tert-butyl-β-ketoamphetamine | ✓ | ✓ | ✓ | NDRI |
| Norfenfluramine | 3-trifluoromethyl-amphetamine | | ✓ | ✓ | SSRA |
| Fenfluramine | 3-trifluoromethyl-N-ethylamphetamine | ✓ | ✓ | ✓ | SSRA |
| Mescaline | 3,4,5-trimethoxy phenethylamine | | | ✓ | Psychedelic |
| Proscaline | 2-(3,5-dimethoxy-4-propoxyphenyl)ethanamine | | | ✓ | Psychedelic |
| Metaescaline | 2-(3-ethoxy-4,5-dimethoxyphenyl)ethanamine | | | ✓ | Psychedelic |
| Allylescaline | 4-Allyloxy-3,5-dimethyloxy phenylethylamine | | | ✓ | Psychedelic |
| Methallylescaline | 4-Methallyloxy-3,5-dimethoxyphenethylamine | | | ✓ | Psychedelic |
| Asymbescaline | 3,4-Diethoxy-5-methoxyphenethylamine | | | ✓ | Psychedelic |

In certain embodiments, a composition or formulation described herein comprises an antidepressant. Similarly, in some embodiments, a therapeutic method provided herein comprises the administration of an antidepressant, such as utilizing a formulation or composition described herein. In certain instances, antidepressants are classified into three families: monoamine oxidase inhibitors (MAOIs), tricyclics and selective serotonin reuptake inhibitors (SSRIs). In general, SSRIs work by reducing serotonin reabsorption by the presynaptic neuron. Thus, more serotonin remains in the synaptic gap for a longer period of time, compensating for the lower levels of serotonin. SSRIs generally have fewer side effects than MAOIs or tricyclics. Notably, SSRIs typically only block the serotonin reuptake pumps, unlike the tricyclics, which also block the norepinephrine reuptake pumps. Generally, they do, however, indirectly affect norepinephrine, as norepinephrine levels are closely linked with those of serotonin; raising serotonin levels automatically raises norepinephrine levels.

Examples of selective serotonin reuptake inhibitors include, by way of non-limiting example, fluoxetine (PROZAC®), citalopram (CELEXA®), fluvoxamine (LUVOX®), sertraline (ZOLOFT®), and paroxetine (PAXIL®).

In certain embodiments, described herein are pharmaceutical compositions, comprising 5HT receptor agonist, or pharmaceutically acceptable salt, solvate, metabolite, derivative, or prodrug thereof, such agents being collectively referred to herein as 5HT receptor agonist agents. In some instances, the pharmaceutical compositions or formulations of 5HT receptor agonist, or pharmaceutically acceptable salt, solvate, metabolite, derivative, or prodrug thereof, have enhanced bioavailability and efficacy, have a lower administration dose, a lower cytotoxicity, and/or have decreased side effects.

Methods of Treatment

Provided herein are methods for managing disorders or conditions, and treating symptoms of disorders or conditions, comprising administering one or more 5HT receptor agonists, or pharmaceutically acceptable salts, solvates, metabolites, derivatives, or prodrugs thereof. The methods provide improved dosage and administration, enabling enhanced bioavailability and efficacy to subjects in need thereof.

Further provided herein are methods of managing neurological conditions or the symptoms thereof in a subject in need thereof, comprising administering to the subject a pharmaceutical composition comprising a therapeutically effective amount of one or more 5HT receptor agonist or a pharmaceutically acceptable salt, solvate, metabolite, derivative, or prodrug thereof and a pharmaceutically acceptable excipient.

Further provided herein are methods of treating the symptoms of a neurological condition in a subject suffering from the neurological condition, comprising administering to the subject a pharmaceutical composition comprising a therapeutically effective amount of one or more 5HT receptor agonist or a pharmaceutically acceptable salt, solvate, metabolite, derivative, or prodrug thereof and a pharmaceutically acceptable excipient.

Further provided herein are methods of treating the symptoms of a neurological condition in a subject susceptible to the neurological condition, comprising administering to the subject a pharmaceutical composition comprising a therapeutically effective amount of one or more 5HT receptor agonist or a pharmaceutically acceptable salt, solvate, metabolite, derivative, or prodrug thereof and a pharmaceutically acceptable excipient.

Further provided herein are methods for managing neurological disorders or conditions, comprising administering one or more 5HT receptor agonists, or pharmaceutically acceptable salts, solvates, metabolites, derivatives, or prodrugs thereof. Further provided herein are methods for treating the symptoms of neurological disorders or conditions, comprising administering one or more 5HT receptor agonists, or pharmaceutically acceptable salts, solvates, metabolites, derivatives, or prodrugs thereof.

Further provided herein are methods of managing neurological conditions or the symptoms thereof in a subject in need thereof, comprising administering to the subject a pharmaceutical composition comprising a therapeutically effective amount of one or more 5HT2 receptor agonist or a pharmaceutically acceptable salt, solvate, metabolite, derivative, or prodrug thereof and a pharmaceutically acceptable excipient.

Further provided herein are methods wherein 5HT receptor agonist is a 5HT2 receptor agonist. Further provided herein are methods wherein the 5HT2 receptor agonist is a 5HT2A receptor agonist, a 5HT2B receptor agonist and/or a 5HT2C receptor agonist.

In some embodiments, any suitable dosage of 5HT receptor agonist may be administered to an individual in need thereof, such as about 0.1 mg to about 10 mg or about 10 mg to about 50 mg is administered. In certain embodiments, the 5HT receptor agonist is administered in a dosage form that provides at least some release of active over a period of at least 12 hours, at least 24 hours, at least 48 hours, at least 72 hours, at least 96 hours, or any suitable or desirous time period.

Further provided herein are methods wherein the 5HT receptor agonist or a pharmaceutically acceptable salt, solvate, metabolite, derivative, or prodrug thereof is present in an amount of from about 0.1 mg to about 50 mg (e.g. about 0.1 mg to about 10 mg, about 0.2 mg to about 5 mg, about 10 mg to about 50 mg, or the like). Further provided herein are methods wherein the 5HT receptor agonist or a pharmaceutically acceptable salt, solvate, metabolite, derivative, or prodrug thereof is present in an amount of about 10 mg. Further provided herein are methods wherein the 5HT receptor agonist or a pharmaceutically acceptable salt, solvate, metabolite, derivative, or prodrug thereof is present in an amount of about 20 mg. Further provided herein are methods wherein the 5HT receptor agonist or a pharmaceutically acceptable salt, solvate, metabolite, derivative, or prodrug thereof is present in an amount of about 30 mg. Further provided herein are methods wherein the 5HT receptor agonist or a pharmaceutically acceptable salt, solvate, metabolite, derivative, or prodrug thereof is present in an amount of about 40 mg. Further provided herein are methods wherein the 5HT receptor agonist or a pharmaceutically acceptable salt, solvate, metabolite, derivative, or prodrug thereof is present in an amount of about 50 mg.

Further provided herein are methods wherein the therapeutically effective amount of the 5HT receptor agonist or a pharmaceutically acceptable salt, solvate, metabolite, derivative, or prodrug thereof is provided to the subject in need thereof in an amount insufficient to provide an adverse side effect, such as hallucinogenic experience.

Further provided herein are methods wherein the therapeutically effective amount of 5HT receptor agonist (e.g. psilocybin) or a pharmaceutically acceptable salt, solvate, metabolite (e.g. psilocin, an active metabolite of psilocybin), derivative, or prodrug thereof is provided to a subject in need thereof in an amount and/or formulation to provide a maximum plasma concentration ($C_{max}$) of (e.g. active form of the) 5HT receptor agonist or a pharmaceutically acceptable salt, solvate, metabolite, derivative, or prodrug thereof of about 0.1 ng/ml or more and less than 6 ng/ml (e.g. at least 0.5 ng/ml and less than 6 ng/ml, about 1 ng/ml to about 5.5 ng/mL, about 2 ng/ml to about 5 ng/mL, or the like).

In some embodiments, a method provided herein comprises providing a 5HT receptor agonist (e.g. in a sufficient dosage and suitable formulation) to provide a minimum therapeutic concentration of (e.g. active form of the) 5HT receptor agonist or a pharmaceutically acceptable salt, solvate, metabolite, derivative, or prodrug thereof for at least 12 hours, at least 24 hours, at least 36 hours, at least 48 hours, at least 72 hours, at least 96 hours, or the like.

In various embodiments provided herein, 5HT receptor agonist or a pharmaceutically acceptable salt, solvate, metabolite, derivative, or prodrug thereof is administered in any suitable frequency. In some instances, administration is daily, every other day, about twice a week, at least three times a week (e.g. five days on and two days off), or on any suitable schedule.

In some embodiments, also disclosed herein is a method of managing a neurological condition or one or more symptoms thereof in a subject in need thereof, comprising administering to the subject a pharmaceutical composition comprising: a) a therapeutically effective amount of one or more 5HT receptor agonist or a pharmaceutically acceptable salt, solvate, metabolite, derivative, or prodrug thereof; and b) a pharmaceutically acceptable excipient; wherein the therapeutically effective amount of the 5HT receptor agonist or a pharmaceutically acceptable salt, solvate, metabolite, derivative, or prodrug thereof is provided to the subject in need thereof in an amount insufficient to provide an adverse side effect, such as hallucinogenic experience.

In some embodiments, also disclosed herein is a method of treating the symptoms of a neurological condition in a subject suffering from or susceptible to the neurological condition, comprising administering to the subject a pharmaceutical composition comprising: a) a therapeutically effective amount of one or more 5HT receptor agonist or a pharmaceutically acceptable salt, solvate, metabolite, derivative, or prodrug thereof; and b) a pharmaceutically acceptable excipient; wherein the therapeutically effective amount of the 5HT receptor agonist or a pharmaceutically acceptable salt, solvate, metabolite, derivative, or prodrug thereof is provided to the subject in need thereof in an amount insufficient to provide an adverse side effect, such as hallucinogenic experience.

In some embodiments, the 5HT receptor agonist or a pharmaceutically acceptable salt, solvate, metabolite, derivative, or prodrug thereof is present in an amount of from about 0.1 mg to about 50 mg (e.g. about 0.1 mg to about 10 mg, about 0.2 mg to about 5 mg, about 10 mg to about 50 mg, or the like). In some embodiments, the 5HT receptor agonist or a pharmaceutically acceptable salt, solvate, metabolite, derivative, or prodrug thereof is present in an amount of from about 0.1 mg to about 2 mg. In some embodiments, the 5HT receptor agonist or a pharmaceutically acceptable salt, solvate, metabolite, derivative, or prodrug thereof is present in an amount of from about 1 mg to about 15 mg. In some embodiments, the pharmaceutical composition is a low-dose pharmaceutical composition. In some embodiments, the pharmaceutical composition comprises a controlled release component. In some embodiments, the pharmaceutical composition comprises a controlled release component and an immediate release component.

In some embodiments, the therapeutically effective amount of 5HT receptor agonist or a pharmaceutically acceptable salt, solvate, metabolite, derivative, or prodrug thereof is provided to a subject in need thereof in an amount and/or formulation insufficient to provide a maximum plasma concentration ($C_{max}$) of (e.g. active form of the) 5HT receptor agonist or a pharmaceutically acceptable salt, solvate, metabolite, derivative, or prodrug thereof of 6 ng/ml or more. In some embodiments, the therapeutically effective amount of 5HT receptor agonist or a pharmaceutically acceptable salt, solvate, metabolite, derivative, or prodrug thereof is provided to a subject in need thereof in an amount and/or formulation to provide a maximum plasma concentration ($C_{max}$) of (e.g. active form of the) 5HT receptor agonist or a pharmaceutically acceptable salt, solvate, metabolite, derivative, or prodrug thereof of about 0.1 ng/ml or more and less than 6 ng/ml (e.g. at least 0.5 ng/ml and less than 6 ng/ml, about 1 ng/ml to about 5.5 ng/mL, about 2 ng/mL to about 5 ng/mL, or the like). In some embodiments, the therapeutically effective amount of 5HT receptor agonist or a pharmaceutically acceptable salt, solvate, metabolite, derivative, or prodrug thereof is provided to a subject in need thereof in an amount and/or formulation to provide a plasma concentration of (e.g. active form of the) 5HT receptor agonist or a pharmaceutically acceptable salt, solvate, metabolite, derivative, or prodrug thereof of at least 0.1 ng/ml (e.g. at least 0.2 ng/ml, at least 0.3 ng/ml, at least 0.5 ng/ml, or the like) after at least 6 hours (e.g. at least 12 hours, at least 24 hours, at least 36 hours, at least 48 hours, at least 72 hours, at least 96 hours, at least 120 hours, at least 144 hours, or the like).

In some embodiments, the 5HT receptor agonist is a 5HT2 receptor agonist. In some embodiments, the 5HT receptor agonist is psilocybin or a pharmaceutically acceptable salt, solvate, metabolite, derivative, or prodrug thereof. In some embodiments, the 5HT receptor agonist is psilocin or a pharmaceutically acceptable salt, solvate, metabolite, derivative, or prodrug thereof.

In some embodiments, the pharmaceutical composition further comprises one or more agents selected from the group consisting of surfactants, preservatives, flavoring agents, sweetening agents, and antifoaming agents. In some embodiments, the pharmaceutical composition is an oral formulation, a buccal formulation, a nasal formulation, or an inhalation formulation. In some embodiments, the pharmaceutical composition is in a form selected from a spray, aerosol, mist, nebulae, ointment, cream, gel, paste, salve, solution, suspension, tincture, patch, and atomized vapor.

In some embodiments, the pharmaceutical composition further comprises an effective amount of a second agent. In some embodiments, the second agent is a vasodilator or vasoconstrictor. In some embodiments, the vasoconstrictor is epinephrine, phenylephrine, methoxamine, norepinephrine, zolmitriptan, tetrahydrozaline, naphazoline, or combinations thereof. In some embodiments, the second agent is a stimulant, an antihistamine, an antiemetic, an antidepressant, an anti-inflammatory, a growth factor, a lithium compound, resveratrol, phosphatidylcholine, curcumin, magnesium, melatonin, pregnenolone, ginseng, lysergic acid diethylamide, or combinations thereof. In some embodiments, the second agent is a 5HT receptor antagonist. In some embodiments, the second agent is an anti-psychotic agent. In some embodiments, the anti-psychotic agent is olanzapine, clozapine, risperidone, paliperidone, aripiprazole, quetiapine, iloperidone, ziprasidone, asenapine, lurasidone, sertindole, amisulpride, clotiapine, mosapramine, perospirone, sulpiride, zotepine, haloperidol, benperidol, loxapine, molindone, pimozide, thioridazine, mesoridazine, thiothixene, chlorprothixene, fluphenazine, trifluoperazine, chlorpromazine, perphenazine, prochlorperazine, droperidol, and zuclopenthixol. In some embodiments, the second agent is a norepinephrine modulator, an alpha adrenergic agonist (e.g. clonidine), a beta adrenergic antagonists (e.g. propranolol), or any combination thereof. In some embodiments, the second agent is administered simultaneously, sequentially, or alternately with the pharmaceutical composition. In some embodiments, the second agent is administered simultaneously, sequentially, or alternately with the pharmaceutical composition.

In some embodiments, the pharmaceutical composition is administered first and the second agent is administered at least once before the pharmaceutical composition is administered a subsequent time. In some embodiments, the pharmaceutical composition is administered first and the second agent is administered more than once before the pharmaceutical composition is administered a subsequent time. In some embodiments, the pharmaceutical composition is administered to a subject in need thereof no more frequently than once a day (e.g. no more frequently than once every other day, no more frequently than once every third day, no more frequently than twice a week, no more frequently than once a week, no more frequently than once every two weeks, or the like). In some embodiments, the pharmaceutical composition is administered to a subject in need thereof once a day, every alternate day, three times a week, twice a week, once a week, every other week, two weeks per month, three weeks per month, once a month, twice a month or three times per month. In some embodiments, the pharmaceutical composition is administered about once a day. In some embodiments, the pharmaceutical composition is administered about every alternate day. In some embodiments, the pharmaceutical composition is administered about once a week. In some embodiments, the pharmaceutical composition is administered about once every two weeks or more. In some embodiments, the pharmaceutical composition is administered for at least 1 month, 2 months, 3 months, 4 months, 5 months, 6 months, 7 months, 8 months, 9 months, 10 months, 11 months, 12 months, 18 months, 2 years, or 3 years.

In some embodiments, the neurological condition is a neurological disorder. In some embodiments, the neurological condition is a neurocognitive disorder. In some embodiments, the symptoms of the neurological condition are physical, behavioral, emotional, mental or a combination thereof. In some embodiments, the neurological condition is an addictive disorder. In some embodiments, the addictive disorder is alcohol abuse, substance abuse, smoking, or obesity. In some embodiments, the neurological condition is an eating disorder or an auditory disorder. In some embodiments, the neurological condition is pain (e.g. chronic pain). In some embodiments, the neurological condition is depression, bipolar disorder, anxiety, social anxiety, post-traumatic stress disorder (PTSD), panic disorder, phobia, schizophrenia, psychopathy, or antisocial personality disorder. In some embodiments, the neurological condition is an impulsive disorder. In some embodiments, the impulsive disorder is attention deficit hyperactivity disorder (ADHD), attention deficit disorder (ADD), Tourette's syndrome or autism. In some embodiments, the neurological condition is a compulsive disorder. In some embodiments, the compulsive disorder is obsessive compulsive disorder (OCD), gambling, or aberrant sexual behavior. In some embodiments, the neurological condition is a personality disorder. In some embodiments, the personality disorder is conduct disorder, antisocial personality, or aggressive behavior.

Oral Formulations

In some embodiments, described herein are compositions and formulations comprising a 5HT receptor agonist active ingredient. In some embodiments, the formulation comprising 5HT receptor agonist, or pharmaceutically acceptable salt, solvate, metabolite, derivative, or prodrug thereof, has an enhanced bioavailability and efficacy, has a lower administration dose, a lower cytotoxicity, and has decreased side effects.

In some embodiments, the composition or formulation is an oral formulation. In some instances, the oral formulation comprising 5HT receptor agonist, or pharmaceutically acceptable salt, solvate, metabolite, derivative, or prodrug thereof, has an enhanced bioavailability and efficacy, has a lower administration dose, a lower cytotoxicity, and has decreased side effects.

In some embodiments, the pharmaceutically acceptable excipient is selected from the group consisting of fillers, binders, suspending agents, disintegrants, lubricants, and combinations thereof.

In some embodiments, the composition or formulation (e.g. oral composition or formulation) comprises a filler. In some embodiments, the amount of the filler is from about 10% to about 20% by weight. In some embodiments, the amount of the filler is from about 10% to about 40% by weight. In some embodiments, the amount of the filler is from about 20% to about 40% by weight. In some embodiments, the amount the filler is about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, or about 40% w/w.

In some embodiments, the composition or formulation (e.g. oral composition or formulation) comprises a binder. In some embodiments, the amount of the binder is from about 5% to about 15% by weight. In some embodiments, the amount of the binder is from about 5% to about 25% by weight. In some embodiments, the amount of the binder is from about 15% to about 25% by weight. In some embodiments, the amount of the binder is about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, or about 25% w/w.

In some embodiments, the composition or formulation (e.g. oral composition or formulation) comprises a suspending agent. In some embodiments, the amount of the suspending agent is from about 2% to about 3% by weight. In some embodiments, the amount of the suspending agent is from about 2% to about 4% by weight. In some embodiments, the amount of the suspending agent is from about 1% to about 5% by weight. In some embodiments, the amount of the suspending agent is about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, or about 5% w/w.

In some embodiments, the composition or formulation (e.g. oral composition or formulation) comprises a disintegrant. In some embodiments, the amount of the disintegrant is from about 2% to about 3% by weight. In some embodiments, the amount of the disintegrant is from about 2% to about 4% by weight. In some embodiments, the amount of the disintegrant is from about 1% to about 5% by weight. In some embodiments, the amount of the disintegrant is about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, or about 5% w/w.

In some embodiments, the composition or formulation (e.g. oral composition or formulation) comprises a lubricant. In some embodiments, the amount of the lubricant is from about 2% to about 3% by weight. In some embodiments, the amount of the lubricant is from about 2% to about 4% by weight. In some embodiments, the amount of the lubricant t is from about 1% to about 5% by weight. In some embodiments, the amount of the lubricant is about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, or about 5% w/w.

In some embodiments, the composition or formulation (e.g. oral composition or formulation) comprises a surfactant. In some embodiments, the amount of the surfactant is from about 0.1% to about 2% by weight. In some embodiments, the amount of the surfactant is from about 0.1% to about 5% by weight. In some embodiments, the amount of the surfactant is from about 1% to about 15% by weight. In some embodiments, the amount of the surfactant is about 0.5% w/w, about 0.6% w/w, about 0.7% w/w, about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5%, about 6%, about 7%, about 8%, about 9%, about 10%, about 11%, about 12%, about 13%, about 14%, or about 15%.

In some embodiments, the amount of the surfactant is from about 0.5% to about 5% by weight. In some embodiments, the amount of the surfactant is about 0.5% by weight. In some embodiments, the amount of the surfactant is about 1% by weight. In some embodiments, the amount of the surfactant is about 2% by weight. In some embodiments, the amount the surfactant is about 3% by weight. In some embodiments, the amount of the surfactant is about 4% by weight. In some embodiments, the amount of the surfactant is from about 7% to about 15% by weight. In some embodiments, the amount of the surfactant is from about 0.5% to about 2% by weight.

Bi-Layer Formulations

In some embodiments, the composition or formulation is or comprises a bi-layer formulation (e.g. oral dosage form). In some instances, the bi-layer formulation comprising 5HT receptor agonist, or pharmaceutically acceptable salt, solvate, metabolite, derivative, or prodrug thereof, has an enhanced bioavailability and efficacy, has a lower administration dose, a lower cytotoxicity, and/or has decreased side effects.

In some embodiments, the bi-layer formulation is an oral dosage form comprising an (e.g. immediate release or controlled release) top layer or coating and a controlled release core, such as wherein at least one of (i) the top layer or coating, or (ii) the controlled release core comprise a 5HT (e.g. $5HT_2$) receptor agonist. In specific instances, the (e.g. immediate release or controlled release) top layer or coating and the controlled release core both comprise a 5HT (e.g. $5HT_2$) receptor agonist, the core and coating 5HT receptor agonist being the same or different. Additional agents are contemplated in either or both the (i) top layer or coating and (ii) the core, such as any additional agent described herein (e.g. stimulant, an antihistamine, an antiemetic, an antidepressant, an anti-inflammatory, a growth factor, a lithium compound, resveratrol, phosphatidylcholine, curcumin, magnesium, melatonin, pregnenolone, ginseng, tryptophan, lysergic acid diethylamide, a 5HT receptor antagonist, or any combination thereof).

Controlled Release Coating Formulations

In some embodiments, at least one (e.g. controlled-release) coating (e.g. at least partially, or wholly) surrounds the core of the oral dosage form. In certain embodiments the controlled release coating is a stable controlled release monolithic coating that is formed by a process that comprises coating the core with a coating composition to form a coated core with an intermediate coating, and curing the coated core to form the stable controlled release coating. In at least one embodiment the coating composition comprises an aqueous dispersion of a neutral ester copolymer without any functional groups, a poly-glycol having a melting point of at least 55° C., and one or more second pharmaceutically acceptable excipients. In some instances, the curing is conducted at a temperature at least equal to or greater than the melting point of the poly-glycol. In at least one embodiment the stable controlled release coating comprises a neutral ester copolymer without any functional groups, a poly-glycol having a melting point of at least 55° C., and one or more second pharmaceutically acceptable excipients.

In certain embodiments, a coating composition (e.g. utilized to form a coating) comprises an aqueous dispersion of a neutral ester copolymer without any functional groups. In some embodiments, the aqueous dispersion of a neutral ester copolymer without any functional groups is an ethyl acrylate and methyl methacrylate copolymer dispersion. Non-limiting examples of ethyl acrylate and methyl methacrylate copolymer dispersions include a 30% aqueous dispersion of a neutral copolymer based on ethyl acrylate and methyl methacrylate (e.g. Eudragit® NE30D), a 40% aqueous dispersion of a neutral copolymer based on ethyl acrylate and methyl methacrylate (e.g. Eudragit® NE40D), Eudragit® NM30D, Kollicoat® EMM30D, and combinations thereof. In at least one embodiment the neutral ester copolymer without any functional groups used in the controlled release coating composition is Eudragit® NE30D, Eudragit® NE40D, or a mixture thereof. The neutral ester copolymer without any functional groups might be present in certain embodiments in an amount of from about 1% to about 35% by weight of the coating composition, depending on the therapeutically active agent used and the controlled release profile desired. In certain embodiments the neutral ester copolymer without any functional groups is present in an amount from about 20% to about 99.5% by dry weight of the coat. In other embodiments the neutral ester copolymer without any functional groups is present in an amount from about 25% to about 60% by dry weight of the coat. In still other embodiments the neutral ester copolymer without any functional groups is present in an amount from about 37% to about 50% by dry weight of the coat. In some embodiments, the neutral ester copolymer without any functional groups is present in an amount of about 38%, about 39%, about 40%, about 41%, about 42%, about 43%, about 44%, about 45%, about 46%, about 47%, about 48%, and about 49% by dry weight of the coat. In certain embodiments, the neutral ester copolymer without any functional groups is present in the coating composition in an amount of from about 0.4% to about 39.8% by dry weight of the tablet. in other embodiments in an amount of from about 0.8% to about 24% by dry weight of the tablet. In some other embodiments, the neutral ester copolymer without any functional groups is present in the coating composition in an amount of from about 2% to about 5.5% by dry weight of the tablet, for example, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4% by dry weight of the tablet.

In some embodiments, the controlled release dosage form does not swell in a dimensionally unrestricted manner upon imbibition of water. In certain embodiments there is some swelling of the controlled release dosage form in a dimensionally restricted manner upon imbibition of water. In certain embodiments the controlled release coating restricts the swelling of the dosage form upon imbibition of water.

In certain embodiments, a coating composition comprises a polyglycol, such as with a melting point of at least about 55° C. In some embodiments, the polyglycol with a melting point of at least about 55° C. is a polyethylene glycol with an average molecular weight ranging from about 4,000 Daltons to about 35,000 Daltons. Non-limiting examples of a polyglycol with a melting point of at least about 55° C. include, by way of non-limiting example, polyethylene glycol 4000, polyethylene glycol 4600, polyethylene glycol 6000, polyethylene glycol 8000, polyethylene glycol 10000, polyethylene glycol 12000, polyethylene glycol 20000, polyethylene glycol 35000, or mixtures thereof. In certain embodiments, the polyglycol is selected from the group consisting of polyethylene glycol 6000, polyethylene glycol 8000, polyethylene glycol 10000, polyethylene glycol 12000, and mixtures thereof. In at least one embodiment the poly-glycol used in the coating composition is polyethylene glycol 8000. The polyglycol might be present in certain embodiments in an amount of from about 0.1% to about 10% by weight of the coating composition. In certain embodiments the poly-glycol is present in an amount of from about 0.5% to about 28% by dry weight of the coat. In other embodiments the polyglycol is present in an amount from about 4% to about 17% by dry weight of the coat. In still other embodiments the polyglycol is present in an amount from about 7.2% to about 15.2% by dry weight of the coat, for example, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 10.1%, about 10.2%, about 10.3%, about 10.4%, about 10.5%, about 10.6%, about 10.7%, about 10.8%, about 10.9%, about 11%, about 11.1%, about 11.2%, about 11.3%, about 11.4%, about 11.5%, about 11.6%, about 11.7%, about 11.8%, about 11.9%, about 12%, about 12.1%, about 12.2%, about 12.3%, about 12.4%, about 12.5%, about 12.6%, about 12.7%, about 12.8%, about 12.9%, about 13%, about 13.1%, about 13.2%, about 13.3%, about 13.4%, about 13.5%, about 13.6%, about 13.7%, about 13.8%, about 13.9%, about 14%, about 14.1%, about 14.2%, about 14.3%, about 14.4%, about 14.5%, about 14.6%, about 14.7%, about 14.8%, about 14.9%, about 15%, and about 15.1% by dry weight of the coat. In certain embodiments the poly-glycol is present in the coating composition in an amount of from about 0.1% to about 11.2% by dry weight of the tablet. In other embodiments the polyglycol is present in the coating composition in an amount of from about 0.1% to about 8% by dry weight of the tablet. In still other embodiments the polyglycol is present in the coating composition in an amount of from about 0.2% to about 2.8% by dry weight of the tablet, for example, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, and about 2.7% by dry weight of the tablet. Other suitable polyglycol derivatives having a melting point of at least about 55° C. might be, but are not limited to, Poloxamer 188, Poloxamer 338, Poloxamer 407, polyethylene oxides, polyoxyethylene alkyl ethers, polyoxyethylene stearates, and mixtures thereof.

In addition to the copolymers and the polyglycol, the coating composition optionally comprises one or more other pharmaceutically acceptable excipients. The excipients can include, but not limited to, anti-tacking agents, emulsifying agents, antifoaming agents, hydrophilic agents, flavorings, colorants, sweeteners, etc., and any combination thereof. In some embodiments, excipients might affect the properties of the coat in a series of ways, and many substances used in coat formulations might thus be described as multifunctional. A skilled worker will know, based on their technical knowledge, which pharmaceutically acceptable excipients are suitable for the desired controlled release coating composition.

In some embodiments, hydrophilic agents are included in a composition, formulation, core or coating described herein, such as to promote wetting of the coating when in contact with gastrointestinal fluids. Such hydrophilic agents include, by way of non-limiting example, hydrophilic water soluble polymers such as hydroxypropyl methylcellulose (HPMC) (e.g. Pharmacoat® 606 or Hypromellose), hydroxypropyl cellulose (HPC), methyl cellulose, hydroxyethyl cellulose, hydroxyethyl methylcellulose, polyvinylpyrrolidone (Povidone® or Kollidon®), polyvinyl alcohol, polyethylene oxide, vinylpyrrolidone-vinyl acetate copolymer (Kollidon® VA64), polyethylene glycol-polyvinyl alcohol copolymer (Kollicoat® IR), copolymers thereof, and combinations thereof. In at least one embodiment, HPMC is the hydrophilic agent used in the coating composition. In certain embodiments, the hydrophilic agent comprises a pH-dependent polymer, non-limiting examples of which include: cellulose acetate phthalate (e.g. Aquacoat® CPD); cellulose acetate trimellitate, poly(methacrylic acid, ethyl acrylate) 1:1 (e.g. Eudragit® L30D-55); Kollicoat® MAE 30 D; poly(methacrylic acid, ethyl acrylate) 1:1 (e.g. Eudragit® L100-55); Kollicoat® MAE 30 DP; Eudragit® FS 30D; Hypromellose Acetate Succinate LF, MF, HF grades (e.g. AQOAT®), polyvinyl acetate phthalate, and mixtures thereof. If hydrophilic agents are to be included in the coat composition the agents are present in any suitable amount, such as, in certain embodiments, in an amount from about 0.1% to about 10% by weight of the coating composition. In other embodiments from about 0.1% to about 5% by weight of the coating composition, and in still other embodiments from about 0.1% to about 3% by weight of the coating composition. In certain embodiments the hydrophilic agent is present in an amount of from greater than about 0% to about 35% by dry weight of the coat. In other embodiments the hydrophilic agent is present in an amount from about 8% to about 30% by dry weight of the coat. In still other embodiments the hydrophilic agent is present in an amount from about 12% to about 26% by dry weight of the coat, for example, about 13%, about 14%, about 15%, about 16%, about 17%, about 18%, about 19%, about 20%, about 21%, about 22%, about 23%, about 24%, and about 25% by dry weight of the coat. In certain embodiments the hydrophilic agent is present in the coating formulation in an amount of from about 0% to about 14% by dry weight of the tablet; in other embodiments in an amount of from about 0.2% to about 6% by dry weight of the tablet; and in still other embodiments in an amount of from about 0.8% to about 2.5% by dry weight of the tablet; for example, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, and about 2.4% by dry weight of the tablet.

In some instances, the tackiness of polymeric films is important for the coating of dosage forms and for the subsequent curing step (post-coating thermal treatment). In certain instances, during coating with either cellulosic or acrylic polymers, an unwanted, and sometimes irreversible agglomeration of several granules or beads or, in the worst case, of the complete batch, might occur, especially at higher product processing temperatures. Accordingly, in some embodiments, the addition of anti-tacking agents to coating formulations is desirable. The anti-tacking agents which are optionally used include but are not limited to adipic acid, magnesium stearate, calcium stearate, zinc stearate, hydrogenated vegetable oils, sterotex, glyceryl monostearate, talc (e.g. Talc 400), sodium benzoate, sodium lauryl sulfate, magnesium lauryl sulfate, and mixtures thereof. In at least one embodiment talc (e.g. talc 400) is used as the anti-tacking agent. In some instances, talc also functions as a wetting agent. In some embodiments, mixtures of the anti-tacking agents are utilized. Any suitable amount of anti-tacking agent is utilized in the coating composition, such from about 1% to about 15% by weight of the coating dispersion, and in certain embodiments from about 1% to about 7% by weight of the coating dispersion. In certain embodiments the anti-tacking agent is present in an amount of from greater than about 0% to about 50% by dry weight of the coating. In other embodiments the anti-tacking agent is present in an amount from about 2% to about 40% by dry weight of the coating. In still other embodiments the anti-tacking agent is present in an amount from about 10% to about 30% by dry weight of the coating; for example, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, and about 29% by dry weight of the coating. In certain embodiments the anti-tacking agent is present in the coating formulation in an amount of from about 0% to about 20% by dry weight of the tablet; in other embodiments in an amount of from about 0% to about 12% by dry weight of the tablet; and in still other embodiments in an amount of from about 0.6% to about 7% by dry weight of the tablet; for example, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, and about 6.9% by dry weight of the tablet.

In certain embodiments, a composition, formulation, core or coating described herein comprises an anti-foaming agent, such as, by way of non-limiting example, silicon oil, simethicone (e.g. simethicone emulsion), and mixtures thereof. In at least one embodiment the anti-foaming agent is simethicone. The anti-foaming agent, if present, is utilized in any suitable amount, such as in an amount of up to about 0.5% by weight of the coat composition, and in certain other embodiments from about 0.1% to about 0.4% by weight of the coating composition. In certain embodiments the anti-foaming agent is present in an amount of from greater than about 0% to about 3% by dry weight of the coat. In other embodiments the anti-foaming agent is present in an amount from about 0.4% to about 2% by dry weight of the coat. In still other embodiments the anti-foaming agent is present in an amount from about 0.8% to about 1.5% by dry weight of the coat; for example, about 0.9%, about 1%, about 1.1%, about 1.2%, about 1.3%, and about 1.4% by dry weight of the coat. In certain embodiments the anti-foaming agent is present in the coating formulation in an amount of from about 0% to about 1.2% by dry weight of the tablet; in other embodiments in an amount of from about 0% to about 0.8% by dry weight of the tablet; and in still other embodiments in an amount of from about 0% to about 0.2% by dry weight of the tablet; for example, about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, and about 0.19% by dry weight of the tablet.

In some embodiments, an emulsifying agent (also called emulsifiers or emulgents) is included in a composition, formulation, core or coating described herein, such as to facilitate actual emulsification during manufacture of the coating, and/or to provide emulsion stability during the shelf-life of the product. In some instances, suitable emulsifying agents include, but are not limited to naturally occurring materials and their semi synthetic derivatives, such as the polysaccharides, as well as glycerol esters, cellulose ethers, sorbitan esters and polysorbates. Mixtures are operable. In at least one embodiment the emulsifying agent used is Polysorbate 80 (polyoxyethylene sorbitan mono-oleate) (e.g. Tween® 80). The emulsifying agent or agents, if present, might be present in certain embodiments in an amount of from greater than 0% to about 0.5% by weight of the coat composition. In at least one embodiment the emulsifying agent is present in an amount of from about 0.1% to about 0.3% by weight of the coat composition. In certain embodiments the emulsifying agent is present in an amount of from greater than about 0% to about 2% by dry weight of the coat. In other embodiments the emulsifying agent is present in an amount from about 0.1% to about 1% by dry weight of the coat. In still other embodiments the emulsifying agent is present in an amount from about 0.25% to about 0.75% by dry weight of the coat; for example, including about 0.30%, about 0.35%, about 0.40%, about 0.45%, about 0.50%, about 0.55%, about 0.60%, about 0.65%, and about 0.70% by dry weight of the coat. In certain embodiments the emulsifying agent is present in the coating formulation in an amount of from greater than about 0% to about 0.8% by dry weight of the tablet; in other embodiments in an amount of from greater than about 0% to about 0.4% by dry weight of the tablet; and in still other embodiments in an amount of from greater than about 0% to about 0.2% by dry weight of the tablet; for example, about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, and about 0.19% by dry weight of the tablet.

In certain embodiments, a coloring agent is utilized, such as in a coating described herein. In some instances, the colorants is a water-insoluble color (pigments). In some instances, pigments have certain advantages over water-soluble colors in that they tend to be more chemically stable towards light, provide better opacity and covering power, and optimize the impermeability of a given film to water vapor. Examples of suitable colorants include, but are not limited to iron oxide pigments, titanium dioxide, and Aluminum Lakes. Mixtures are operable. In at least one embodiment the pigment or colorant used is titanium dioxide. The pigment or colorant, if present, might be present in certain embodiments in an amount of from about 0.1% to about 10% by weight of the coat composition. In at least one embodiment the colorant is present in an amount of from about 0.1% to about 5% by weight of the coat composition. In at least one other embodiment the colorant is present in an amount of from about 0.1% to about 2% by weight of the coat composition. In certain embodiments the colorant is present in an amount of from greater than about 0% to about 20% by dry weight of the coat. In other embodiments the colorant is present in an amount from greater than about 0% to about 10% by dry weight of the coat. In still other embodiments the colorant is present in an amount from about 2.2% to about 6.2% by dry weight of the coat; for example, including about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, and about 6.1% by dry weight of the coat. In certain embodiments the colorant is present in the coating formulation in an amount of from greater than about 0% to about 8% by dry weight of the tablet; in other embodiments in an amount of from greater than about 0% to about 5% by dry weight of the tablet; and in still other embodiments in an amount of from greater than about 0% to about 1% by dry weight of the tablet; for example, including about 0.1%, about 0.2%, about 0.3%, about 0.4%, about 0.5%, about 0.6%, about 0.7%, about 0.8%, and about 0.9% by dry weight of the tablet.

In certain embodiments, a composition, formulation, core or coating described herein comprises a first and a second pharmaceutically acceptable excipient. In at least one embodiment the second pharmaceutically acceptable excipients (e.g. in the controlled release coating) comprises at least one of a neutral ester copolymer without any functional groups (e.g. Eudragit® NE30D, Eudragit® NE40D, Eudragit® NM30D, Kollicoat® EMM30D, or a mixture thereof), HPMC (e.g. Pharmacoat®606), talc (e.g. Talc 400), polyethylene glycol (e.g. polyethylene glycol 4000, polyethylene glycol 4600, polyethylene glycol 6000, polyethylene glycol 8000, polyethylene glycol 10000, polyethylene glycol 12000, polyethylene glycol 20000, polyethylene glycol 35000, or a mixture thereof), simethicone, Polysorbate 80, titanium dioxide, and mixtures thereof.

In at least one embodiment, a composition, formulation, core or coating described herein (e.g. a stable controlled release coating) hydrates when placed into water. In at least one embodiment the dosage form (e.g. that is coated with the controlled release coating) floats in water. In at least one embodiment, the (e.g. controlled release) dosage form, upon oral administration to a patient, provides controlled release of an effective amount of the active drug to at least one region of the patient's upper gastrointestinal tract (e.g. the stomach).

In some embodiments, any composition, formulation, core or coating described herein (e.g. controlled release coating) is formed by a process that does not involve the use of an organic solvent. In such embodiments the controlled release coating composition is aqueous-based and not solvent-based (termed "AQ" in certain examples of dosage forms coated with the aqueous-based controlled release coating). In some embodiments, the composition, formulation, core or coating described herein (e.g. controlled release coating) is formed by a process that are solvent based (e.g. "PharmaPASS™" composition).

In various embodiments, a coating composition is applied onto a core comprising an effective amount of the therapeutically active agent by a process, the process comprising atomizating (spraying) the coating composition (solution or suspension) onto a bed of the tablet cores. Some examples of equipment suitable for film coating include: ACCELA COTA® (Manesty Machines, Liverpool, UK), HI-COATER® (Freund Company, Japan), DRIACOATER™ (Driam Metallprodukt GmbH, Germany), HTF/150™ (GS, Italy), and IDA™ (Dumoulin, France). Examples of units that function on a fluidized-bed principle include: AEROMATIC™ (Fielder, Switzerland and UK) and GLATT AG™ (Switzerland). In at least one embodiment the apparatus used is the ACCELA COTA®.

In some instances, coating composition is delivered to the coating apparatus from a peristaltic pump at the desired rate and sprayed onto the rotating or fluidizing tablet cores. The tablet cores are pre-warmed to about 30° C. During the coating process, the product temperature range is maintained between about 25° C. and about 35° C. by adjusting the flow rate of the inlet and outlet air, temperature of the inlet air and spray rate. A single layer of the coating composition is applied and once spraying is complete, the coated tablet cores are dried between about 30° C. to about 40° C. for about 3 to about 5 minutes at a low pan speed and low air flow. The pan is readjusted to jog speed, and drying continued for about 12 to about 15 minutes.

In certain embodiments, coated tablet cores are placed onto a tray and cured (post coating thermal treatment) in an electrical or steam oven at a temperature above the temperature of the melting point of the polyethylene glycol or derivative thereof. In at least one embodiment the curing temperature is greater than the melting point of the polyethylene glycol or derivative thereof. In at least one embodiment the curing time is from about 2 to about 7 hours. The cured coated tablets are subsequently cooled to about room temperature.

In certain other embodiments, the coated tablet cores are placed onto a coating pan and cured at two-stages. During the first stage, the coated tablets are cured at a first curing temperature (for example, in certain embodiments from between about 50° C. to about 59° C.) for a period of time (for example, in certain embodiments from about 15 minutes to about 90 minutes; and in at least one embodiment for about 60 minutes). During the second stage, the coated tablets are cured at a second curing temperature that is at least equal to or greater than the melting point of the poly-glycol (for example, in certain embodiments from between about 60° C. to about 70° C.) for an additional period of time (for example, in certain embodiments from about 30 minutes to about 180 minutes; and in at least one embodiment for about 120 minutes). In at least one embodiment the two-stage curing of the coated tablets reduces non-functional defects on the tablet caused by the curing process. In at least one embodiment the two-stage curing process substantially eliminates non-functional defects on the tablet caused by the curing process. Non-functional defects on the dosage form caused by the curing process can include visual defects in the coating (e.g. poor color uniformity, and/or dull appearance), defects in the surface of the coating (e.g. roughness in the surface of the coating, and/or wrinkles in the coating), and sticking of the tablets to each other and/or to the coating pan. In addition, the reduced defects in color and smoothness of the tablets allows for improved printing of the tablets In some embodiments, the coating formulation is used to coat a variety of 5HT receptor agonist cores and might be adjusted to obtain a desired drug release profile. The length and time for the delay is controlled by rate of hydration and the thickness of the coat. The drug release rate subsequent to the delay is determined by the thickness and permeability of the hydrated coat. Thus, it is possible to regulate the rate of hydration and permeability of the coat so that the desired controlled release drug profile might be achieved. There is no preferred coat thickness, as this will depend on the drug being used in the core and also the controlled release profile desired. Other parameters in combination with the thickness of the coat include varying the concentrations of some of the ingredients of the stable coat composition and/or varying the curing temperature and length of curing the coated tablet cores. The skilled artisan will know which parameters or combination of parameters to change for a desired controlled release profile.

Immediate-Release Coating Formulations

In some embodiments, a composition or formulation (e.g. oral dosage form) provided herein comprises an immediate-release coating (e.g. providing immediate release of a 5HT receptor agonist). In some embodiments, the immediate-release coating comprises 5HT receptor agonist. In some embodiments, the immediate-release coating comprises more than one 5HT receptor agonist. In further embodiments, the immediate release coating comprises a pharmaceutically acceptable excipient. In some embodiments, the immediate release coating comprises a 5HT receptor agonist and an additional (e.g. pharmaceutically active) agent. In other embodiments, the immediate release coating comprises an additional (e.g. pharmaceutically active) agent, but not a 5HT receptor agonist. In some embodiments, the additional agent reduces, abates or eliminates adverse side effects associated with administration of the 5HT receptor agonist. In some embodiments, the additional agent that reduces, abates or eliminates adverse side effects associated with administration of the 5HT receptor agonist, is a 5HT receptor antagonist. In some embodiments, the additional agent in the immediate release coating is a 5HT receptor antagonist. In some embodiments, the additional agent in the immediate release coating is selected from the group selected from a stimulant, an antihistamine, an antiemetic, an antidepressant, an anti-inflammatory, a growth factor, a lithium compound, resveratrol, phosphatidylcholine, curcumin, magnesium, melatonin, pregnenolone, ginseng, tryptophan, lysergic acid diethylamide, or a 5HT receptor antagonist, and combinations thereof.

In some embodiments, an (e.g. therapeutically) effective amount of the immediate release active agent in immediate release form is coated onto the formulations described herein. For example, in some instances where the extended release of a 5HT receptor agonist or a pharmaceutically acceptable salt, solvate, metabolite, derivative, or prodrug thereof from the formulation is due to a controlled release coating, the immediate release layer of the additional agent would be overcoated on top of the controlled release coating. In some embodiments, the immediate release layer of the additional agent is coated onto the surface of substrates wherein the 5HT receptor agonist or a pharmaceutically acceptable salt, solvate, metabolite, derivative, or prodrug thereof is incorporated in a controlled release matrix. Where a plurality of the sustained release substrates comprising an effective unit dose of the 5HT receptor agonist or a pharmaceutically acceptable salt, solvate, metabolite, derivative, or prodrug thereof (e.g. multiparticulate systems including pellets, spheres, beads and the like) are incorporated into a hard gelatin capsule, the side effect-reducing compound might be incorporated into the gelatin capsule via inclusion of the sufficient amount of immediate release antihistamine or antiemetic as a powder or granulate within the capsule. Alternatively, the gelatin capsule itself is optionally coated with an immediate release layer of the additional agent.

A coating containing the immediate release comprising an additional agent such as antihistamine or antiemetic is optionally added to the outside of a (e.g. controlled release tablet core, such as comprising a 5HT receptor agonist described herein) to produce a final dosage form. Such a coating is prepared by any suitable method, such as being prepared by mixing compounds like promethazine with polyvinylpyrrolidone (PVP) 29/32 or hydroxypropyl methylcellulose (HPMC) and water/isopropyl alcohol and triethyl acetate. Such an immediate-release coating is optionally spray coated onto the tablet cores. The immediate-release coating is, in some instances, applied using a press-coating process with a blend consisting of 80% by weight promethazine and 20% by weight of lactose and hydroxypropyl methylcellulose type 2910.

In some embodiments, a composition or formulation provided herein (e.g. a formulation comprising an immediate release component and a controlled release component) is in the form of a bi-layered tablet, such as comprising a first layer and a second layer. In some embodiments, the first layer is an immediate release layer and/or the second layer is a controlled release layer. The first (or top) or immediate release layer comprises a first active agent, such as a 5HT receptor agonist and/or another agent, such as an agent selected from analgesics, antitussives, antihistamines, antiemetics, and stimulants. In some instances, the second or controlled release layer comprises a second drug, such as a 5HT receptor agonist. In some embodiments, the second drug is 5HT receptor agonist or a pharmaceutically acceptable salt, solvate, metabolite, derivative, or prodrug thereof. In some embodiments, the second drug is a formulation of 5HT receptor agonist or a pharmaceutically acceptable salt, solvate, metabolite, derivative, or prodrug thereof described herein. The bi-layered tablet provides a plasma concentration within the therapeutic range of the second drug over a period which is coextensive with at least about 70% of the period (i.e. 12 hours) within which the bi-layered tablet provides a plasma concentration within the therapeutic range of the first drug.

In some embodiments, a coating or layer (e.g. an immediate release or controlled release coating or layer) described herein comprises a stimulant. In some embodiments, the stimulant is selected from the group consisting of aminophylline, caffeine, dyphlline, oxitriphylline, theophylline, amphetamine, benzphetamine, dextroamphetamine, diethylpropion, mazindol, methamphetamine, methylphenidate, dexmethylphenidate, pemoline, sibutramine, modafinil, atomoxetine, phendimetrizine, phenteramine, adrafinil, phenylpropanolamine, psuedoephedrine, synephrine, amphetaminil, furfenorex, or a combination thereof.

In some embodiments, a coating or layer (e.g. an immediate release or controlled release coating or layer) comprises an antiemetic. In some embodiments, the antiemetic is selected from the group consisting of aprepitant, dronabinol, perphenazine, palonosetron, trimethobenzamide, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, cannabis, midazolam, lorazepam, hyoscine, dexamethasone, emetrol, propofol, or a combination thereof.

In some embodiments, a coating or layer (e.g. an immediate release or controlled release coating or layer) comprises an antihistamine. In some embodiments, the antihistamine is selected from the group consisting of 2-(m-fluorophenyl)-histamine, chlorpheniramine, mepyramine, terfenadine, astemizole, triprolidine, ethanolamines carbinoxamine, diphenhydramine, doxylamine, pyrilamine, tripelennamine, hydroxyzine, fexofenadine, brompheniramine chlorpheniramine, cyproheptadine, loratadine, cetirizine, dimaprit, impromidine, amthamine, cimetidine, ranitidine, nizatidine, famotidine, R-alpha-methylhistamine, imetit, immepip, thioperamide, iodophenpropit, clobenpropit, clobenpropit, imetit, clozapine, thioperamide, azelastine, brompheniramine, carbinoxamine, cetrizine, chlorpheniramine, clemastine, cyclizine, cyproheptadine, desloratidine, dimenhydrinate, diphenhydramine, emedastine, fexofenadine, ketotifen, levocabastine, loratadine, meclizine, olopatadine, phenindamine, promethazine, or a combination thereof.

In some embodiments, a coating or layer (e.g. immediate release or controlled release coating or layer) comprises an antidepressant. In some embodiments, the antidepressant is selected from the group consisting of Abilify (aripiprazole), Adapin (doxepin), Anafranil (clomipramine), Aplenzin (bupropion), Asendin (amoxapine), Aventyl HCl (nortriptyline), Celexa (citalopram), Cymbalta (duloxetine), Desyrel (trazodone), Effexor XR (venlafaxine), Emsam (selegiline), Etrafon (perphenazine and amitriptyline), Elavil (amitriptyline), Endep (amitriptyline), Fetzima (levomilnacipran), Khedezla (desvenlafaxine), Latuda (lurasidone), Lamictal (lamotrigine), Lexapro (escitalopram), Limbitrol (amitriptyline and chlordiazepoxide), Marplan (isocarboxazid), Nardil (phenelzine), Norpramin (desipramine), Oleptro (trazodone), Pamelor (nortriptyline), Parnate (tranylcypromine), Paxil (paroxetine), Pexeva (paroxetine), Prozac (fluoxetine), Pristiq (desvenlafaxine), Remeron (mirtazapine), Sarafem (fluoxetine), Seroquel XR (quetiapine), Serzone (nefazodone), Sinequan (doxepin), Surmontil (trimipramine), Symbyax (fluoxetine and the atypical antipsychotic drug olanzapine), Tofranil (imipramine), Triavil (perphenazine and amitriptyline), Trintelllix (vortioxetine), Viibryd (vilazodone), Vivactil (protriptyline), Wellbutrin (bupropion), Zoloft (sertraline), and Zyprexa (olanzapine).

In some embodiments, a coating or layer (e.g immediate release or controlled release coating or layer) comprises an anti-inflammatory. In some embodiments, the anti-inflammatory is selected from the group consisting of Aceclofenac, Aspirin, Celecoxib, Diclofenac, Diflunisal, Etodolac, Etoricoxib, Fenoprofen, Flurbiprofen, Ibuprofen, Indomethacin, Ketoprofen, Ketorolac, Lornoxicam, Loxoprofen, Mefenamic acid, Meloxicam, Montelukast, Nabumetone, Naproxen, Oxaprozin, Phenylbutazone, Piroxicam, Pranlukast, Salsalate, Sulindac, Tenoxicam, Tiaprofenic acid, Tolmetin, Valdecoxib, Zafirlukast, and Zileuton.

In some embodiments, a coating or layer (e.g. immediate release or controlled release coating or layer) comprises a growth factor. In some embodiments, the growth factor is selected from the group consisting of Platelet-Derived Growth Factor (PDGF), Transforming Growth Factor β (TGF-β), Epidermal Growth Factor (EGF), Vascular Endothelial Growth Factor (VEGF), Insulin-like Growth Factor (IGF), basic Fibroblast Growth Factor (bFGF).

In some embodiments, a coating or layer (e.g, immediate release layer) comprises a lithium compound, such as lithium carbonate, lithium citrate, or lithium orotate.

Controlled Release Matrix Formulations

In some embodiments, provided herein is a controlled release formulation or composition (e.g. an oral dosage form, or a core of an oral dosage form, or a layer of an oral dosage form, such as a tablet). In certain embodiments, the controlled release formulation or composition is coated or layered with another composition or formulation. In some instances, the controlled release formulation or composition is coated or layered with an immediate and/or controlled release coating or layer, such as described herein. In specific embodiments, a controlled release composition or formulation provided herein comprises a 5HT receptor agonist formulation comprising a controlled release matrix and (e.g, from about 0.1 to about 50 mg, about 10 mg to about 50 mg, about 0.1 mg to about 10 mg, about 0.2 mg to about 5 mg, or about 0.1 mg to about 2 mg, or about 1 mg to about 15 mg) of a 5HT receptor agonist or a pharmaceutically acceptable salt, solvate, metabolite, derivative, or prodrug thereof. In some embodiments, the controlled and/or immediate release coating or layer comprises a first active agent, such as a 5HT agonist and/or another agent, such as an agent selected from analgesics, antitussives, antihistamines, antiemetics, and stimulants. In certain embodiments, the coating (e.g. controlled release and/or immediate release coating) comprises any suitable agent, such as a stimulant, an antihistamine, an antiemetic, an antidepressant, an anti-inflammatory, a growth factor, a lithium compound, resveratrol, phosphatidylcholine, curcumin, magnesium, melatonin, pregnenolone, ginseng, tryptophan, lysergic acid diethylamide, and a 5HT receptor antagonist. In some embodiments, the coating (e.g. controlled release and/or immediate release coating) comprises a 5HT receptor agonist, such as described herein and a second agent, such as, by way of non-limiting example, a stimulant, an antihistamine, an antiemetic, an antidepressant, an anti-inflammatory, a growth factor, a lithium compound, resveratrol, phosphatidylcholine, curcumin, magnesium, melatonin, pregnenolone, ginseng, tryptophan, lysergic acid diethylamide, a 5HT receptor antagonist or any combination thereof.

Controlled Release Matrix

Active agents are released from a controlled release matrix in any suitable manner. Two exemplary mechanisms of release of the active agent(s) from a controlled release matrix include diffusion and/or degradation. Generally, diffusion occurs when the bioactive agent is released either through pores in the polymer matrix or by passing between polymer chains of the matrix. Typically, in a diffusion system, the bioactive agent might be dispersed throughout the matrix, or localized within a reservoir adjacent to or within the matrix. In some embodiments, the controlled release formulation utilizes a reservoir system, which typically comprises a reservoir of bioactive agent, for example, solid drug, dilute solution, or highly concentrated drug solution within a polymer matrix is surrounded by a controlled release material through which the bioactive agent is able to diffuse. Generally, in a degradable system, the bioactive agent is released as the matrix is degraded in vivo. In some instances, bioactive agent is released by a combination of such mechanisms. In some embodiment of the controlled release matrix described herein, the release of the bioactive agent is driven by a combination of both diffusion and degradation. In certain instances, the release rate is controlled by varying the drug to polymer ratio (e.g. a higher drug concentration tends to result in a faster rate of release) and/or by varying the chemistry of polymeric matrix (e.g. inclusion of polymers having a glass transition temperature (Tg) of less than about 40° C. or less than about 0° C. would tend to result in a faster elution rate than polymers with Tgs greater than 40° C., polymers that absorb water tend to elute drug more quickly than more hydrophobic polymers that do not absorb water). In some instances, these variables are controlled by the selection of materials used in the manufacturing process.

In some embodiments, the controlled release matrix is configured to release at least about 40% and up to about 60%, or at least 50% of the bioactive agent within 24 hours of administration. In another embodiment, the controlled release matrix is configured to release at least about 80% or up to about 100%, or at least 90% of the bioactive agent within 7 days after administration.

In some embodiments, the controlled release matrix is biodegradable. In some embodiments, the controlled release matrix includes a biodegradable polyester. Examples of biodegradable polyesters include, but are not limited to: polycaprolactone (PCL), polylactic acid (PLA), polyglycolide (PGA), and copolymers thereof, such as poly(lactic-co-glycolic acid) polymers (PLGA) and poly(glycolide-co-caprolactone) (PGC). PCL refers to a biodegradable polyester prepared by ring opening polymerization of &-caprolactone using a catalyst such as stannous octanoate. PCL has a melting point of about 60° C. and is degraded by hydrolysis of its ester linkages under physiological conditions. PLA is a biodegradable, thermoplastic polyester that can be produced by bacterial fermentation of renewable resources such as corn, starch or sugarcane and has a melting temperature between about 173° C. and about 178° C. PGA is a biodegradable, thermoplastic polyester prepared from glycolic acid by polycondensation or ring-opening polymerization. It has a melting point of between about 225° C. to about 230° C. A PLGA polymer refers to a biodegradable copolymer of lactic and glycolic acid formed by random ring-opening co-polymerization of monomers of glycolic acid and lactic acid. During polymerization, the monomeric units are linked together by ester linkages, thus yielding an aliphatic polyester. PLGAs are amorphous and have a glass transition temperature between about 40° C. and 60° C. In general, the PLGA copolymer has a weight average molecular weight between about 1000 Da to about 50,000 Da, or between about 5000 Da and 25,000 Da. The ratio of lactic acid to glycolic acid might vary. In general, and increase in the amount of lactic acid results in a polymer that degrades more slowly. An increase in glycolic acid results in a polymer that degrades more quickly. Additionally, an increase in glycolic acid tends to decrease the Tg and water penetration into the polymer, which can result in a faster release of compounds. In general, the ratio of lactic acid to glycolic acid is between about 100:0 to about 25:75, or between about 60:40 and 40:60, or about 50:50. Other suitable biodegradable polymers include, but are not limited to, poly(trimethylene carbonate) (PTMC), polydioxanone (PDO), poly(4-hydroxy butyrate) (PHB), and poly(butylene succinate) (PBS), poly(trimethylene carbonate) (PTMC), polydioxanone (PDO), poly(4-hydroxy butyrate) (PHB), and poly(butylene succinate) (PBS). In some embodiments, the polymeric material or polymer is biostable. Examples of biostable polymers include, but are not limited to polyurethanes, silicone rubbers, styrene-isobutylene-styrene block copolymers, ether-ester block copolymers (e.g. RTP 1500-40D from RTP Co.) and vinyl materials, including but not limited to poly(ethylene-co-vinyl acetate) (PEVA). In some embodiments, the controlled release matrix includes an elastomeric polymeric material that includes a copolymer with an elastomeric (or "soft") component and a non-elastomeric (or "hard") component. In another embodiment, the elastomeric polymeric material includes a polymeric blend having an elastomeric component and a non-elastomeric component. In some embodiments, the compliant polymer or polymeric material is thermoplastic. As used herein, the term "thermoplastic" refers to a polymer or polymeric material that can be softened by heat, hardened by cooling and then softened by heat over and over again. In general, thermoplastic materials are not cross-linked. However, in another embodiment, the compliant polymer or polymeric material might be cross-linked.

The bioactive agent is incorporated into the controlled release matrix, if used, using any suitable technique, such as any of various techniques known to the skilled artisan. In one embodiment, the bioactive agent is dispersed throughout the controlled release matrix. Techniques for preparing the controlled release matrix include, but are not limited to, melt extrusion processes, injection molding, or spray casting. In a typical melt extrusion process, a mixture that includes the polymeric material and bioactive agent is combined in an extruder, heated to a temperature at which the polymeric material melts and then discharged through an orifice of the desired cross-sectional shape. The extruded material is collected under controlled conditions (e.g. speed, temperature and humidity) to obtain a product with the desired dimensions. In one embodiment, the mass flow rate of the extrudate and the collection speed of the final extruded form might be controlled to achieve the desired physical dimensions. For example, if the final extruded form is a film, then the collection speed of the film might be increased relative to the mass flow rate of the extrudate to decrease the film thickness, and conversely to increase the film thickness. The extrudate is discharged through an orifice in the molten state, allowing elongation of the extrudate to its final dimension. The extrudate is subsequently cooled by exposure to ambient conditions, a chilled liquid or gas bath, or exposure to a temperature controlled surface such as a cooled roller in order to solidify the extrudate. In one embodiment, the melt extrusion process is used to form a film. In an alternate embodiment, the melt extrusion process is used to form pellets or beads that might be subsequently molded into the desired film or collar configuration. Some of the advantages of melt extrusion processes include: the absence of organic solvents and high throughput, continuous manufacturing. In general, the processing temperature is sufficient to melt the polymeric material without adversely affecting the biological activity of the bioactive agent. In general, the processing temperature is at least about 80° C. or about 100° C., and less than about 180° C., less than 160° C., or between about 110° C. and about 150° C. In some embodiments, the specific temperature is dependent on the melting and degradation temperatures of the polymeric materials and bioactive agent. Furthermore, melt-processing provides the ability for continuous operation, the ability to control operating parameters, and the ability to scale up manufacturing. In an alternate embodiment, an injection molding process is used. In a typical injection molding process, a mixture that includes the polymeric material and bioactive agent is fed into a vessel where it heated to a temperature sufficient to melt the polymeric material and then forced into a mold cavity where it cools and hardens to the configuration of the mold cavity. The conditions (e.g. temperature and pressure) will depend upon the material being molded. In one embodiment, the injection molding process is used to form a film or a collar. In yet another embodiment, a solvent casting technique is used. In a typical solvent casting process, the polymeric material and bioactive agent are combined with a suitable solvent to form a polymeric solution which is then cast on a substrate. The solvent is then removed to form a film, for example, by evaporation. In one embodiment, the solvent is removed under a vacuum (e.g. between about 15 in Hg and about 28 in Hg, depending upon the volatility of the solvent). In another embodiment, the solvent is removed at an elevated temperature (e.g. between about 30° C. and about 80° C.). In an alternate embodiment, the polymeric solution is applied to the substrate by a spray coating process. In a spray coating process, the polymeric solution is fed to the spray nozzle, for example and ultrasonic spray nozzle, at a controlled rate by a positive displacement pump. The spray nozzle and substrate are moved in relative motion to each other at controlled speed to achieve the desired coating thickness. The spray nozzle is mounted on a three-axis motion control system (x-y-z) which is capable of controlling the speed and position of the spray head relative to the substrate. In addition, if the substrate is a rolled film, it is traversed below the spray head by a roll to roll unwinding and winding apparatus. The coating width is controlled by moving the spray nozzle in a specified path across the width of the substrate. In addition, the height (z) of the spray nozzle above the substrate might be increased to achieve a wider coating width. In some instances, solvent forms a true solution with the components therein. In certain instances, the bioactive agent is soluble in the solvent or form a dispersion within the solvent. Any suitable solvents is optionally used, such as, by way of non-limiting example, alcohols (e.g. methanol, butanol, propanol and isopropanol), alkanes (e.g. halogenated or unhalogenated alkanes such as hexane, cyclohexane, methylene chloride and chloroform), amides (e.g. dimethylformamide), ethers (e.g. tetrahydrofuran (THF), dioxolane, and dioxane), ketones (e.g. methyl ethyl ketone, acetone), aromatic compounds (e.g. toluene and xylene), nitriles (e.g. acetonitrile) and esters (e.g. ethyl acetate). THF and chloroform have been found to be suitable solvents due to their excellent solvency for a variety of polymers and bioactive agents.

Mucoadhesive Agents

Often, mucoadhesive drug delivery systems interact with the mucus layer covering the mucosal epithelial surface to increase the residence time of the dosage form at the site of absorption. In some instances, a composition or formulation provided herein comprises a mucoadhesive agent, such as, by way of non-limiting example, a soluble PVP, a carbopol, a crosslinked poly(acrylic acid) (e.g. Carbopol 974P), a carbomer homopolymer, a carbomer copolymer, a water-swellable, but water-insoluble, fibrous, cross-linked carboxy-functional polymer, a mucoadhesive polysaccharide (e.g. a hydrophilic polysaccharide gum), one or more maltodextrin, alginate, a cross-linked aliginate gum gel, a water-dispersible polycarboxylated vinyl polymer. In some embodiments, the mucoadhesive agent is a carbopol. In some embodiments, the mucoadhesive agent is selected from, by way of non-limiting example, Carbopol 974P, Carbopol Ultrez 10, sodium alginate LF120 and sodium alginate H120L. In some embodiments, the mucoadhesive agent is a cellulose. In specific embodiments, the mucoadhesive agent is a carboxymethyl-cellulose (CMC), e.g. sodium carboxymethyl-cellulose (NaCMC), microcrystalline cellulose (MCC), or a combination thereof. In one non-limiting example, the mucoadhesive agent is a combination of MCC and CMC (e.g. Avicel RC-591). In some embodiments, the CMC/MCC combination (e.g. Avicel® RC-591) is present in the composition in an amount of about 1 mg/mL to about 150 mg/mL, 1 mg/mL to about 75 mg/mL, or about 5 mg/mL to about 40 mg/mL. In certain embodiments, the CMC/MCC mixed weight ratio is between about 1/99 and about 99/1, about 20/80 and about 5/95, or about 15/85 and about 10/90. In a specific embodiment, the CMC is NaCMC and the CMC/MCC mixed weight ratio is about 11/89.

In some embodiments, a mucoadhesive drug delivery system is a composition comprising both a CMC (e.g. a CMC/MCC mixture) and maltodextrin. In certain embodiments, the combination of a CMC (e.g. a CMC/MCC mixture) and maltodextrin provide an increased residence time on an afflicted or targeted surface of the mucosa (e.g. gastrointestinal tract), when compared to a composition having a similar amount of either the CMC (e.g. a CMC/MCC mixture) or maltodextrin alone.

In some embodiments, a pharmaceutical composition, formulation, and/or dosage form of a 5HT receptor agonist or a pharmaceutically acceptable salt, solvate, metabolite, derivative, or prodrug thereof disclosed herein, comprises a mucoadhesive agent. In some embodiments, the mucoadhesive agent comprises one or more maltodextrin. In various aspects, the physical characteristics of maltodextrins vary depending, e.g. on the dextrose equivalent of the specific maltodextrin. In some embodiments, the dextrose equivalent of a specific maltodextrin might affect the viscosity, hygroscopicity, sweetness, humectancy, plasticity, solubility and or mucoadhesiveness of the maltodextrin. In some embodiments, a maltodextrin is selected based on the specific character that is desired to be imparted upon the pharmaceutical composition described herein. In some embodiments, a maltodextrin is selected that increases the mucoadhesive character of a composition described herein without substantially increasing the viscosity of the composition (e.g. compared to an otherwise identical composition lacking the maltodextrin). In some embodiments, the oral pharmaceutical composition comprises a second maltodextrin that increases the viscosity of the oral pharmaceutical composition (e.g. compared to an otherwise identical composition lacking the second maltodextrin). In some embodiments, the second maltodextrin that does not substantially affect the mucoadhesive characteristic of the pharmaceutical composition (e.g. compared to an otherwise identical composition lacking the second maltodextrin).

In some embodiments, the mucoadhesive agent does not substantially increase the viscosity of the oral pharmaceutical composition (e.g. compared to an otherwise identical composition lacking the mucoadhesive agent). In some embodiments, the mucoadhesive agent is chosen for its mucoadhesive properties (e.g. its ability to impart mucoadhesive character upon the oral pharmaceutical composition).

In some embodiments, a mucoadhesive agent utilized in an oral pharmaceutical composition described herein imparts an increased viscosity upon the oral pharmaceutical composition (e.g. compared to an otherwise identical composition lacking the mucoadhesive agent). In other embodiments, the mucoadhesive agent does not substantially increase the viscosity of the oral pharmaceutical composition (e.g. compared to an otherwise identical composition lacking the mucoadhesive agent).

In some embodiments, at least one mucoadhesive agent is chosen for and used in the pharmaceutical composition so the addition of the at least one mucoadhesive agent does not substantially increase the viscosity of the resulting oral pharmaceutical composition (e.g. compared to an otherwise identical composition lacking the mucoadhesive agent).

In some embodiments, at least two mucoadhesive agents are chosen for and used in the pharmaceutical composition so the addition of the at least two mucoadhesive agents do not substantially increase the viscosity of the resulting oral pharmaceutical composition (e.g. compared to an otherwise identical composition lacking the mucoadhesive agents). In some embodiments, at least one mucoadhesive agent, if taken alone in the pharmaceutical composition would increase the viscosity of the pharmaceutical composition, but taken together with all components in the pharmaceutical composition, does not substantially increase the viscosity of the resulting oral pharmaceutical composition (e.g. compared to an otherwise identical composition lacking the at least one mucoadhesive agent).

In some embodiments, the viscosity of the composition is at least about 2 centipoise (cP), at least about 5 cP, at least about 10 cP, at least about 20 cP, at least about 25 cP, at least about 35 cP, at least about 40 cP, at least about 50 cP, at least about 200 cP, or at least about 225 cP. In some embodiments, the viscosity of the composition is at least about 100 cP. In certain embodiments, the viscosity of the composition, measured at 25° C., is about 50 cP to about 250,000 cP, about 50 cP to about 70,000 cP, about 50 cP to about 25,000 cP, about 50 cP to about 10,000 cP, about 50 cP to about 3,000 cP, or about 50 cP to about 2,000 cP. In one aspect, the viscosity of the composition, as measured at 25° C., is from about 25 centipoise (cP) to about 800 cP, about 50 cP to about 800, or about 300 cP to about 800 cP (e.g. measured by a Brookfield viscometer). In another aspect, the viscosity of the composition might range from about 100 cP to about 200 cP, about 200 cP to about 300 cP, about 250 cP to about 600 cP or about 400 cP to about 600 cP. In specific embodiments, the viscosity of the formulation is about 30 cP, about 100 cP, about 200 cP, about 300 cP, about 400 cP, about 500 cP, or about 250,000 cP (e.g. as measured with a Brookfield viscometer at 25° C.).

In certain embodiments, provided herein is a composition having a viscosity that is at least about 2 centipoise (cP), at least about 5 cP, at least about 10 cP, at least about 20 cP, at least about 25 cP, at least about 30 cP, at least about 35 cP, at least about 40 cP, at least about 50 cP, at least about 200 cP, at least about 225 cP, at least about 250 cP, at least about 300 cP, or at least about 400 cP. In some embodiments, the viscosity of the composition under such conditions is about 50 cP to about 250,000 cP, about 50 cP to about 70,000 cP, about 50 cP to about 25,000 cP, about 50 cP to about 10,000 cP, about 50 cP to about 3,000 cP, about 50 cP to about 2,000 cP, about 250 cP to about 250,000 cP, about 250 cP to about 70,000 cP, about 250 cP to about 25,000 cP, about 250 cP to about 10,000 cP, about 250 cP to about 3,000 cP, or about 250 cP to about 2,000 cP. In one aspect, the viscosity of the composition, as measured at 25 degrees Celsius, is from about 25 centipoise (cP) to about 800 cP, about 50 cP to about 800, or about 300 cP to about 800 cP (e.g. measured by a Brookfield viscometer). In another aspect, the viscosity of the composition under such conditions might range from about 100 cP to about 200 cP, about 200 cP to about 300 cP, about 250 cP to about 600 cP or about 400 cP to about 600 cP. In specific embodiments, the viscosity of the formulation measured under such conditions is about 30 cP, about 40 cP, about 100 cP, about 200 cP, about 300 cP, about 400 cP, about 500 cP, or about 250,000 cP.

In one non-limiting example, a mucoadhesive agent can be, by way of non-limiting example, at least two particulate components selected from titanium dioxide, silicon dioxide, and clay. In some embodiments, when the composition is not further diluted with any liquid prior to administration, the level of silicon dioxide is from about 3% to about 15%, by weight of the composition. In certain embodiments, silicon dioxide is selected from, by way of non-limiting example, fumed silicon dioxide, precipitated silicon dioxide, coacervated silicon dioxide, gel silicon dioxide, and mixtures thereof. In some embodiments, clay is selected from, by way of non-limiting example, kaolin minerals, serpentine minerals, smectites, illite or mixtures thereof. In certain embodiments, clay is selected from, by way of non-limiting example, laponite, bentonite, hectorite, saponite, montmorillonites or mixtures thereof.

In some embodiments, the mucoadhesive agent is selected in an amount sufficient to cause the 5HT receptor agonist or a pharmaceutically acceptable salt, solvate, metabolite, derivative, or prodrug thereof containing pharmaceutical composition to adhere to or resides upon a surface of the mucous membrane for 5 seconds, 10 seconds, 15 seconds, 30 seconds, 45 seconds, or 1 minute following application to the surface of the mucous membrane. In certain embodiments, the mucoadhesive agent is selected in an amount sufficient to cause the 5HT receptor agonist or a pharmaceutically acceptable salt, solvate, metabolite, derivative, or prodrug thereof containing composition to adhere to or reside upon the surface of the mucous membrane for 1.5, 2, 3, 4, 5, 6, 7, 8, 9, 10, 15, 20, 25, 30, 35, 40, 45, 50, 55 or 60 minutes after application to the surface of the mucous membrane. In some embodiments, the amount of 5HT receptor agonist or a pharmaceutically acceptable salt, solvate, metabolite, derivative, or prodrug thereof containing composition that adheres to a surface of the mucous membrane for 5 seconds, 10 seconds, or 0.25, 0.5, 0.75, 1, 1.5, 2, 3, 4, 5, 6, 7, 8, 9, 10, 15, 20, 25, 30, 35, 40, 45, 50, 55 or 60 minutes is at least 1%, at least 2%, at least 3%, at least 4%, at least 5%, at least 6%, at least 7%, at least 8%, at least 9%, at least 10%, at least 15%, at least 20%, at least 30%, at least 40%, at least 50%, at least 60%, at least 70%, at least 80%, at least 90% or at least 95% by weight after administration to the surface of the mucous membrane. In specific embodiments, at least 50% of the pharmaceutical composition adheres to or resides upon the surface of the mucous membrane for at least 1 or at least 15 minutes following application to the surface of the mucous membrane.

Optional viscosity-enhancing excipients used in pharmaceutical compositions described herein include, by way of non-limiting example, a crosslinked poly(acrylic acid) (e.g. Carbopol 974P), glycerin, a carbomer homopolymer, a carbomer copolymer, acacia (gum arabic), agar, aluminum magnesium silicate, sodium alginate, sodium stearate, bladderwrack, bentonite, carbomer, carrageenan, Carbopol, cellulose, microcrystalline cellulose (MCC), ceratonia, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, polyethylene glycol (e.g. PEG 200-4500) gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose, carboxymethyl-cellulose (CMC) (including, e.g. sodium carboxymethyl-cellulose (NaCMC)), silicon dioxide, PVP (Povidone), Splenda® (dextrose, maltodextrin and sucralose) or combinations thereof.

Excipients

In certain embodiments, one or more compositions or formulations of a 5HT receptor agonist or a pharmaceutically acceptable salt, solvate, metabolite, derivative, or prodrug thereof described above further comprise an excipient. In some embodiments, aqueous suspensions of the pharmaceutical composition disclosed herein contain pharmaceutically acceptable excipients, such as a suspending agent (e.g. methyl cellulose), a wetting agent (e.g. lecithin, lysolecithin and/or a long-chain fatty alcohol), as well as coloring agents, preservatives, flavoring agents, and the like.

Pharmaceutical preparations for oral use are obtained using any suitable process, such as by combining active with a solid excipient, optionally grinding a resulting mixture, and processing the mixture of granules, after adding suitable auxiliaries, if desired, to obtain tablets or dragee cores. Suitable excipients are, in some instances, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or PVP. If desired, disintegrating agents might be added, such as the cross-linked PVP, agar, or alginic acid or a salt thereof such as sodium alginate. The active compounds might also be formulated as a sustained release preparation.

Pharmaceutical preparations that are optionally used orally include push-fit capsules made of gelatin, as well as soft, sealed capsules made of gelatin and a plasticizer, such as glycerol or sorbitol. The push-fit capsules might contain the active ingredients in admixture with filler such as lactose, binders such as starches, and/or lubricants such as talc or magnesium stearate and, optionally, stabilizers. In soft capsules, the active compounds might be dissolved or suspended in suitable liquids, such as fatty oils, liquid paraffin, or liquid polyethylene glycols. In addition, stabilizers might be added. All formulations for oral administration should be in dosages suitable for administration.

For injection, the pharmaceutical compositions disclosed herein are optionally formulated in aqueous solutions, preferably in physiologically compatible buffers such as Hank's solution, Ringer's solution, or physiological saline buffer. Such compositions might also include one or more excipients, for example, preservatives, solubilizers, fillers, lubricants, stabilizers, albumin, and the like. Methods of formulation are known in the art, for example, as disclosed in Remington's Pharmaceutical Sciences, latest edition, Mack Publishing Co., Easton, Pa. These pharmaceutical compositions might also be formulated for transmucosal administration, buccal administration, for administration by inhalation, for parental administration, for transdermal administration, and rectal administration.

In addition to the disclosed formulations, the pharmaceutical compositions are optionally formulated as a depot preparation. Such long acting formulations might be administered by implantation or transcutaneous delivery (for example subcutaneously or intramuscularly), intramuscular injection or use of a transdermal patch. Thus, for example, the pharmaceutical compositions are optionally formulated with suitable polymeric or hydrophobic materials (for example as an emulsion in an acceptable oil) or ion exchange resins, or as sparingly soluble derivatives, for example, as a sparingly soluble salt.

In some embodiments, the pharmaceutical formulations include, but are not limited to, aqueous liquid dispersions, self-emulsifying dispersions, solid solutions, liposomal dispersions, aerosols, solid dosage forms, powders, immediate-release formulations, controlled release formulations, fast melt formulations, tablets, capsules, pills, delayed release formulations, extended release formulations, pulsatile release formulations, multiparticulate formulations (e.g. nanoparticle formulations), and mixed immediate and controlled release formulations.

In some instances, the pharmaceutical formulation includes multiparticulate formulations. In some instances, the pharmaceutical formulation includes nanoparticle formulations. In some instances, nanoparticles comprise cyclodextrins or lipids. In some cases, nanoparticles comprise solid lipid nanoparticles, polymeric nanoparticles, self-emulsifying nanoparticles, liposomes, microemulsions, or micellar solutions.

In some instances, a nanoparticle includes a core or a core and a shell, as in a core-shell nanoparticle.

In some instances, a nanoparticle is further coated with molecules for attachment of functional elements. In some instances, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, ovalbumin or dextrin or cyclodextrin.

In some cases, a nanoparticle has at least one dimension of less than about 500 nm, 400 nm, 300 nm, 200 nm, or 100 nm.

In some embodiments, the pharmaceutical formulations include a carrier or carrier materials selected on the basis of compatibility with the composition disclosed herein, and the release profile properties of the desired dosage form. Pharmaceutically compatible carrier materials include, but are not limited to, acacia, gelatin, colloidal silicon dioxide, calcium glycerophosphate, calcium lactate, maltodextrin, glycerin, magnesium silicate, PVP, cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and any combination thereof. See, e.g. *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

In some instances, the pharmaceutical formulations further include pH adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some instances, the pharmaceutical formulations include binder which are used to hold a 5HT receptor agonist or a pharmaceutically acceptable salt, solvate, metabolite, derivative, or prodrug thereof and inactive ingredients together in a cohesive mix. Suitable binders include, but are not limited to, carboxymethylcellulose, methylcellulose (e.g. Methocel®), hydroxypropylmethylcellulose (e.g.

Hypromellose USP Pharmacoat-603, hydroxypropylmethylcellulose acetate stearate (Aqoate HS-LF and HS), hydroxyethylcellulose, hydroxypropylcellulose (e.g. Klucel®), ethylcellulose (e.g. Ethocel®), and microcrystalline cellulose (e.g. Avicel®), microcrystalline dextrose, amylose, magnesium aluminum silicate, polysaccharide acids, bentonites, gelatin, PVP/vinyl acetate copolymer, crospovidone, povidone, starch, pregelatinized starch, tragacanth, dextrin, a sugar, such as sucrose (e.g. Dipac®), glucose, dextrose, molasses, mannitol, sorbitol, xylitol (e.g. Xylitab®), lactose, a natural or synthetic gum such as acacia, tragacanth, ghatti gum, mucilage of isapol husks, starch, PVP (e.g. Povidone® CL, Kollidon® CL, Polyplasdone® XL-10, and Povidone® K-12), larch arabogalactan, Veegum®, polyethylene glycol, waxes, sodium alginate, and any combination thereof.

In some instances, the pharmaceutical formulations further include diluent which are used to stabilize a 5HT receptor agonist or a pharmaceutically acceptable salt, solvate, metabolite, derivative, or prodrug thereof because they provide a more stable environment. Salts dissolved in buffered solutions (which also provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds include e.g. lactose, starch, mannitol, sorbitol, dextrose, microcrystalline cellulose such as Avicel®; dibasic calcium phosphate, dicalcium phosphate dihydrate, tricalcium phosphate, calcium phosphate; anhydrous lactose, spray-dried lactose; pregelatinized starch, compressible sugar, such as Di-Pack (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and any combination thereof.

In some cases, the pharmaceutical formulations include disintegration agents or disintegrants to facilitate the breakup or disintegration of a substance. The term "disintegrate" includes both the dissolution and dispersion of the dosage form when contacted with gastrointestinal fluid. Examples of disintegration agents include a starch, e.g. a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g. Avicel®, Avicel® PH101, Avicel® PH102, Avicel® PH105, Elcema® P100, Emcocel®, Vivacel®, Ming Tia®, and Solka-Flock, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked PVP, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and any combination thereof.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and any combination thereof.

Lubricants and glidants are also optionally included in the pharmaceutical formulations disclosed herein for preventing, reducing or inhibiting adhesion or friction of materials. Exemplary lubricants include, e.g. stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g. PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and any combination thereof.

Plasticizers include compounds used to soften the microencapsulation material or film coatings to make them less brittle. Suitable plasticizers include, e.g. PEGs such as PEG 300, PEG 400, PEG 600, PEG 1450, PEG 3350, and PEG 800, stearic acid, propylene glycol, oleic acid, triethyl cellulose and triacetin. Plasticizers also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, PVP, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and any combination thereof.

Stabilizers include compounds such as any antioxidation agents, buffers, acids, preservatives and any combination thereof.

Suspending agents include compounds such as PVP, e.g. PVP K12, PVP K17, PVP K25, or PVP K30, vinyl pyrrolidone/vinyl acetate copolymer (S630), PEG, e.g. the PEG has a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, Polysorbate 80, hydroxyethylcellulose, sodium alginate, gums, such as, e.g. gum tragacanth and gum acacia, guar gum, xanthans, including xanthan gum, sugars, cellulosics, such as, e.g. sodium carboxymethylcellulose, methylcellulose, sodium carboxymethylcellulose, hydroxypropylmethylcellulose, hydroxyethylcellulose, Polysorbate 80, sodium alginate, polyethoxylated sorbitan monolaurate, polyethoxylated sorbitan monolaurate, povidone, and any combination thereof.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g. Pluronic® (BASF), and any combination thereof. Additional surfactants include polyoxyethylene fatty acid glycerides and vegetable oils, e.g. polyoxyethylene (60)

hydrogenated castor oil; and polyoxyethylene alkylethers and alkylphenyl ethers, e.g. octoxynol 10, octoxynol 40. Sometimes, surfactants are included to enhance physical stability or for other purposes.

Viscosity enhancing agents include, e.g. methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts, and any combination thereof.

Antifoaming agents are chemical additive that reduces and hinders the formation of foam in the preparation of an oral liquid formulation. The terms antifoaming agent and defoamer are often used interchangeably. Commonly used agents are insoluble oils, polydimethylsiloxanes (e.g. simethicone) and other silicones, certain alcohols, stearates and glycols. The additive is used to prevent formation of foam or is added to break foam already formed. Antifoaming agents reduce foaming in the preparation of an oral liquid formulation which might result in coagulation of aqueous dispersions. In some embodiments, the 5HT receptor agonist compositions described herein comprise an antifoaming agent. In some embodiments, the antifoaming agent is simethicone.

In some embodiments, there is a considerable overlap between excipients used in the pharmaceutical compositions, formulations, and dosage forms of a 5HT receptor agonist or a pharmaceutically acceptable salt, solvate, metabolite, derivative, or prodrug thereof described herein. Thus, the above-listed additives should be taken as merely exemplary, and not limiting, of the types of additives that might be included in solid dosage forms of the pharmaceutical compositions described herein.

Methods of Pharmaceutical Formulations and Routes of Administration

In some embodiments, 5HT receptor agonists or pharmaceutical compositions or formulations described herein are administered to a subject by multiple administration routes, including but not limited to, oral, parenteral (e.g. intravenous, subcutaneous, intramuscular), intranasal, inhalation, buccal, topical, rectal, or transdermal administration routes. In some embodiments, pharmaceutical compositions described herein, which include 5HT receptor agonist, or pharmaceutically acceptable salt, solvate, metabolite, derivative, or prodrug thereof, are formulated into any suitable dosage form, including but not limited to, emulsions suitable for injection, nanosuspensions suitable for injection, aqueous oral dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulates formulations, and mixed immediate-release and controlled release formulations.

In some embodiments, the pharmaceutical composition for oral use is a tablet, (including a suspension tablet, a fast melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g. capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In some embodiments, the pharmaceutical composition for oral use is a solid dosage form, e.g. tablets, effervescent tablets, and capsules. In some embodiments, the solid dosage forms are prepared by mixing particles of 5HT receptor agonist, or pharmaceutically acceptable salt, solvate, metabolite, derivative, or prodrug thereof, with one or more pharmaceutical excipients to form a bulk blend composition. When referring to these bulk blend compositions as homogeneous, it is meant that the particles of 5HT receptor agonist, or pharmaceutically acceptable salt, solvate, metabolite, derivative, or prodrug thereof, are dispersed evenly throughout the composition so that the composition might be subdivided into equally effective unit dosage forms, such as tablets, pills, and capsules. The individual unit dosages might also include film coatings, which disintegrate upon oral ingestion or upon contact with diluent.

For oral administration, the pharmaceutical compositions disclosed herein are, in some instances, formulated readily by combining the active compound(s) with pharmaceutically acceptable carriers well known in the art. Such carriers enable the compositions disclosed herein to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations might comprise pharmaceutically acceptable carriers including solid diluents or fillers, sterile aqueous media and various non-toxic organic solvents. Generally, the compositions disclosed herein will be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Dosage

In some embodiments, the amount of 5HT receptor agonist, or pharmaceutically acceptable salt, solvate, metabolite, derivative, or prodrug thereof used in a pharmaceutical composition is about 1 mg/ml to about 30 mg/ml. In some embodiments, the amount of 5HT receptor agonist, or pharmaceutically acceptable salt, solvate, metabolite, derivative, or prodrug thereof used in a pharmaceutical composition is about 0.1 mg/ml to about 10 mg/ml. In some embodiments, the amount of 5HT receptor agonist, or pharmaceutically acceptable salt, solvate, metabolite, derivative, or prodrug thereof used in a pharmaceutical composition is about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2 mg/ml, about 2.1 mg/ml, about 2.2 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, about 3 mg/ml, about 3.1 mg/ml, about 3.2 mg/ml, about 3.3 mg/ml, about 3.4 mg/ml, about 3.5 mg/ml, about 3.6 mg/ml, about 3.7 mg/ml, about 3.8 mg/ml, about 3.9 mg/ml, about 4 mg/ml, about 4.1 mg/ml, about 4.2 mg/ml, about 4.3 mg/ml, about 4.4 mg/ml, about 4.5 mg/ml, about 4.6 mg/ml, about 4.7 mg/ml, about 4.8 mg/ml, about 4.9 mg/ml, about 5 mg/ml, about 5.1 mg/ml, about 5.2 mg/ml, about 5.3 mg/ml, about 5.4 mg/ml, about 5.5 mg/ml, about 5.6 mg/ml, about 5.7 mg/ml, about 5.8 mg/ml, about 5.9 mg/ml, about 6 mg/ml, about 6.1 mg/ml, about 6.2 mg/ml, about 6.3 mg/ml, about 6.4 mg/ml, about 6.5 mg/ml, about 6.6 mg/ml, about 6.7 mg/ml, about 6.8 mg/ml, about 6.9 mg/ml, about 7 mg/ml, about 7.1 mg/ml, about 7.2 mg/ml, about 7.3 mg/ml, about 7.4 mg/ml, about 7.5 mg/ml, about 7.6 mg/ml, about 7.7 mg/ml, about 7.8 mg/ml, about 7.9 mg/ml, about 8 mg/ml, about 8.1 mg/ml, about 8.2 mg/ml, about 8.3 mg/ml, about 8.4 mg/ml, about 8.5 mg/ml, about 8.6 mg/ml, about 8.7 mg/ml, about 8.8 mg/ml, about 8.9 mg/ml, about 9 mg/ml, about 9.1 mg/ml, about 9.2 mg/ml, about 9.3 mg/ml, about 9.4 mg/ml, about 9.5 mg/ml, about 9.6 mg/ml, about 9.7 mg/ml, about 9.8 mg/ml, about 9.9 mg/ml, about 10 mg/ml, about 10.1 mg/ml, about 10.2 mg/ml, about 10.3 mg/ml, about 10.4 mg/ml, about 10.5 mg/ml, about 10.6 mg/ml, about 10.7 mg/ml, about 10.8 mg/ml, about 10.9 mg/ml, about 11 mg/ml, about 11.1 mg/ml, about 11.2 mg/ml, about 11.3 mg/ml, about 11.4 mg/ml, about 11.5 mg/ml, about 11.6 mg/ml, about 11.7 mg/ml, about 11.8 mg/ml, about 11.9 mg/ml, about 12 mg/ml, about 12.1 mg/ml, about 12.2 mg/ml, about 12.3 mg/ml, about 12.4 mg/ml, about 12.5 mg/ml, about 12.6 mg/ml, about 12.7 mg/ml, about 12.8 mg/ml, about 12.9 mg/ml, about 13 mg/ml, about 13.1 mg/ml, about 13.2 mg/ml, about 13.3 mg/ml, about 13.4 mg/ml, about 13.5 mg/ml, about 13.6 mg/ml, about 13.7 mg/ml, about 13.8 mg/ml, about 13.9 mg/ml, about 14 mg/ml, about 14.1 mg/ml, about 14.2 mg/ml, about 14.3 mg/ml, about 14.4 mg/ml, about 14.5 mg/ml, about 14.6 mg/ml, about 14.7 mg/ml, about 14.8 mg/ml, about 14.9 mg/ml, about 15 mg/ml, about 15.5 mg/ml, about 16 mg/ml, about 16.5 mg/ml, about 17 mg/ml, about 17.5 mg/ml, about 18 mg/ml, about 18.5 mg/ml, about 19 mg/ml, about 19.5 mg/ml, about 20 mg/ml, about 21 mg/ml, about 22 mg/ml, about 23 mg/ml, about 24 mg/ml, about 25 mg/ml, about 27.5 mg/ml, about 30 mg/ml.

In some embodiments, the amount of a 5HT receptor agonist or a pharmaceutically acceptable salt, solvate, metabolite, derivative, or prodrug thereof in the pharmaceutical composition corresponds to about 0.8 mg/ml to about 24 mg/ml of the 5HT receptor agonist or a pharmaceutically acceptable salt, solvate, metabolite, derivative, or prodrug thereof. In other embodiments, the amount of 5HT receptor agonist, or pharmaceutically acceptable salt, solvate, metabolite, derivative, or prodrug thereof in the pharmaceutical composition corresponds to about 0.8 mg/ml, about 0.9 mg/ml, about 1 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2 mg/ml, about 2.1 mg/ml, about 2.2 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, about 3 mg/ml, about 3.1 mg/ml, about 3.2 mg/ml, about 3.3 mg/ml, about 3.4 mg/ml, about 3.5 mg/ml, about 3.6 mg/ml, about 3.7 mg/ml, about 3.8 mg/ml, about 3.9 mg/ml, about 4 mg/ml, about 4.1 mg/ml, about 4.2 mg/ml, about 4.3 mg/ml, about 4.4 mg/ml, about 4.5 mg/ml, about 4.6 mg/ml, about 4.7 mg/ml, about 4.8 mg/ml, about 4.9 mg/ml, about 5 mg/ml, about 5.1 mg/ml, about 5.2 mg/ml, about 5.3 mg/ml, about 5.4 mg/ml, about 5.5 mg/ml, about 5.6 mg/ml, about 5.7 mg/ml, about 5.8 mg/ml, about 5.9 mg/ml, about 6 mg/ml, about 6.1 mg/ml, about 6.2 mg/ml, about 6.3 mg/ml, about 6.4 mg/ml, about 6.5 mg/ml, about 6.6 mg/ml, about 6.7 mg/ml, about 6.8 mg/ml, about 6.9 mg/ml, about 7 mg/ml, about 7.1 mg/ml, about 7.2 mg/ml, about 7.3 mg/ml, about 7.4 mg/ml, about 7.5 mg/ml, about 7.6 mg/ml, about 7.7 mg/ml, about 7.8 mg/ml, about 7.9 mg/ml, about 8 mg/ml, about 8.1 mg/ml, about 8.2 mg/ml, about 8.3 mg/ml, about 8.4 mg/ml, about 8.5 mg/ml, about 8.6 mg/ml, about 8.7 mg/ml, about 8.8 mg/ml, about 8.9 mg/ml, about 9 mg/ml, about 9.1 mg/ml, about 9.2 mg/ml, about 9.3 mg/ml, about 9.4 mg/ml, about 9.5 mg/ml, about 96 mg/ml, about 9.7 mg/ml, about 9.8 mg/ml, about 9.9 mg/ml, about 10 mg/ml, about 10.1 mg/ml, about 10.2 mg/ml, about 10.3 mg/ml, about 10.4 mg/ml, about 10.5 mg/ml, about 10.6 mg/ml, about 10.7 mg/ml, about 10.8 mg/ml, about 10.9 mg/ml, about 11 mg/ml, about 11.1 mg/ml, about 11.2 mg/ml, about 11.3 mg/ml, about 11.4 mg/ml, about 11.5 mg/ml, about 11.6 mg/ml, about 11.7 mg/ml, about 11.8 mg/ml, about 11.9 mg/ml, about 12 mg/ml, about 12.1 mg/ml, about 12.2 mg/ml, about 12.3 mg/ml, about 12.4 mg/ml, about 12.5 mg/ml, about 12.6 mg/ml, about 12.7 mg/ml, about 12.8 mg/ml, about 12.9 mg/ml, about 13 mg/ml, about 13.1 mg/ml, about 13.2 mg/ml, about 13.3 mg/ml, about 13.4 mg/ml, about 13.5 mg/ml, about 13.6 mg/ml, about 13.7 mg/ml, about 13.8 mg/ml, about 13.9 mg/ml, about 14 mg/ml, about 14.1 mg/ml, about 14.2 mg/ml, about 14.3 mg/ml, about 14.4 mg/ml, about 14.5 mg/ml, about 14.6 mg/ml, about 14.7 mg/ml, about 14.8 mg/ml, about 14.9 mg/ml, about 15 mg/ml, about 15.5 mg/ml, about 16 mg/ml, about 16.5 mg/ml, about 17 mg/ml, about 17.5 mg/ml, about 18 mg/ml, about 18.5 mg/ml, about 19 mg/ml, about 19.5 mg/ml, about 20 mg/ml, about 21 mg/ml, about 22 mg/ml, about 23 mg/ml, or about 24 mg/ml of a 5HT receptor agonist or a pharmaceutically acceptable salt, solvate, metabolite, derivative, or prodrug thereof.

In some embodiments, the amount of 5HT receptor agonist, or pharmaceutically acceptable salt, solvate, metabolite, derivative, or prodrug thereof used in a pharmaceutical composition is about 0.001 mg to about 20 mg. In some embodiments, the amount of 5HT receptor agonist, or pharmaceutically acceptable salt, solvate, metabolite, derivative, or prodrug thereof used in a pharmaceutical composition is about 0.005 mg to about 10 mg. In some embodiments, the amount of 5HT receptor agonist, or pharmaceutically acceptable salt, solvate, metabolite, derivative, or prodrug thereof used in a pharmaceutical composition is about 0.01 mg to about 5 mg. In some embodiments, the amount of 5HT receptor agonist, or pharmaceutically acceptable salt, solvate, metabolite, derivative, or prodrug thereof used in a pharmaceutical composition is about 0.05 mg to about 2.5 mg. In other embodiments, the amount of 5HT receptor agonist, or pharmaceutically acceptable salt, solvate, metabolite, derivative, or prodrug thereof in the pharmaceutical composition corresponds to about 0.001 mg, about 0.005 mg, about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.11 mg, about 0.12 mg, about 0.15 mg, about 0.17 mg, about 0.2 mg, about 0.23 mg, about 0.25 mg, about 0.28 mg, about 0.3 mg, about 0.33 mg, about 0.35 mg, about 0.37 mg, about 0.4 mg, about 0.43 mg, about 0.45 mg, about 0.47 mg, about 0.5 mg, about 0.53 mg, about 0.55 mg, about 0.57 mg, about 0.6 mg, about 0.63 mg, about 0.65 mg, about 0.67 mg, about 0.7 mg, about 0.73 mg, about 0.75 mg, about 0.78 mg, about 0.8 mg, about 0.83 mg, about 0.85 mg, about 0.87 mg, about 0.9 mg, about 0.95 mg, about 1 mg, about 1.1 mg, about 1.2 mg, about 1.3 mg, about 1.4 mg, about 1.5 mg, about 1.6 mg, about 1.7 mg, about 1.8 mg, about 1.9 mg, about 2 mg, about 2.1 mg, about 2.2 mg, about 2.3 mg, about 2.4 mg, about 2.5 mg, about 2.6 mg, about 2.7 mg, about 2.8 mg, about 2.9 mg, about 3 mg, about 3.1 mg, about 3.2 mg, about 3.3 mg, about 3.4 mg, about 3.5 mg, about 3.6 mg, about 3.7 mg, about 3.8 mg, about 3.9 mg, about 4 mg, about 4.1 mg, about 4.2 mg, about 4.3 mg, about 4.4 mg, about 4.5 mg, about 4.6 mg, about 4.7 mg, about 4.8 mg, about 4.9 mg, about 5 mg, about 6 mg, about 7 mg, about 8 mg, about 9 mg, about 10 mg, or about 11 mg.

In other embodiments, the amount of 5HT receptor agonist, or pharmaceutically acceptable salt, solvate, metabolite, derivative, or prodrug thereof in the pharmaceutical composition corresponds to no less than 0.001 mg, no less than 0.005 mg, no less than 0.01 mg, no less than 0.02 mg, no less than 0.03 mg, no less than 0.04 mg, no less than 0.05 mg, no less than 0.06 mg, no less than 0.07 mg, no less than 0.08 mg, no less than 0.09 mg, no less than 0.1 mg, no less than 0.11 mg, no less than 0.12 mg, no less than 0.15 mg, no less than 0.17 mg, no less than 0.2 mg, no less than 0.23 mg, no less than 0.25 mg, no less than 0.28 mg, no less than 0.3 mg, no less than 0.33 mg, no less than 0.35 mg, no less than 0.37 mg, no less than 0.4 mg, no less than 0.43 mg, no less than 0.45 mg, no less than 0.47 mg, no less than 0.5 mg, no less than 0.53 mg, no less than 0.55 mg, no less than 0.57 mg, no less than 0.6 mg, no less than 0.63 mg, no less than 0.65 mg, no less than 0.67 mg, no less than 0.7 mg, no less than 0.73 mg, no less than 0.75 mg, no less than 0.78 mg, no less than 0.8 mg, no less than 0.83 mg, no less than 0.85 mg, no less than 0.87 mg, no less than 0.9 mg, no less than 0.95 mg, no less than 1 mg, no less than 1.1 mg, no less than 1.2 mg, no less than 1.3 mg, no less than 1.4 mg, no less than 1.5 mg, no less than 1.6 mg, no less than 1.7 mg, no less than 1.8 mg, no less than 1.9 mg, no less than 2 mg, no less than 2.1 mg, no less than 2.2 mg, no less than 2.3 mg, no less than 2.4 mg, no less than 2.5 mg, no less than 2.6 mg, no less than 2.7 mg, no less than 2.8 mg, no less than 2.9 mg, no less than 3 mg, no less than 3.1 mg, no less than 3.2 mg, no less than 3.3 mg, no less than 3.4 mg, no less than 3.5 mg, no less than 3.6 mg, no less than 3.7 mg, no less than 3.8 mg, no less than 3.9 mg, no less than 4 mg, no less than 4.1 mg, no less than 4.2 mg, no less than 4.3 mg, no less than 4.4 mg, no less than 4.5 mg, no less than 4.6 mg, no less than 4.7 mg, no less than 4.8 mg, no less than 4.9 mg, no less than 5 mg, no less than 5.1 mg, no less than 5.2 mg, no less than 5.3 mg, no less than 5.4 mg, no less than 5.5 mg, no less than 5.6 mg, no less than 5.7 mg, no less than 5.8 mg, or no less than 5.9 mg.

In other embodiments, the amount of 5HT receptor agonist, or pharmaceutically acceptable salt, solvate, metabolite, derivative, or prodrug thereof in the pharmaceutical composition corresponds to no more than 0.005 mg, no more than 0.01 mg, no more than 0.02 mg, no more than 0.03 mg, no more than 0.04 mg, no more than 0.05 mg, no more than 0.06 mg, no more than 0.07 mg, no more than 0.08 mg, no more than 0.09 mg, no more than 0.1 mg, no more than 0.11 mg, no more than 0.12 mg, no more than 0.15 mg, no more than 0.17 mg, no more than 0.2 mg, no more than 0.23 mg, no more than 0.25 mg, no more than 0.28 mg, no more than 0.3 mg, no more than 0.33 mg, no more than 0.35 mg, no more than 0.37 mg, no more than 0.4 mg, no more than 0.43 mg, no more than 0.45 mg, no more than 0.47 mg, no more than 0.5 mg, no more than 0.53 mg, no more than 0.55 mg, no more than 0.57 mg, no more than 0.6 mg, no more than 0.63 mg, no more than 0.65 mg, no more than 0.67 mg, no more than 0.7 mg, no more than 0.73 mg, no more than 0.75 mg, no more than 0.78 mg, no more than 0.8 mg, no more than 0.83 mg, no more than 0.85 mg, no more than 0.87 mg, no more than 0.9 mg, no more than 0.95 mg, no more than 1 mg, no more than 1.1 mg, no more than 1.2 mg, no more than 1.3 mg, no more than 1.4 mg, no more than 1.5 mg, no more than 1.6 mg, no more than 1.7 mg, no more than 1.8 mg, no more than 1.9 mg, no more than 2 mg, no more than 2.1 mg, no more than 2.2 mg, no more than 2.3 mg, no more than 2.4 mg, no more than 2.5 mg, no more than 2.6 mg, no more than 2.7 mg, no more than 2.8 mg, no more than 2.9 mg, no more than 3 mg, no more than 3.1 mg, no more than 3.2 mg, no more than 3.3 mg, no more than 3.4 mg, no more than 3.5 mg, no more than 3.6 mg, no more than 3.7 mg, no more than 3.8 mg, no more than 3.9 mg, no more than 4 mg, no more than 4.1 mg, no more than 4.2 mg, no more than 4.3 mg, no more than 4.4 mg, no more than 4.5 mg, no more than 4.6 mg, no more than 4.7 mg, no more than 4.8 mg, no more than 4.9 mg, no more than 5 mg, no more than 5.1 mg, no more than 5.2 mg, no more than 5.3 mg, no more than 5.4 mg, no more than 5.5 mg, no more than 5.6 mg, no more than 5.7 mg, no more than 5.8 mg, no more than 5.9 mg, or no more than 6 mg.

In some embodiments, the amount of 5HT receptor agonist, or pharmaceutically acceptable salt, solvate, metabolite, derivative, or prodrug thereof used in a pharmaceutical composition is about 0.001 mg/kg to about 50 mg/kg. In some embodiments, the amount of 5HT receptor agonist, or pharmaceutically acceptable salt, solvate, metabolite, derivative, or prodrug thereof used in a pharmaceutical composition is about 0.005 mg/kg to about 10 mg/kg. In some embodiments, the amount of 5HT receptor agonist, or pharmaceutically acceptable salt, solvate, metabolite, derivative, or prodrug thereof used in a pharmaceutical composition is about 0.01 mg/kg to about 5 mg/kg. In some embodiments, the amount of 5HT receptor agonist, or pharmaceutically acceptable salt, solvate, metabolite, derivative, or prodrug thereof used in a pharmaceutical composition is about 0.05 mg/kg to about 1 mg/kg. In other embodiments, the amount of 5HT receptor agonist, or pharmaceutically acceptable salt, solvate, metabolite, derivative, or prodrug thereof in the pharmaceutical composition corresponds to about 0.001 mg/kg, about 0.005 mg/kg, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.11 mg/kg, about 0.12 mg/kg, about 0.15 mg/kg, about 0.17 mg/kg, about 0.2 mg/kg, about 0.23 mg/kg, about 0.25 mg/kg, about 0.28 mg/kg, about 0.3 mg/kg, about 0.33 mg/kg, about 0.35 mg/kg, about 0.37 mg/kg, about 0.4 mg/kg, about 0.43 mg/kg, about 0.45 mg/kg, about 0.47 mg/kg, about 0.5 mg/kg, about 0.53 mg/kg, about 0.55 mg/kg, about 0.57 mg/kg, about 0.6 mg/kg, about 0.63 mg/kg, about 0.65 mg/kg, about 0.67 mg/kg, about 0.7 mg/kg, about 0.73 mg/kg, about 0.75 mg/kg, about 0.78 mg/kg, about 0.8 mg/kg, about 0.83 mg/kg, about 0.85 mg/kg, about 0.87 mg/kg, about 0.9 mg/kg, about 0.95 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, about 3.8 mg/kg, about 3.9 mg/kg, about 4 mg/kg, about 4.1 mg/kg, about 4.2 mg/kg, about 4.3 mg/kg, about 4.4 mg/kg, about 4.5 mg/kg, about 4.6 mg/kg, about 4.7 mg/kg, about 4.8 mg/kg, about 4.9 mg/kg, about 5 mg/kg, about 6 mg/kg, about 7 mg/kg, about 8 mg/kg, about 9 mg/kg, or about 10 mg/kg.

In other embodiments, the amount of 5HT receptor agonist, or pharmaceutically acceptable salt, solvate, metabolite, derivative, or prodrug thereof in the pharmaceutical composition corresponds to no less than 0.001 mg/kg, no less than 0.005 mg/kg, no less than 0.01 mg/kg, no less than 0.02 mg/kg, no less than 0.03 mg/kg, no less than 0.04 mg/kg, no less than 0.05 mg/kg, no less than 0.06 mg/kg, no less than 0.07 mg/kg, no less than 0.08 mg/kg, no less than 0.09 mg/kg, no less than 0.1 mg/kg, no less than 0.11 mg/kg, no less than 0.12 mg/kg, no less than 0.15 mg/kg, no less than 0.17 mg/kg, no less than 0.2 mg/kg, no less than 0.23 mg/kg, no less than 0.25 mg/kg, no less than 0.28 mg/kg, no less than 0.3 mg/kg, no less than 0.33 mg/kg, no less than 0.35 mg/kg, no less than 0.37 mg/kg, no less than 0.4 mg/kg, no less than 0.43 mg/kg, no less than 0.45 mg/kg, no less than 0.47 mg/kg, no less than 0.5 mg/kg, no less than 0.53 mg/kg, no less than 0.55 mg/kg, no less than 0.57 mg/kg, no less than 0.6 mg/kg, no less than 0.63 mg/kg, no less than 0.65 mg/kg, no less than 0.67 mg/kg, no less than 0.7 mg/kg, no less than 0.73 mg/kg, no less than 0.75 mg/kg, no less than 0.78 mg/kg, no less than 0.8 mg/kg, no less than 0.83 mg/kg, no less than 0.85 mg/kg, no less than 0.87 mg/kg, no less than 0.9 mg/kg, no less than 0.95 mg/kg, no less than 1 mg/kg, no less than 1.1 mg/kg, no less than 1.2 mg/kg, no less than 1.3 mg/kg, no less than 1.4 mg/kg, no less than 1.5 mg/kg, no less than 1.6 mg/kg, no less than 1.7 mg/kg, no less than 1.8 mg/kg, no less than 1.9 mg/kg, no less than 2 mg/kg, no less than 2.1 mg/kg, no less than 2.2 mg/kg, no less than 2.3 mg/kg, no less than 2.4 mg/kg, no less than 2.5 mg/kg, no less than 2.6 mg/kg, no less than 2.7 mg/kg, no less than 2.8 mg/kg, no less than 2.9 mg/kg, no less than 3 mg/kg, no less than 3.1 mg/kg, no less than 3.2 mg/kg, no less than 3.3 mg/kg, no less than 3.4 mg/kg, no less than 3.5 mg/kg, no less than 3.6 mg/kg, no less than 3.7 mg/kg, no less than 3.8 mg/kg, no less than 3.9 mg/kg, no less than 4 mg/kg, no less than 4.1 mg/kg, no less than 4.2 mg/kg, no less than 4.3 mg/kg, no less than 4.4 mg/kg, no less than 4.5 mg/kg, no less than 4.6 mg/kg, no less than 4.7 mg/kg, no less than 4.8 mg/kg, no less than 4.9 mg/kg, or no less than 5 mg/kg.

In other embodiments, the amount of 5HT receptor agonist, or pharmaceutically acceptable salt, solvate, metabolite, derivative, or prodrug thereof in the pharmaceutical composition corresponds to no more than 0.005 mg/kg, no more than 0.01 mg/kg, no more than 0.02 mg/kg, no more than 0.03 mg/kg, no more than 0.04 mg/kg, no more than 0.05 mg/kg, no more than 0.06 mg/kg, no more than 0.07 mg/kg, no more than 0.08 mg/kg, no more than 0.09 mg/kg, no more than 0.1 mg/kg, no more than 0.11 mg/kg, no more than 0.12 mg/kg, no more than 0.15 mg/kg, no more than 0.17 mg/kg, no more than 0.2 mg/kg, no more than 0.23 mg/kg, no more than 0.25 mg/kg, no more than 0.28 mg/kg, no more than 0.3 mg/kg, no more than 0.33 mg/kg, no more than 0.35 mg/kg, no more than 0.37 mg/kg, no more than 0.4 mg/kg, no more than 0.43 mg/kg, no more than 0.45 mg/kg, no more than 0.47 mg/kg, no more than 0.5 mg/kg, no more than 0.53 mg/kg, no more than 0.55 mg/kg, no more than 0.57 mg/kg, no more than 0.6 mg/kg, no more than 0.63 mg/kg, no more than 0.65 mg/kg, no more than 0.67 mg/kg, no more than 0.7 mg/kg, no more than 0.73 mg/kg, no more than 0.75 mg/kg, no more than 0.78 mg/kg, no more than 0.8 mg/kg, no more than 0.83 mg/kg, no more than 0.85 mg/kg, no more than 0.87 mg/kg, no more than 0.9 mg/kg, no more than 0.95 mg/kg, no more than 1 mg/kg, no more than 1.1 mg/kg, no more than 1.2 mg/kg, no more than 1.3 mg/kg, no more than 1.4 mg/kg, no more than 1.5 mg/kg, no more than 1.6 mg/kg, no more than 1.7 mg/kg, no more than 1.8 mg/kg, no more than 1.9 mg/kg, no more than 2 mg/kg, no more than 2.1 mg/kg, no more than 2.2 mg/kg, no more than 2.3 mg/kg, no more than 2.4 mg/kg, no more than 2.5 mg/kg, no more than 2.6 mg/kg, no more than 2.7 mg/kg, no more than 2.8 mg/kg, no more than 2.9 mg/kg, no more than 3 mg/kg, no more than 3.1 mg/kg, no more than 3.2 mg/kg, no more than 3.3 mg/kg, no more than 3.4 mg/kg, no more than 3.5 mg/kg, no more than 3.6 mg/kg, no more than 3.7 mg/kg, no more than 3.8 mg/kg, no more than 3.9 mg/kg, no more than 4 mg/kg, no more than 4.1 mg/kg, no more than 4.2 mg/kg, no more than 4.3 mg/kg, no more than 4.4 mg/kg, no more than 4.5 mg/kg, no more than 4.6 mg/kg, no more than 4.7 mg/kg, no more than 4.8 mg/kg, no more than 4.9 mg/kg, no more than 5 mg/kg, no more than 6 mg/kg, no more than 7 mg/kg, no more than 8 mg/kg, no more than 9 mg/kg, or no more than 10 mg/kg.

In some embodiments, the amount of 5HT receptor agonist, or pharmaceutically acceptable salt, solvate, metabolite, derivative, or prodrug thereof in the pharmaceutical composition corresponds to about 1% w/w to about 50% w/w of the solids in the oral liquid formulation. In other embodiments, the amount of the pharmaceutically acceptable salt of a 5HT receptor agonist or a pharmaceutically acceptable salt, solvate, metabolite, derivative, or prodrug thereof correspond to about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, about 10% w/w, about 10.2% w/w, about 10.4% w/w, about 10.6% w/w, about 10.8% w/w, about 11% w/w, about 11.2% w/w, about 11.4% w/w, about 11.6% w/w, about 11.8% w/w, about 12% w/w, about 12.2% w/w, about 12.4% w/w, about 12.6% w/w, about 12.8% w/w, about 13% w/w, about 13.2% w/w, about 13.4% w/w, about 13.6% w/w, about 13.8% w/w, about 14% w/w, about 14.2% w/w, about 14.4% w/w, about 14.6% w/w, about 14.8% w/w, about 15% w/w, about 15.5% w/w, about 16% w/w, about 16.5% w/w, about 17% w/w, about 17.5% w/w, about 18% w/w, about 18.5% w/w, about 19% w/w, about 19.5% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, or about 50% w/w of the solids in the oral liquid formulation.

Therapeutic Uses-Disorders, Conditions and Symptoms

Provided herein are methods for managing disorders or conditions, comprising administering one or more 5HT receptor agonists, or pharmaceutically acceptable salts, solvates, metabolites, derivatives, or prodrugs thereof.

Further provided herein are methods of treating symptoms of disorders or conditions, comprising administering one or more 5HT receptor agonists, or pharmaceutically acceptable salts, solvates, metabolites, derivatives, or prodrugs thereof.

In some embodiments, the disorders or conditions are neurological disorders or conditions. In some embodiments, the disorders or conditions are neurocognitive disorders or conditions. In some embodiments, the disorders or conditions are neurodegenerative disorders or conditions. In some embodiments, the symptoms of the neurological condition are physical, behavioral, emotional, mental, or a combination thereof.

Provided herein are methods for managing or treating disorders, conditions or symptoms including but not limited to addiction disorders, such as but not limited to alcohol abuse, substance abuse, smoking, or obesity. Provided herein are methods for managing or treating disorders, conditions or symptoms including but not limited to eating disorders and auditory disorders. Provided herein are methods for managing or treating disorders, conditions or symptoms including but not limited to pain, such as but not limited to chronic pain. Provided herein are methods for managing or treating disorders, conditions or symptoms including but not limited to depression, bipolar disorder, post-traumatic stress disorder (PTSD), panic disorder, phobia, schizophrenia, psychopathy, or antisocial personality disorder. Provided herein are methods for managing or treating disorders, conditions or symptoms including but not limited to impulse disorders, such as but not limited to attention deficit hyperactivity disorder (ADHD), Tourette's syndrome or autism. Provided herein are methods for managing or treating disorders, conditions or symptoms including but not limited to compulsive disorder, such as but not limited to obsessive compulsive disorder (OCD), gambling, or aberrant sexual behavior. Provided herein are methods for managing or treating disorders, conditions or symptoms including but not limited to personality disorders, such as but not limited to conduct disorder, antisocial personality, or aggressive behavior.

Further examples of the disorders, conditions and symptoms which may be managed or treated include, by way of non-limiting examples:

Neurodevelopmental disorders such as, but not limited to, attention-deficit/hyperactivity disorder (ADHD), autism spectrum disorder, learning disorders and the like.

Schizophrenia spectrum and other psychotic disorders including but not limited to detachment from reality, delusions, hallucinations, and disorganized thinking and speech.

Bipolar and related disorders which may involve episodes of mania (periods of excessive excitement, activity, and energy) alternating with periods of depression.

Depressive disorders which may involve feelings of extreme sadness, reduced interest in previously enjoyable activities, including but not limited to depression, severe depression, major depressive disorder (MDD), premenstrual dysphoric disorder (PMDD) and the like.

Anxiety disorders which may involve worrying excessively about potential bad things or situations. Examples include generalized anxiety disorder (GAD), panic disorder and phobias (irrational fears of specific things) and the like.

Obsessive-compulsive and related disorders which may involve repeated, unwanted urges, thoughts, or images (obsessions) and feeling driven to taking repeated actions in response to them (compulsions). Non-limiting examples include obsessive-compulsive disorder (OCD), hoarding disorder, extreme nail biting, and hair-pulling disorder (trichotillomania).

Trauma and stressor-related disorders which may develop during or after stressful or traumatic life events. Non-limiting examples include post-traumatic stress disorder (PTSD) and acute stress disorder.

Dissociative disorders wherein the sense of self is may be disrupted, such as but not limited to dissociative identity disorder, dissociative amnesia and the like.

Somatic symptom and related disorders which may involve distressing and incapacitating physical symptoms with no clear medical cause. Non-limiting examples include illness anxiety disorder, somatic symptom disorder (hypochondriasis), factitious disorder and the like.

Feeding and eating disorders which may involve disturbances related to eating, such as but not limited to anorexia nervosa, bulimia nervosa, and binge eating disorder.

Elimination disorders which may involve inappropriate elimination (release) of urine or stool by accident or deliberately, such as but not limited to bedwetting (enuresis).

Sleep-wake disorders which may involve severe sleep disorders, including but not limited to insomnia disorder, nightmare disorder, sleep apnea, and restless legs syndrome.

Disruptive, impulse-control, and conduct disorders which may involve difficulty with emotional and/or behavioral self-control, such as but not limited to kleptomania (repeated stealing), pyromania, and intermittent explosive disorder.

Substance-related disorders which may involve problems associated with excessive use of substances such as alcohol (alcohol dependence, alcoholism), tobacco products, drugs, opioids (for example, cocaine, oxycodone, morphine and the like), recreational drugs, hallucinogens and the like.

Addictive disorders which may involve problems associated with excessive use of particular behaviors or fixations, such as but not limited to gambling disorder.

Neurocognitive disorders which may affect the ability to think and reason, such as but not limited to traumatic brain injury (TBI), Alzheimer's disease and the like.

Personality disorders which may involve enduring patterns of emotional instability and unhealthy behaviors that disrupt daily living and relationships. Examples include but are not limited to borderline, antisocial, and narcissistic personality disorders.

Gender dysphoria which may involve distress caused by a person's desire to be a different gender.

Sexual dysfunctions such as but not limited to premature ejaculation, erectile disorder, and female orgasmic disorder.

Paraphilic disorders (sexual perversion, sexual deviation) which may involve sexual interest in atypical objects, situations, fantasies, behaviors, or individuals. Examples include but are not limited to sexual sadism disorder, voyeuristic disorder, and pedophilic disorder.

Further examples of the disorders, conditions and symptoms which may be managed or treated include by way of non-limiting example, Fragile X syndrome, Down syndrome, migraine headache, cluster headache, psychiatric disorders, neurodevelopmental disorders, attention-deficit/hyperactivity disorder (ADHD), autism spectrum disorder, learning disorders, schizophrenia spectrum, psychotic disorders, bipolar disorders, depression, severe depression, major depressive disorder (MDD), premenstrual dysphoric disorder (PMDD), suicidality, mood related disorders, panic disorder, panic attack, phobias, agoraphobia, selective mutism, obsessive-compulsive disorder (OCD), hoarding disorder, hair-pulling disorder (trichotillomania), excoriation (skin-picking) disorder, substance-/medication-induced obsessive-compulsive disorder, trauma-related disorders, traumatic brain injury (TBI), post-traumatic stress disorder (PTSD), acute stress disorder, dissociative disorders, dissociative identity disorder, dissociative amnesia, anxiety, anxiety disorders, generalized anxiety disorder (GAD), social anxiety disorder, separation anxiety disorder, illness anxiety disorders, somatic disorders and diseases, somatic symptom disorder (hypochondriasis), factitious disorder, feeding disorders, eating disorders, anorexia, anorexia nervosa, bulimia nervosa, binge eating disorder, elimination disorders, enuresis, sleep disorders, insomnia, nightmare disorder, sleep apnea, central sleep apnea, narcolepsy, obstructive sleep apnea, hypopnea, and sleep-related hypoventilation, restless legs syndrome, jet lag, sexual dysfunction, premature ejaculation, erectile disorder, female orgasmic disorder, gender identity disorder, gender dysphoria, disruptive disorders, impulse-control disorders, conduct disorders, disruptive conduct disorders, impulse-control disorders, oppositional defiant disorder (ODD), aggression, kleptomania, pyromania, addictive disorders, substance dependence, substance abuse, alcoholism, drug addiction, opioid addiction, cocaine addiction, gambling addiction, tobacco dependence, food addiction, other forms of addiction to substances and behaviors, obesity, cognitive disorders, memory related disorders, learning related disorders, neurocognitive disorders, Alzheimer's disease, personality disorders, narcissistic personality disorders, Asperger syndrome, Tourette syndrome, Huntington's disease, Parkinson's disease, Lewy body disease, amyotrophic lateral sclerosis (ALS), Friedreich's ataxia, muscular atrophy, prion disease, dementia, vascular dementia, dementia/neurocognitive issues due to infection, dementia due to substance abuse or exposure to toxins, frontotemporal degeneration, mood disorders, delirium, aphasia, apraxia, agnosia, concussion, amnesia, anterograde amnesia, retrograde amnesia, body dysmorphic disorder, reactive attachment disorder, Fragile X syndrome, Down syndrome, migraines, migraine headache, cluster headache, cardiovascular disease, inflammatory conditions, fibromyalgia and pain.

Provided herein are methods for managing disorders or conditions, or treating symptoms of disorders or conditions, comprising administering one or more 5HT receptor agonists, or pharmaceutically acceptable salts, solvates, metabolites, derivatives, or prodrugs thereof. In some embodiments, the 5HT receptor agonist is a 5HT2 receptor agonist. In some embodiments, the 5HT2 receptor agonist is a 5HT2A receptor agonist, a 5HT2B receptor agonist and/or a 5HT2C receptor agonist. In some embodiments, the 5HT receptor agonist is psilocin or psilocybin or a pharmaceutically acceptable salt, solvate, metabolite, derivative, or prodrug thereof. In some embodiments, the therapeutically effective amount of the 5HT receptor agonist or a pharmaceutically acceptable salt, solvate, metabolite, derivative, or prodrug thereof is provided to the subject in need thereof in an amount insufficient to provide an adverse side effect, such as hallucinogenic experience.

In some embodiments, the therapeutically effective amount of 5HT receptor agonist or a pharmaceutically acceptable salt, solvate, metabolite, derivative, or prodrug thereof is provided to a subject in need thereof in an amount and/or formulation insufficient to provide a maximum plasma concentration ($C_{max}$) of (e.g. active form of the) 5HT receptor agonist or a pharmaceutically acceptable salt, solvate, metabolite, derivative, or prodrug thereof of 6 ng/ml or more. In some embodiments, the therapeutically effective amount of 5HT receptor agonist or a pharmaceutically acceptable salt, solvate, metabolite, derivative, or prodrug thereof is provided to a subject in need thereof in an amount and/or formulation to provide a maximum plasma concentration ($C_{max}$) of (e.g. active form of the) 5HT receptor agonist or a pharmaceutically acceptable salt, solvate, metabolite, derivative, or prodrug thereof of about 0.1 ng/ml or more and less than 6 ng/mL (e.g. at least 0.5 ng/mL and less than 6 ng/ml, about 1 ng/ml to about 5.5 ng/ml, about 2 ng/ml to about 5 ng/mL, or the like). In some embodiments, the therapeutically effective amount of 5HT receptor agonist or a pharmaceutically acceptable salt, solvate, metabolite, derivative, or prodrug thereof is provided to a subject in need thereof in an amount and/or formulation to provide a plasma concentration of (e.g. active form of the) 5HT receptor agonist or a pharmaceutically acceptable salt, solvate, metabolite, derivative, or prodrug thereof of at least 0.1 ng/ml (e.g. at least 0.2 ng/ml, at least 0.3 ng/ml, at least 0.5 ng/ml, or the like) after at least 6 hours (e.g. at least 12 hours, at least 24 hours, at least 36 hours, at least 48 hours, at least 72 hours, at least 96 hours, at least 120 hours, at least 144 hours, or the like).

In some embodiments, the therapeutically effective amount of 5HT receptor agonist or a pharmaceutically acceptable salt, solvate, metabolite, derivative, or prodrug thereof is provided to a subject in need thereof in an amount and/or formulation insufficient to provide a maximum plasma concentration ($C_{max}$) of (e.g. active form of the) 5HT receptor agonist or a pharmaceutically acceptable salt, solvate, metabolite, derivative, or prodrug thereof of about 0.001 ng/mL to about 10 ng/mL. In some embodiments, the therapeutically effective amount of 5HT receptor agonist or a pharmaceutically acceptable salt, solvate, metabolite, derivative, or prodrug thereof is provided to a subject in need thereof in an amount and/or formulation insufficient to provide a maximum plasma concentration ($C_{max}$) of (e.g. active form of the) 5HT receptor agonist or a pharmaceutically acceptable salt, solvate, metabolite, derivative, or prodrug thereof of about 0.01 ng/ml to about 5 ng/mL. In some embodiments, the therapeutically effective amount of 5HT receptor agonist or a pharmaceutically acceptable salt, solvate, metabolite, derivative, or prodrug thereof is provided to a subject in need thereof in an amount and/or formulation insufficient to provide a maximum plasma concentration ($C_{max}$) of (e.g. active form of the) 5HT receptor agonist or a pharmaceutically acceptable salt, solvate, metabolite, derivative, or prodrug thereof of about 0.05 ng/mL to about 1 ng/mL. In other embodiments, the therapeutically effective amount of 5HT receptor agonist or a pharmaceutically acceptable salt, solvate, metabolite, derivative, or prodrug thereof is provided to a subject in need thereof in an amount and/or formulation insufficient to provide a maximum plasma concentration ($C_{max}$) of (e.g. active form of the) 5HT receptor agonist or a pharmaceutically acceptable salt, solvate, metabolite, derivative, or prodrug thereof of about 0.001 ng/ml, about 0.005 ng/ml, about 0.01 ng/ml, about 0.02 ng/mL, about 0.03 ng/ml, about 0.04 ng/ml, about 0.05 ng/mL, about 0.06 ng/ml, about 0.07 ng/mL, about 0.08 ng/mL, about 0.09 ng/ml, about 0.1 ng/mL, about 0.11 ng/ml, about 0.12 ng/ml, about 0.15 ng/ml, about 0.17 ng/ml, about 0.2 ng/ml, about 0.23 ng/mL, about 0.25 ng/ml, about 0.28 ng/ml, about 0.3 ng/ml, about 0.33 ng/ml, about 0.35 ng/mL, about 0.37 ng/ml, about 0.4 ng/ml, about 0.43 ng/mL, about 0.45 ng/ml, about 0.47 ng/mL, about 0.5 ng/ml, about 0.53 ng/ml, about 0.55 ng/mL, about 0.57 ng/ml, about 0.6 ng/ml, about 0.63 ng/ml, about 0.65 ng/mL, about 0.67 ng/ml, about 0.7 ng/ml, about 0.73 ng/ml, about 0.75 ng/ml, about 0.78 ng/ml, about 0.8 ng/ml, about 0.83 ng/ml, about 0.85 ng/ml, about 0.87 ng/mL, about 0.9 ng/ml, about 0.95 ng/mL, about 1 ng/mL, about 1.1 ng/ml, about 1.2 ng/ml, about 1.3 ng/mL, about 1.4 ng/ml, about 1.5 ng/ml, about 1.6 ng/ml, about 1.7 ng/mL, about 1.8 ng/mL, about 1.9 ng/ml, about 2 ng/ml, about 2.1 ng/ml, about 2.2 ng/ml, about 2.3 ng/mL, about 2.4 ng/mL, about 2.5 ng/ml, about 2.6 ng/ml, about 2.7 ng/ml, about 2.8 ng/ml, about 2.9 ng/ml, about 3 ng/ml, about 3.1 ng/ml, about 3.2 ng/ml, about 3.3 ng/ml, about 3.4 ng/ml, about 3.5 ng/ml, about 3.6 ng/ml, about 3.7 ng/ml, about 3.8 ng/ml, about 3.9 ng/ml, about 4 ng/ml, about 4.1 ng/ml, about 4.2 ng/ml, about 4.3 ng/ml, about 4.4 ng/mL, about 4.5 ng/ml, about 4.6 ng/ml, about 4.7 ng/ml, about 4.8 ng/ml, about 4.9 ng/ml, about 5 ng/ml, about 5.1 ng/mL, about 5.2 ng/ml, about 5.3 ng/ml, about 5.4 ng/ml, about 5.5 ng/mL, about 5.6 ng/ml, about 5.7 ng/ml, about 5.8 ng/ml, about 5.9 ng/ml, or about 6 ng/mL.

In other embodiments, the therapeutically effective amount of 5HT receptor agonist or a pharmaceutically acceptable salt, solvate, metabolite, derivative, or prodrug thereof is provided to a subject in need thereof in an amount and/or formulation insufficient to provide a maximum plasma concentration ($C_{max}$) of (e.g. active form of the) 5HT receptor agonist or a pharmaceutically acceptable salt, solvate, metabolite, derivative, or prodrug thereof of no less than 0.001 ng/mL, no less than 0.005 ng/mL, no less than 0.01 ng/ml, no less than 0.02 ng/ml, no less than 0.03 ng/mL, no less than 0.04 ng/ml, no less than 0.05 ng/ml, no less than 0.06 ng/mL, no less than 0.07 ng/mL, no less than 0.08 ng/mL, no less than 0.09 ng/ml, no less than 0.1 ng/mL, no less than 0.11 ng/mL, no less than 0.12 ng/mL, no less than 0.15 ng/mL, no less than 0.17 ng/mL, no less than 0.2 ng/mL, no less than 0.23 ng/mL, no less than 0.25 ng/ml, no less than 0.28 ng/mL, no less than 0.3 ng/ml, no less than 0.33 ng/mL, no less than 0.35 ng/ml, no less than 0.37 ng/mL, no less than 0.4 ng/mL, no less than 0.43 ng/ml, no less than 0.45 ng/mL, no less than 0.47 ng/mL, no less than 0.5 ng/mL, no less than 0.53 ng/ml, no less than 0.55 ng/mL, no less than 0.57 ng/mL, no less than 0.6 ng/mL, no less than 0.63 ng/ml, no less than 0.65 ng/mL, no less than 0.67 ng/mL, no less than 0.7 ng/ml, no less than 0.73 ng/mL, no less than 0.75 ng/ml, no less than 0.78 ng/ml, no less than 0.8 ng/ml, no less than 0.83 ng/ml, no less than 0.85 ng/mL, no less than 0.87 ng/ml, no less than 0.9 ng/mL, no less than 0.95 ng/mL, no less than 1 ng/mL, no less than 1.1 ng/mL, no less than 1.2 ng/ml, no less than 1.3 ng/mL, no less than 1.4 ng/mL, no less than 1.5 ng/mL, no less than 1.6 ng/ml, no less than 1.7 ng/mL, no less than 1.8 ng/mL, no less than 1.9 ng/mL, no less than 2 ng/ml, no less than 2.1 ng/mL, no less than 2.2 ng/mL, no less than 2.3 ng/ml, no less than 2.4 ng/ml, no less than 2.5 ng/mL, no less than 2.6 ng/mL, no less than 2.7 ng/ml, no less than 2.8 ng/ml, no less than 2.9 ng/mL, no less than 3 ng/mL, no less than 3.1 ng/mL, no less than 3.2 ng/ml, no less than 3.3 ng/mL, no less than 3.4 ng/mL, no less than 3.5 ng/mL, no less than 3.6 ng/ml, no less than 3.7 ng/mL, no less than 3.8 ng/mL, no less than 3.9 ng/mL, no less than 4 ng/ml, no less than 4.1 ng/mL, no less than 4.2 ng/mL, no less than 4.3 ng/mL, no less than 4.4 ng/ml, no less than 4.5 ng/mL, no less than 4.6 ng/mL, no less than 4.7 ng/ml, no less than 4.8 ng/mL, no less than 4.9 ng/mL, no less than 5 ng/mL, no less than 5.1 ng/mL, no less than 5.2 ng/ml, no less than 5.3 ng/ml, no less than 5.4 ng/mL, no less than 5.5 ng/ml, no less than 5.6 ng/ml, no less than 5.7 ng/mL, no less than 5.8 ng/mL, or no less than 5.9 ng/mL.

In other embodiments, the therapeutically effective amount of 5HT receptor agonist or a pharmaceutically acceptable salt, solvate, metabolite, derivative, or prodrug thereof is provided to a subject in need thereof in an amount and/or formulation insufficient to provide a maximum plasma concentration ($C_{max}$) of (e.g. active form of the) 5HT receptor agonist or a pharmaceutically acceptable salt, solvate, metabolite, derivative, or prodrug thereof of no more than 0.005 ng/ml, no more than 0.01 ng/mL, no more than 0.02 ng/mL, no more than 0.03 ng/mL, no more than 0.04 ng/mL, no more than 0.05 ng/mL, no more than 0.06 ng/ml, no more than 0.07 ng/mL, no more than 0.08 ng/mL, no more than 0.09 ng/ml, no more than 0.1 ng/mL, no more than 0.11 ng/mL, no more than 0.12 ng/mL, no more than 0.15 ng/ml, no more than 0.17 ng/mL, no more than 0.2 ng/mL, no more than 0.23 ng/mL, no more than 0.25 ng/ml, no more than 0.28 ng/mL, no more than 0.3 ng/ml, no more than 0.33 ng/mL, no more than 0.35 ng/mL, no more than 0.37 ng/mL, no more than 0.4 ng/mL, no more than 0.43 ng/ml, no more than 0.45 ng/mL, no more than 0.47 ng/mL, no more than 0.5 ng/ml, no more than 0.53 ng/ml, no more than 0.55 ng/mL, no more than 0.57 ng/ml, no more than 0.6 ng/ml, no more than 0.63 ng/ml, no more than 0.65 ng/mL, no more than 0.67 ng/mL, no more than 0.7 ng/ml, no more than 0.73 ng/mL, no more than 0.75 ng/ml, no more than 0.78 ng/mL, no more than 0.8 ng/ml, no more than 0.83 ng/mL, no more than 0.85 ng/ml, no more than 0.87 ng/mL, no more than 0.9 ng/mL, no more than 0.95 ng/mL, no more than 1 ng/mL, no more than 1.1 ng/mL, no more than 1.2 ng/ml, no more than 1.3 ng/mL, no more than 1.4 ng/mL, no more than 1.5 ng/mL, no more than 1.6 ng/mL, no more than 1.7 ng/ml, no more than 1.8 ng/ml, no more than 1.9 ng/ml, no more than 2 ng/mL, no more than 2.1 ng/mL, no more than 2.2 ng/mL, no more than 2.3 ng/mL, no more than 2.4 ng/mL, no more than 2.5 ng/mL, no more than 2.6 ng/ml, no more than 2.7 ng/ml, no more than 2.8 ng/mL, no more than 2.9 ng/mL, no more than 3 ng/ml, no more than 3.1 ng/mL, no more than 3.2 ng/mL, no more than 3.3 ng/mL, no more than 3.4 ng/ml, no more than 3.5 ng/mL, no more than 3.6 ng/mL, no more than 3.7 ng/ml, no more than 3.8 ng/ml, no more than 3.9 ng/mL, no more than 4 ng/ml, no more than 4.1 ng/mL, no more than 4.2 ng/ml, no more than 4.3 ng/mL, no more than 4.4 ng/mL, no more than 4.5 ng/ml, no more than 4.6 ng/mL, no more than 4.7 ng/ml, no more than 4.8 ng/mL, no more than 4.9 ng/mL, no more than 5 ng/mL, no more than 5.1 ng/mL, no more than 5.2 ng/mL, no more than 5.3 ng/ml, no more than 5.4 ng/mL, no more than 5.5 ng/mL, no more than 5.6 ng/ml, no more than 5.7 ng/mL, no more than 5.8 ng/mL, no more than 5.9 ng/ml, or no more than 6 ng/mL.

In some embodiments, the pharmaceutical composition is an oral formulation, a buccal formulation, a nasal formulation, or an inhalation formulation. In some embodiments, the pharmaceutical composition is in a form selected from a spray, aerosol, mist, nebulae, ointment, cream, gel, paste, salve, solution, suspension, tincture, patch, and atomized vapor.

Therapeutic Regimens

In some embodiments, any pharmaceutical composition or formulation or 5HT receptor agonist agent disclosed herein is administered for therapeutic application. In some embodiments, the pharmaceutical composition or formation or 5HT receptor agonist agent is administered once per day, twice per day, three times per day or more. In certain embodiments, the pharmaceutical composition or formulation or 5HT receptor agonist agent is administered daily, every day, every alternate day, five days a week, once a week, every other week, two weeks per month, three weeks per month, once a month, twice a month, three times per month, or more. In some embodiments, the pharmaceutical composition or formulation or 5HT receptor agonist agent is administered for at least 1 month, 2 months, 3 months, 4 months, 5 months, 6 months, 7 months, 8 months, 9 months, 10 months, 11 months, 12 months, 18 months, 2 years, 3 years, or more.

In some embodiments, one or more pharmaceutical compositions are administered simultaneously, sequentially, or at an interval period of time. In some embodiments, one or more pharmaceutical compositions are administered simultaneously. In some cases, one or more pharmaceutical compositions are administered sequentially. In additional cases, one or more pharmaceutical compositions are administered at an interval period of time (e.g. the first administration of a first pharmaceutical composition is on day one followed by an interval of at least 1, 2, 3, 4, 5, or more days prior to the administration of at least a second pharmaceutical composition).

In some embodiments, two or more different pharmaceutical compositions are co-administered. In some instances, the two or more different pharmaceutical compositions are co-administered simultaneously. In some cases, the two or more different pharmaceutical compositions are co-administered sequentially without a gap of time between administrations. In other cases, the two or more different pharmaceutical compositions are co-administered sequentially with a gap of about 0.5 hour, 1 hour, 2 hour, 3 hour, 12 hours, 1 day, 2 days, or more between administrations.

In some embodiments, the amount of a given agent that corresponds to such an amount varies depending upon factors such as the particular compound, the severity of the disease, the identity (e.g. weight) of the subject or host in need of treatment, but nevertheless is routinely determined in a manner known in the art according to the particular circumstances surrounding the case, including, e.g. the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the individual subject, the severity of the disease or condition being treated, and the judgment of the practitioner.

Kits/Article of Manufacture

Provided herein, in certain embodiments, are kits and articles of manufacture for use with one or more of the pharmaceutical compositions, formulations, and/or dosage forms of 5HT receptor agonist or a pharmaceutically acceptable salt, solvate, metabolite, derivative, or prodrug thereof disclosed herein. Such kits include a carrier, package, or container that is compartmentalized to receive one or more containers such as vials, tubes, and the like, each of the container(s) comprising one of the separate elements to be used in a method disclosed herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include a composition of 5HT receptor agonist, or pharmaceutically acceptable salt, solvate, metabolite, derivative, or prodrug thereof disclosed herein. Such kits optionally include an identifying description or label or instructions relating to its use in the methods disclosed herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g. as a package insert. In one embodiment, a label is used to indicate that the contents are to be used for a specific therapeutic application. The label also indicates directions for use of the contents, such as in the methods disclosed herein.

In certain embodiments, the pharmaceutical compositions are presented in a pack or dispenser device which contains one or more unit dosage forms comprising a 5HT receptor agonist or a pharmaceutically acceptable salt, solvate, metabolite, derivative, or prodrug thereof. The pack, for example, contains metal or plastic foil, such as a blister pack. In some embodiments, the pack contains the pharmaceutical compositions described herein and a second agent. In certain embodiments, the pharmaceutical compositions are presented in a pack or dispenser device which contains one or more unit dosage forms comprising a 5HT receptor agonist or a pharmaceutically acceptable salt, solvate, metabolite, derivative, or prodrug thereof, and one or more unit dosage forms comprising a second agent. In some embodiments, the second agent is a placebo. In some embodiments, the second agent is a therapeutic agent. In some embodiments, the pack is organized to aid patient compliance as to which agent to take at which time and/or on which day. In some embodiments, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions comprising a 5HT receptor agonist or a pharmaceutically acceptable salt, solvate, metabolite, derivative, or prodrug thereof formulated in a compatible pharmaceutical carrier are also prepared, placed in an appropriate container, and labeled for treatment of an indicated condition.

Definitions

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms “a”, “an”, and “the” include plural referents unless the context clearly dictates otherwise. In this application, the use of “or” means “and/or” unless stated otherwise. Furthermore, use of the term “including” as well as other forms, such as “include”, “includes,” and “included,” is not limiting.

The section headings used herein are for organizational purposes only and are not to be construed as limiting the subject matter disclosed.

As used herein, the terms “individual(s)”, “subject(s)” and “patient(s)” mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician’s assistant, an orderly or a hospice worker).

As used herein, ranges and amounts can be expressed as “about” a particular value or range. About also includes the exact amount. Hence “about 5 μL” means “about 5 μL” and also “5 μL.” Generally, the term “about” includes an amount that would be expected to be within experimental error.

The terms “controlled release dosage form” and “controlled release layer” are used interchangeably and defined as those whose drug release characteristics of time course and/or location are chosen to accomplish therapeutic or convenience objectives not offered by conventional immediate release dosage forms. The rate of release of the active drug from a controlled release layer or dosage form is controlled by features of the dosage form and/or in combination with physiologic or environmental conditions rather than by physiologic or environmental conditions alone. The controlled release dosage forms are used to maintain drug plasma levels within the therapeutic window. The controlled release dosage forms of certain embodiments attempt to deliver therapeutically effective amounts of active drug as a once-daily dose so that the ratio $C_{max}/C_{min}$ in the plasma at steady state is less than the therapeutic index, and to maintain drug levels at constant effective levels to provide a therapeutic benefit over a period of time (e.g. 24-hour period). In certain embodiments controlled release dosage forms provide a substantially constant or gradually decreasing rate of drug release so as to provide plasma levels which remain substantially invariant with time. In certain embodiments controlled release dosage forms are designed to provide a quick increase in the plasma concentration of the drug which remains substantially constant within the therapeutic range of the drug for a period of time (e.g. 24-hour period). Alternatively, in some other embodiments controlled release dosage forms are designed to provide a quick increase in the plasma concentration of the drug, which although might not remain constant, declines at a rate such that the plasma concentration remains within the therapeutic range for a period of time (e.g. 24-hour period).

The term “controlled release matrix” refers to a polymeric matrix that is capable of delivering a bioactive agent at a controlled rate for a period of time. Although there might be an initial burst phase, the overall release kinetics of the bioactive agent from the matrix are generally linear, such that a relatively constant supply of bioactive agent is released over the desired time period. The time period might vary from several hours to several days, depending upon the bioactive agent and its intended use. In general, it is preferable that the percentage of bioactive agent released from the controlled matrix over the treatment period be relatively high (e.g. at least about 50%, at least about 75%, at least about 90%, or at least about 95%) to avoid waste of unreleased bioactive agent.

The term “immediate release” layer or dosage form refers to the release of an active agent substantially immediately upon administration. For example, immediate release includes but not limited to contact with gastric juices and results in substantially complete dissolution within about 1 hour. Immediate release components might also be referred to as instant release. When used in association with the dissolution profiles discussed herein, the term “immediate release” refers to that portion of a dosage form disclosed herein which delivers active agent over a period of time less than 1 hour.

The terms “coating composition”, “coat composition”, “coating solution”, “coat solution”, “coating suspension”, and “coat suspension” as used herein are used interchangeably and are defined to mean a mixture of excipients that is used to create a controlled release coating. The coating composition is applied onto a 5HT receptor agonist or a pharmaceutically acceptable salt, solvate, metabolite, derivative, or prodrug thereof core to form an intermediate coating, and the intermediate coating is cured to form the controlled release coating.

The terms “effective amount” or “pharmaceutically effective amount” or “therapeutically effective amount” refer to a nontoxic but sufficient amount of the agent to provide the desired biological, therapeutic, and/or prophylactic result. That result might be reduction and/or alleviation of the signs, symptoms, or causes of a disease, or any other desired alteration of a biological system. For example, an “effective amount” for therapeutic uses is the amount of a 5HT receptor agonist or a pharmaceutically acceptable salt, solvate, metabolite, derivative, or prodrug thereof as disclosed herein per se or a composition comprising a 5HT receptor agonist or a pharmaceutically acceptable salt, solvate, metabolite, derivative, or prodrug thereof as disclosed herein required to provide a clinically significant decrease in a disease. An appropriate effective amount in any individual case might be determined by one of ordinary skill in the art using routine experimentation.

In some instances, the term “low dose” as used herein refers to an amount of a therapeutic agent (e.g. a 5HT receptor agonist or a pharmaceutically acceptable salt, solvate, metabolite, derivative, or prodrug thereof), which is sufficient to provide the desired biological, therapeutic, and/or prophylactic result, while insufficient to induce an undesired effect (e.g. such as a hallucinogenic experience, a perturbation in the user’s sense of reality or perceptions).

The term “mucoadhesive agent” refers to an agent that adheres to a mucous membrane. The mucous membrane consists of one or more layers of epithelial cells overlying a layer of loose connective tissue. Examples of mucous membranes include, but not limited to, tongue mucosa, bronchial mucosa, endometrium, esophageal mucosa, gastric mucosa, intestinal mucosa, nasal mucosa, olfactory mucosa, oral mucosa, penile mucosa, vaginal mucosa, and anal mucosa.

The term “transmucosal administration” refers to the route of administration in which the drug is diffused through the mucous membrane. This might refer to inhalation, nasal, sublingual, vaginal, rectal, or ocular routes.

The term "5HT receptor agonist agent" refers to a 5HT receptor agonist as a free base or a derivative or analog thereof. Included in the term are salts, solvates, metabolites, prodrugs, isomers, tautomers, isotopic derivatives, and the like, of a 5HT receptor agonist. In some embodiments, the derivative, analogs, salts, solvates, metabolites, prodrugs, isomers, tautomers, isotopic derivatives, etc are pharmaceutically acceptable derivative, analogs, salts, solvates, metabolites, prodrugs, isomers, tautomers, isotopic derivatives of a 5HT receptor agonist.

The term "pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation (Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich: Wiley-VCH/VHCA, 2002). Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound described herein with an acid to provide a "pharmaceutically acceptable acid addition salt." In some embodiments, the compound described herein (i.e. free base form) is basic and is reacted with an organic acid or an inorganic acid. Inorganic acids include, but are not limited to, hydrochloric acid, hydrobromic acid, metaphosphoric acid, nitric acid, phosphoric acid, and sulfuric acid. Organic acids include, but are not limited to, 1-hydroxy-2-naphthoic acid; 2,2-dichloroacetic acid: 2-hydroxyethanesulfonic acid; 2-oxoglutaric acid: 4-acetamidobenzoic acid; 4-aminosalicylic acid; acetic acid, adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid, citric acid; cyclamic acid; dodecylsulfuric acid; ethane-1,2-disulfonic acid; ethanesulfonic acid; formic acid, fumaric acid, galactaric acid, gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL), lactobionic acid; lauric acid, maleic acid; malic acid (−L), malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt.

In some embodiments, pharmaceutically acceptable salts are obtained by reacting a compound described herein with a base to provide a "pharmaceutically acceptable base addition salt". In some embodiments, the compound described herein is acidic and is reacted with a base. In such situations, an acidic proton of the compound described herein is replaced by a metal ion, e.g. lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms, i.e. solvates. In some embodiments, solvates contain either stoichiometric or non-stoichiometric amounts of a solvent, and are formed during the process of isolating or purifying the compound with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogen atoms of the compounds described herein is replaced with deuterium.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof (Jean Jacques, Andre Collet, Samuel H. Wilen, "Enantiomers, Racemates and Resolutions", John Wiley And Sons, Inc., 1981). In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. The prodrug might be a substrate for a transporter. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyamino acid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes might produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

A compound is "dissolved" when it is "in solution", and does not spontaneously come out of solution to from a separate phase. In order to be dissolved, the compound need not dissociate completely on a molecular level, but must remain in solution so as to be effective in treatment of a disease or condition. A dissolved compound might be present in a micellar, emulsified, or liposomal form.

"Solubility" generally means the amount of a compound dissolved in a solvent. Suitable solvents include aqueous and non-aqueous solvents.

"Poor solubility" means a small amount of compound dissolved in a solvent. Poor solubility is not an absolute term, but depends on the amount of the compound that is needed for effective treatment of a disease or condition. A compound will be poorly soluble if its solubility is lower than is desired in order for an effective treatment of a disease or condition.

"Enhanced solubility" means higher solubility than for a 5HT receptor agonist or a pharmaceutically acceptable salt, solvate, metabolite, derivative, or prodrug thereof alone. Enhanced solubility in water can be useful because many bodily fluids such as blood are water based (aqueous) and therefore, a more water soluble drug might have higher bioavailability. While the exact solubility of a compound in pure water is not the same as in an aqueous solution such as blood, a composition's solubility in pure water is often a good indication of solubility in other aqueous solutions.

A "tautomer" refers to a proton shift from one atom of a molecule to another atom of the same molecule. The compounds presented herein might exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

compounds such as powdered alcohols (e.g. menthol and ethanol), and compounds such as lipophilic enhancers which are safe to be used orally (Nicolazzo, Reid and Finnin *J Pharmaceutical Sciences* Vol 93, No 8 Aug. 2004 2054-2063). Fatty and other acids: oleic acid, capric acid, lauric acid, lauric acid/propylene glycol, methyloleate, ysophosphatidylcholine, phosphatidylcholine (Sudhakar et al. *JCR* 114 (2006) 15-40), oleic acid co-delivered with PEG 200, (Lee and Kellaway *Int J Pharmaceutics* 204 (2000) 137-144). Lysalbinic acid (Starokadomdkyy & Dubey *Int J Pharmaceutics* 308 (2006) 149-154). Non-surfactants such as unsaturated cyclic ureas. Others include: glucosaminoglycans (GAGs), aprotinin, azone, cyclodextrin, dextran sulfate, curcumin, menthol, Polysorbate 80, sulfoxides and various alkyl glycosides; Chitosan-4-thiobutylamide, chitosan-4-thiobutylamide/GSH, chitosan-cysteine, chitosan-(85% degree N-deacetylation), poly(acrylic acid)-homocysteine, polycarbophil-cysteine, polycarbophil-cysteine/GSH, chitosan-4-thioethylamide/GSH, chitosan-4-thioglycholic acid; hyaluronic acid in 3 molecular weights (Sandri et al.: *J Pharmacy and Pharmacology* 2004, 56:1083-1090); bile salts (dihydroxy and trihydroxy), sodium glycocholate, sodium deoxycholate, sodium taurocholate, sodium glycodeoxycholate, sodium taurodeoxycholate (Artusi et al.: *Int J Pharmaceutics* 250 (2003) 203-213); and propanolol hydrochloride (Akbari et al.: *Il Farmaco* 59 (2004) 155-161).

The term "complexing agents" when used herein includes agents in the group consisting of: cyclodextrins, calcium acetate, poly(methyl vinyl ether/maleic anhydride),

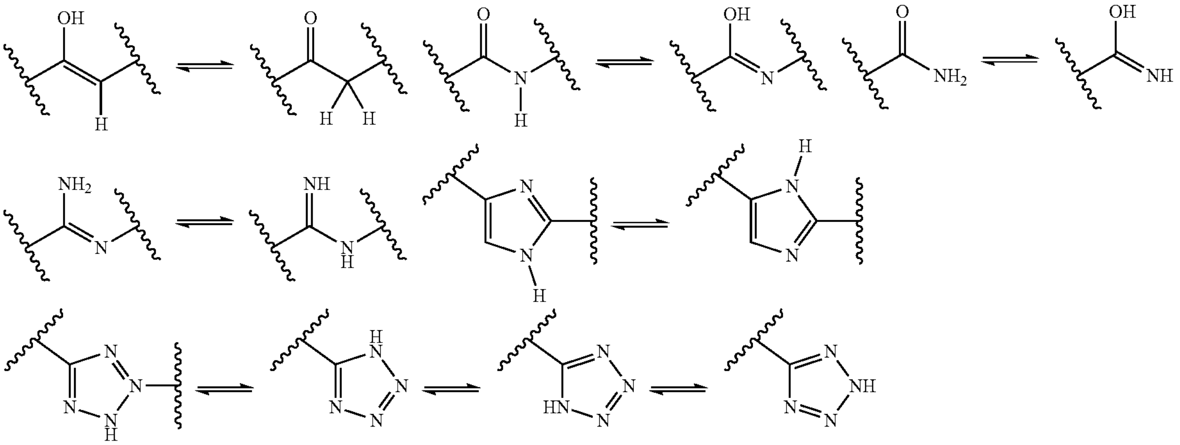

The term "taste masking agents" when used herein refers to taste receptor blockers, compounds which mask the chalkiness, grittiness, dryness and/or astringent taste properties of an active compound, compounds which reduce throat catch as well as compounds which add a flavor.

The term "enhancers" when used herein refers to agents which work to increase membrane permeability and/or work to increase the solubility of a particular active. Both issues can be pivotal to the properties of the formulation. The following are examples. Chelators: EDTA, citric acid, sodium salicylate, methoxysalicylates (see Senel & Hincal: *JCR* 72 2001 133-144; Malhalingam et al.: *AAPS Pharmascitech* 2007 (8) vol 3 Article 55). Surfactants: sodium lauryl sulphate, polyoxyethylene, POE-9-laurylether, POE-20-cetylether, benzalkonium chloride, 23-lauryl ether, cetylpyridinium chloride, cetyltrimethyl ammonium bromide, amphoteric and cationic surfactants. Membrane disrupting The term "treating" and its grammatical equivalents as used herein include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding the fact that the patient might still be afflicted with the underlying disorder. For prophylactic benefit, a method might be performed on, or a composition might be administered to a patient at risk of developing a disease, or to a patient reporting one or more of the physiological symptoms of such conditions, even though a diagnosis of the condition might not have been made.

While generally high drug solubility is desired, is would be appreciated by a person of ordinary skill in the art that there are other considerations in creating a pharmaceutical composition such as viscosity, stability, potential toxicity, etc. that might result a composition with lower solubility being more desirable for a particular therapy or delivery method as long as the amount of available drug is enough for the application. Pharmaceutical compositions disclosed herein provide the ability to optimize these factors.

EXAMPLES

These examples are provided for illustrative purposes only and not to limit the scope of the claims provided herein.

Example 1. Oral Formulation of a 5HT Receptor Agonist

A pharmaceutical composition of psilocybin is prepared as follows: 150 g of psilocybin is mixed with 30.4 g of pregelatinized starch, 23.8 g of microcrystalline cellulose, 6.1 g of polyvinylpyrrolidone, and 6.1 g of sodium starch glycollate. The mixture is blended for about 10 minutes. The resultant pharmaceutical composition is formulated into a suitable dosage form.

Example 2. Controlled Release Dosage Form

A controlled release dosage form of psilocybin 25 mg tablet is prepared as follows.

| Ingredient | % w/w |
|---|---|
| Psilocybin HCl | 90.20 |
| Silicon dioxide | 2.70 |
| Polyvinyl alcohol (PVA)* | 3.00 |
| Atomized glyceryl behenate | 3.30 |
| Magnesium stearate | 0.80 |
| Total | 100.00 |

*The PVA is prepared as a 4% solution (w/w) in purified water. The purified water is not considered as part of the theoretical batch size since it is evaporated during drying of the core in the fluid bed granulator.

All of the psilocybin and silicon dioxide is transferred to a V-blender and blended for about 10 minutes. The blended material is then discharged into a fluid bed granulator and granulation is carried out in the presence of the PVA solution.

After drying, the granules are sized by passing the granules through a 0.40 mm screen. The screened granules are then transferred to a V-blender and blended with the atomized glyceryl behenate for about 10 minutes. Finally, the magnesium stearate is added and blending is carried out for about 10 more minutes.

The psilocybin tablet cores are then coated with a controlled release coating formulation. The coating process is carried out in an apparatus equipped with a coating chamber. The mesh size of the bottom screen is 200 μm and the size of the spray nozzle is 1 mm.

Coated tablets are dried for about 30 minutes. After application of the coating the tablets are cured in an oven at 62±2° C. for about 2 hours.

The psilocybin tablet cores are next coated with the coating formulation to a weight gain of either 14% or 16% w/w by weight of the tablet core and cured in an oven at from about 60° C. to about 75° C. for about 2 hours to about 15 hours.

The resulted psilocybin core coated with a controlled release layer is further coated with an immediate-release layer comprising 15 mg of promethazine hydrochloride.

Example 3. Controlled Release Matrix of Psilocybin

A controlled release matrix containing psilocybin is prepared as follows. A mixture of 25% psilocybin, or a pharmaceutically acceptable salt, solvate, metabolite, derivative, or prodrug thereof (such as psilocybin HCl) is combined with a polymeric matrix such as PLGA polymer and melt extruded using a twin screw extruder (available from American LEISTRITZ Extruder Corp. USA, Somerville, N.J. 08876). Psilocybin is fed in a continuous manner to the twin screw extruder from a loss-in-weight feeder (available from K-Iron International, Inc., Pitman, N.J. 08071). The polymeric matrix is fed in a similar manner. The ratio of the bioactive agent to the polymeric matrix is controlled by the relative mass flow rate of bioactive agent from the first feeder to that of the polymeric matrix from the second feeder. The feeders and extruder are purged with dry air or nitrogen gas to maintain low humidity. The polymeric matrix is melted within the extruder operating at a temperature of 120° C. Psilocybin is not melted but is mixed within the molten and flowing polymeric matrix. The extruder forces or pumps the mixed bioactive agent and polymeric matrix through a rectangular shaped orifice or die to shape the material into an extrudate with width of about 5 mm to about 10 mm and a thickness from about 50 μm and about 250 μm. After cooling, the extrudate is cut into strips with a desired length and packaged. The individual strips are placed and sealed inside of a sterilization pouch such as foil-foil pouch (available from Oliver Products, 445 Sixth Street, NW, Grand Rapids, Mich. 49504 USA).

Example 4. Transmucosal Delivery of Psilocybin Compositions

Pharmaceutical composition for the nasal transmucosal delivery containing psilocybin, or a pharmaceutically acceptable salt, solvate, metabolite, or prodrug thereof is formulated into a suitable form, and administered by spray as a medicine for external use.

For preparation of spray, psilocybin, or a pharmaceutically acceptable salt, solvate, metabolite, derivative, or prodrug thereof (such as psilocybin HCl) is dissolved in a solvent (such as water, ethylene glycol, or glycerin), or suspended. The concentration of psilocybin, or a pharmaceutically acceptable salt, solvate, metabolite, derivative, or prodrug thereof in the solution is from about 5 mg/mL to about 50 mg/mL. To the resulted solution, a mucoadhesive agent is added (such as Carbopol 974P). The concentration of the mucoadhesive agent in the resulted mixture is from about 1 mg/mL to about 25 mg/mL. The resulted medicinal solution is filled in a container having a specific spraying device (valve) with a low viscous spraying agent. For this, the medicinal solution is sprayed in the type of smog using pressure. A dose of the pharmaceutical compositions containing psilocybin, or a pharmaceutically acceptable salt, solvate, metabolite, derivative, or prodrug thereof is 0.1 mg-10 mg/kg/day, and is altered according to the composition used and/or patient's condition.

Example 5. Preparation of Liposomal Psilocybin Formation

| Ingredient | Quantity (mg/g of cream) |
|---|---|
| psilocybin | 5.0 |
| soya lecithin | 200.0 |
| cholesterol | 20.0 |
| tetraglycol | 100.0 |
| dimethylisosorbide | 50.0 |
| methylparaben | 2.0 |
| propylparaben | 0.2 |
| BHT | 0.1 |
| sodium chloride | 1.0 |
| HPMC | 15.0 |
| sodium hydroxide | 0.6 |
| citric acid | 1.0 |
| purified water, USP | 603.6 |

Heat the soya lecithin, tetraglycol and dimethyl isosorbide to about 70-75° C. Dissolve the psilocybin, cholesterol and butylated hydroxytoluene in the heated mixture. Stir until complete dissolution is obtained. Heat about one third of the water to 80-95° C. in a separate vessel and dissolve the preservatives methylparaben and propylparaben in the heated water while stirring. Allow the solution to cool to about 25° C. and then add the disodium edetate, sodium chloride, sodium hydroxide and citric acid. Add the remainder of the water and stir to obtain a complete solution. Transfer the organic mixture into the aqueous mixture by means of a vacuum, while homogenizing the combination with a high-shear mixer until a homogeneous product is obtained. Add the hydroxypropyl methylcellulose into the biphasic mixture by means of a vacuum while homogenizing with a mixer. The homogenizer is a Silverson high-shear mixer operating at approximately 3000 rpm. Single bilayered liposomes are formed. The white lipogel cream is ready for use.

Example 6. Preparation of a Psilocybin Nanoparticle Formulation

Seven hundred and fifty (750) mg (15 mg/ml theoretical) of a diblock copolymer consisting of the combination of a poly(d,l-lactic acid) of mass 30 kD and of a PEG of mass 2 kD (PLA-PEG) and 250 mg (5 mg/ml theoretical) of psilocybin is mixed in 20 ml of ethyl acetate (solution A). 175 mg of lecithin E80 and 90 mg of sodium oleate is dispersed in 50 ml of 5% w/v glucose solution (solution B). Solution A is emulsified in solution B with an Ultra-turrax stirrer and the pre-emulsion is then introduced into a Microfluidizer 110 S® type homogenizer for 10 minutes at 10° C. The volume of emulsion recovered is about 70 ml (70 g). The ethyl acetate is removed using a rotary evaporator at reduced pressure (100 mm of mercury) to a suspension volume of about 45 ml (45 g).

Example 7. Preparation of a Gel Psilocybin Formulation

| Ingredient | Quantity (mg/g of formulation) |
|---|---|
| psilocybin | 5.0 |
| chitosan | 30.0 |

-continued

| Ingredient | Quantity (mg/g of formulation) |
|---|---|
| glycerophosphate disodium | 80.0 |
| water | 880 |

A 5 ml solution of acetic acid is titrated to a pH of about 4.0. The chitosan is added to achieve a pH of about 5.5. The psilocybin is then dissolved in the chitosan solution. This solution is sterilized by filtration. A 5 ml aqueous solution of glycerophosphate disodium is also prepared and sterilized. The two solutions are mixed and within 2 h at 37° C., the desired gel is formed.

Example 8. Preparation of a Gel/Liposome Psilocybin Formulation

| Ingredient | Quantity |
|---|---|
| psilocybin | 5.0 mg/g |
| liposomes | 15 umol/ml |
| chitosan-glycerophosphate | 100.0 mg/g |

The liposomes are prepared in the presence of the psilocybin by the reversed-phase evaporation method, where lipids in chloroform or chloroform-methanol (2:1, v/v) are deposited on the sides of a tube by evaporation of the organic solvent. The lipid film is redissolved in diethyl ether and the aqueous phase (pH 7.4 300 mOsm/kg) containing 20 mM Hepes and 144 mM NaCl is added. The mixture is sonicated to obtain a homogeneous emulsion, and then the organic solvent is removed under vacuum. The preparation is extruded to obtain the required liposome size and free components removed by size-exclusion chromatography using a Sepbadex G-50 column (Amersham Pharmacia Biotech, Uppsala, Sweden).

To prepare the chitosan-glycerophosphate formulation, a 5 ml solution of acetic acid is titrated to a pH of about 4.0. The chitosan is added to achieve a pH of about 5.5. This solution is sterilized by filtration. A 5 ml aqueous solution of glycerophosphate disodium is also prepared and sterilized. The two solutions are mixed and within 2 h at 37° C., and the desired gel is formed. The chitosan-glycerophosphate solution is gently mixed with the liposomes at room temperature.

Example 9: Clinical Trial to Establish Maximum Dose of Psilocybin without Incidence of a Hallucinogenic Event Adult individuals (e.g. aged 25-50 in humans) are administered varying doses of a 5HT receptor agonist (e.g. psilocybin) with the primary endpoint to establish at what dose individuals experience a hallucinogenic event. The trial also involves administering the 5HT receptor agonist at various frequencies (e.g. daily, every other day, twice a week, once a week, once every two weeks and the like) with the endpoint to determine the most effective dosing regimen, without experiencing a hallucinogenic event. This dose, or lower, and dosing regimen is used in the clinical trials described below. Separate cohorts of individuals are administered different dosage forms, with a first cohort being administered an immediate release 5HT receptor agonist, a second cohort being administered a controlled release 5HT receptor agonist, a third cohort being administered a dosage form (or combination) comprising an immediate release component (e.g. coating) and a controlled release component (core), each component comprising 5HT receptor agonist, and a fourth cohort administered the similar dosage form as the third cohort, with the exception that the controlled release component further comprises an additional agent (e.g. anti-inflammatory agent).

Example 10. Effects of 5HT Receptor Agonist in Major Depressive Disorder

The depression lowering activity of 5HT receptor agonist (e.g. psilocybin), administered under four dosing regimens (once daily, every other day, once weekly, and twice weekly) is investigated in a double-blind, placebo-controlled, parallel-group, randomized, 12 week study in depressed adult volunteers.

In human individuals, the study is performed in compliance with the current version of the declaration of Helsinki and with the ICH note for guidance on good clinical practice.

For human individuals, depressed individuals, aged 18-55 years inclusive, with a body mass index (BMI) within 18-30 $kg/m^2$ inclusive, having provided a written informed consent, non-smokers for at least 6 months, not using any drug treatment for 2 weeks before screening (2 months for enzyme-inducing drugs) except occasional acetaminophen. The individuals are confined at a clinical site beginning the day before dose administration until 72 hours after final dose administration on Day 17 and return for a follow-up visit on Day 21±1.

Endpoints

The primary efficacy endpoint is:

a. Individual assessment of depression using the Montgomery Asberg Depression Rating Scale The secondary efficacy endpoints are:

a. Individual assessment of change in mood symptoms using the GRID-Hamilton
b. Recorded hallucinogenic experiences Treatment Regimen Individuals are randomized into sixteen groups:

Group 1 (n=5): Placebo administered once weekly
Group 2 (n=10): Immediate release 5HT receptor agonist administered once weekly
Group 3 (n=10): Controlled release 5HT receptor agonist administered once weekly
Group 4 (n=10): Immediate release+controlled release 5HT receptor agonist administered once weekly
Group 5 (n=5): Placebo administered twice weekly
Group 6 (n=10): Immediate release 5HT receptor agonist administered twice weekly
Group 7 (n=10): Controlled release 5HT receptor agonist administered twice weekly
Group 8 (n=10): Immediate release+controlled release 5HT receptor agonist administered twice weekly
Group 9 (n=5): Placebo administered every other day
Group 10 (n=10): Immediate release 5HT receptor agonist administered every other day Group 11 (n=10): Controlled release 5HT receptor agonist administered every other day
Group 12 (n=10): Immediate release+controlled release 5HT receptor agonist administered every other day
Group 13 (n=5): Placebo administered daily
Group 14 (n=10): Immediate release 5HT receptor agonist administered daily
Group 15 (n=10): Controlled release 5HT receptor agonist administered daily
Group 16 (n=10): Immediate release+controlled release 5HT receptor agonist administered daily The study is performed using drug supplied as tablets, administered orally with water, e.g. 30 minutes after a standard meal. Matching placebo tablets are supplied.

Example 11. Effects of 5HT Receptor Agonist in Obsessive-Compulsive Disorder (OCD)

The activity of 5HT receptor agonist (e.g. psilocybin) to reduce the symptoms of OCD, administered under four dosing regimens (once daily, every other day, once weekly, and twice weekly) is investigated in a double-blind, placebo-controlled, parallel-group, randomized, 2 week study in adult volunteers with a diagnosis of OCD.

In human individuals, the study is performed in compliance with the current version of the declaration of Helsinki and with the ICH note for guidance on good clinical practice.

For human individuals, with a formal clinical diagnosis of depression, aged 20-60 years inclusive, with a body mass index (BMI) within 18-30 $kg/m^2$ inclusive, having provided a written informed consent, not using any drug treatment for 2 weeks before screening (2 months for enzyme-inducing drugs) except occasional Acetaminophen. The individuals are confined at a clinical site beginning the day before dose administration until 72 hours after final dose administration on Day 17 and return for a follow-up visit on Day 21±1.

Endpoints

The primary efficacy endpoints are:

a. Individual assessment of changes in OCD symptoms as measured on Acute Yale-Brown Obsessive-Compulsive Scale (A-YBOCS)
b. Effects on Obsessive-Compulsive symptom severity The secondary efficacy endpoints are:

a. Individual assessment of change in mood symptoms using the GRID-Hamilton
b. Recorded hallucinogenic experiences Treatment Regimen Individuals are randomized into sixteen groups:

Group 1 (n=5): Placebo administered once weekly
Group 2 (n=10): Immediate release 5HT receptor agonist administered once weekly
Group 3 (n=10): Controlled release 5HT receptor agonist administered once weekly
Group 4 (n=10): Immediate release+controlled release 5HT receptor agonist administered once weekly
Group 5 (n=5): Placebo administered twice weekly
Group 6 (n=10): Immediate release 5HT receptor agonist administered twice weekly
Group 7 (n=10): Controlled release 5HT receptor agonist administered twice weekly
Group 8 (n=10): Immediate release+controlled release 5HT receptor agonist administered twice weekly
Group 9 (n=5): Placebo administered every other day
Group 10 (n=10): Immediate release 5HT receptor agonist administered every other day Group 11 (n=10): Controlled release 5HT receptor agonist administered every other day
Group 12 (n=10): Immediate release+controlled release 5HT receptor agonist administered every other day
Group 13 (n=5): Placebo administered daily
Group 14 (n=10): Immediate release 5HT receptor agonist administered daily Group 15 (n=10): Controlled release 5HT receptor agonist administered daily
Group 16 (n=10): Immediate release+controlled release 5HT receptor agonist administered daily
The study is performed using drug, supplied as tablets, administered orally with water, e.g. 30 minutes after a standard meal. Matching placebo tablets are supplied.

Example 12. 5HT Receptor Agonist Facilitated Smoking Cessation

The ability of 5HT receptor agonist (e.g. psilocybin) to aid in smoking cessation (or to reduce nicotine dependence, or as Nicotine Replacement Therapy), administered under four dosing regimens (once daily, every other day, once weekly, and twice weekly) is investigated in a double-blind, placebo-controlled, parallel-group, randomized, 8 week study in human adults smoking an average of at least ten cigarettes daily.

The study is performed in compliance with the current version of the declaration of Helsinki and with the ICH note for guidance on good clinical practice.

Male and female individuals smoking an average of at least ten cigarettes daily, aged 20-60 years inclusive, with a body mass index (BMI) within 18-30 kg/$m^2$ inclusive, having provided a written informed consent, not using any drug treatment for 2 weeks before screening (2 months for enzyme-inducing drugs) except occasional Acetaminophen.

Endpoints

The primary efficacy endpoints are:
a. Days to first cigarette
b. Number of cigarette free days
c. Number of cigarettes per day
The secondary efficacy endpoints are:
a. Number and severity of nicotine cravings
b. Recorded hallucinogenic experiences
Individuals are randomized into sixteen groups:
Group 1 (n=5): Placebo administered once weekly
Group 2 (n=10): Immediate release 5HT receptor agonist administered once weekly
Group 3 (n=10): Controlled release 5HT receptor agonist administered once weekly
Group 4 (n=10): Immediate release+controlled release 5HT receptor agonist administered once weekly
Group 5 (n=5): Placebo administered twice weekly
Group 6 (n=10): Immediate release 5HT receptor agonist administered twice weekly
Group 7 (n=10): Controlled release 5HT receptor agonist administered twice weekly
Group 8 (n=10): Immediate release+controlled release 5HT receptor agonist administered twice weekly
Group 9 (n=5): Placebo administered every other day
Group 10 (n=10): Immediate release 5HT receptor agonist administered every other day
Group 11 (n=10): Controlled release 5HT receptor agonist administered every other day
Group 12 (n=10): Immediate release+controlled release 5HT receptor agonist administered every other day
Group 13 (n=5): Placebo administered daily
Group 14 (n=10): Immediate release 5HT receptor agonist administered daily
Group 15 (n=10): Controlled release 5HT receptor agonist administered daily
Group 16 (n=10): Immediate release+controlled release 5HT receptor agonist administered daily The study is performed using drug supplied as tablets, administered orally with water, e.g. 30 minutes after a standard meal. Matching placebo tablets are supplied.

Example 13. 5HT Receptor Agonist Facilitated Reduction in Alcohol Dependence

The ability of 5HT receptor agonist (e.g. psilocybin) to reduce alcohol dependence when administered under four dosing regimens (every other day, once weekly, twice weekly, and once every three weeks) is investigated in a double-blind, placebo-controlled, randomized, 3 month study in adult males consuming at least 5 units of alcohol daily, every day.

The study is performed in compliance with the current version of the declaration of Helsinki and with the ICH note for guidance on good clinical practice.

Adult males consuming at least 5 units of alcohol daily, every day, (where one unit of alcohol is: one single measure of spirits (ABV 37.5%); half a pint of average-strength (4%) beer or lager; one glass (85 mL) of average-strength (12%) wine), aged 25-65 years inclusive, having provided a written informed consent, not using any drug treatment for 2 weeks before screening (2 months for enzyme-inducing drugs) except occasional Acetaminophen.

Endpoints

The primary efficacy endpoints are:
a. Number of alcohol free days
b. Number of alcoholic drinks consumed per day
c. Number of heavy drinking days (defined as >4 units per day)
The secondary efficacy endpoints are:
a. Number and severity of alcohol cravings
b. Individual assessment of change in mood symptoms using the GRID-Hamilton
c. Recorded hallucinogenic experiences Treatment Regimen Individuals are randomized into sixteen groups:
Group 1 (n=5): Placebo administered every other day
Group 2 (n=10): Immediate release 5HT receptor agonist administered every other day
Group 3 (n=10): Controlled release 5HT receptor agonist administered every other day
Group 4 (n=10): Immediate release+controlled release 5HT receptor agonist administered every other day
Group 5 (n=5): Placebo administered twice weekly
Group 6 (n=10): Immediate release 5HT receptor agonist administered twice weekly
Group 7 (n=10): Controlled release 5HT receptor agonist administered twice weekly
Group 8 (n=10): Immediate release+controlled release 5HT receptor agonist administered twice weekly
Group 9 (n=5): Placebo administered once weekly
Group 10 (n=10): Immediate release 5HT receptor agonist administered once weekly
Group 11 (n=10): Controlled release 5HT receptor agonist administered once weekly
Group 12 (n=10): Immediate release+controlled release 5HT receptor agonist administered once weekly
Group 13 (n=5): Placebo administered once every three weeks
Group 14 (n=10): Immediate release 5HT receptor agonist administered
Group 15 (n=10): Controlled release 5HT receptor agonist administered
Group 16 (n=10): Immediate release+controlled release 5HT receptor agonist administered daily The study is performed using drug supplied as tablets, administered orally with water, e.g. 30 minutes after a standard meal. Matching placebo tablets are supplied.

Example 14. 5HT Receptor Agonist for the Treatment of Migraine Headache

The ability of 5HT receptor agonist (e.g. psilocybin) to treat migraine headache, administered under four dosing regimens (once daily, every other day, once weekly, and twice weekly) is investigated in a double-blind, placebo-controlled, randomized, 4 month study in adults experiencing an average of at least one migraine headache monthly.

In human individuals, the study is performed in compliance with the current version of the declaration of Helsinki and with the ICH note for guidance on good clinical practice.

Human adults, aged 20-50 years inclusive, experiencing an average of at least one migraine headache monthly, with a body mass index (BMI) within 18-30 $kg/m^2$ inclusive, having provided a written informed consent, not using any drug treatment for 2 weeks before screening (2 months for enzyme-inducing drugs).

Endpoints

The primary efficacy endpoints are:

a. Acute change in pain intensity of migraine attacks
b. Acute change in nausea/vomiting
c. Acute change in photophobia
d. Acute change in phonophobia
e. Time to first migraine attack
f. Change in migraine attack duration
g. Change in migraine attack frequency Treatment Regimen Individuals are randomized into sixteen groups:

Group 1 (n=5): Placebo administered once weekly
Group 2 (n=10): Immediate release 5HT receptor agonist administered once weekly
Group 3 (n=10): Controlled release 5HT receptor agonist administered once weekly
Group 4 (n=10): Immediate release+controlled release 5HT receptor agonist administered once weekly
Group 5 (n=5): Placebo administered twice weekly
Group 6 (n=10): Immediate release 5HT receptor agonist administered twice weekly
Group 7 (n=10): Controlled release 5HT receptor agonist administered twice weekly
Group 8 (n=10): Immediate release+controlled release 5HT receptor agonist administered twice weekly
Group 9 (n=5): Placebo administered every other day
Group 10 (n=10): Immediate release 5HT receptor agonist administered every other day Group 11 (n=10): Controlled release 5HT receptor agonist administered every other day
Group 12 (n=10): Immediate release+controlled release 5HT receptor agonist administered every other day
Group 13 (n=5): Placebo administered daily
Group 14 (n=10): Immediate release 5HT receptor agonist administered daily Group 15 (n=10): Controlled release 5HT receptor agonist administered daily
Group 16 (n=10): Immediate release+controlled release 5HT receptor agonist administered daily The study is performed using drug supplied as tablets, administered orally with water, e.g. 30 minutes after a standard meal. Matching placebo tablets are supplied.

Example 15. Effects of 5HT Receptor Agonist Facilitated Treatment for Opioid Use The effectiveness of 5HT receptor agonist (e.g. psilocybin) in treating opioid dependent individuals, administered under four dosing regimens (once daily, every other day, once weekly, and twice weekly) is investigated in a double-blind, placebo-controlled, parallel-group, randomized, 16 week study in opioid dependent adults.

In human individuals, the study is performed in compliance with the current version of the declaration of Helsinki and with the ICH note for guidance on good clinical practice.

Male and female individuals actively using one or more opioids (e.g. prescription opioids, such as oxycodone, hydrocodone, fentanyl, tramadol, or illegal opioids, such as heroin), aged 18-55 years inclusive, with a body mass index (BMI) within 18-30 $kg/m^2$ inclusive, having provided a written informed consent, nonsmokers for at least 6 months.

Endpoints

The primary efficacy endpoints are:

a. Incidence of opioid use (assessed by urine analysis)
b. Longest duration of abstinence
c. Number of abstinence days
d. Number of participants retained in study
e. Number of abstinent participants The secondary efficacy endpoints are:

a. Number and severity of drug cravings
b. Recorded hallucinogenic experiences

Individuals are randomized into sixteen groups:

Group 1 (n=5): Placebo administered once weekly
Group 2 (n=10): Immediate release 5HT receptor agonist administered once weekly
Group 3 (n=10): Controlled release 5HT receptor agonist administered once weekly
Group 4 (n=10): Immediate release+controlled release 5HT receptor agonist administered once weekly
Group 5 (n=5): Placebo administered twice weekly
Group 6 (n=10): Immediate release 5HT receptor agonist administered twice weekly
Group 7 (n=10): Controlled release 5HT receptor agonist administered twice weekly
Group 8 (n=10): Immediate release+controlled release 5HT receptor agonist administered twice weekly
Group 9 (n=5): Placebo administered every other day
Group 10 (n=10): Immediate release 5HT receptor agonist administered every other day
Group 11 (n=10): Controlled release 5HT receptor agonist administered every other day
Group 12 (n=10): Immediate release+controlled release 5HT receptor agonist administered every other day
Group 13 (n=5): Placebo administered daily
Group 14 (n=10): Immediate release 5HT receptor agonist administered daily
Group 15 (n=10): Controlled release 5HT receptor agonist administered daily
Group 16 (n=10): Immediate release+controlled release 5HT receptor agonist administered daily The study is performed using drug supplied as tablets, administered orally with water, e.g. 30 minutes after a standard meal. Matching placebo tablets are supplied.

Example 16: 5HT Receptor Agonist in the Treatment of Cocaine Use Disorder (CUD)

The effectiveness of 5HT receptor agonist (e.g. psilocybin) to reduce cocaine use in patients diagnosed with CUD administered under four dosing regimens (once daily, every other day, once weekly, and twice weekly) is investigated in a double-blind, placebo-controlled, parallel-group, randomized, 16 week study in adults diagnosed with CUD.

In human individuals, the study is performed in compliance with the current version of the declaration of Helsinki and with the ICH note for guidance on good clinical practice.

For human individuals, with a clinical diagnosis of CUD, aged 18-65 years inclusive, with a body mass index (BMI) within 18-30 kg/$m^2$ inclusive, having provided a written informed consent, non-smokers for at least 6 months, not using any drug treatment for 2 weeks before screening (2 months for enzyme-inducing drugs) except occasional acetaminophen and cocaine.

Endpoints

The primary efficacy endpoint is:

a. The difference between treatment and placebo groups in the number of participants demonstrating cocaine abstinence The secondary efficacy endpoints are:

b. Recorded hallucinogenic experiences

Treatment Regimen

Individuals are randomized into sixteen groups:

Group 1 (n=5): Placebo administered once weekly

Group 2 (n=10): Immediate release 5HT receptor agonist administered once weekly

Group 3 (n=10): Controlled release 5HT receptor agonist administered once weekly Group 4 (n=10): Immediate release+controlled release 5HT receptor agonist administered once weekly Group 5 (n=5): Placebo administered twice weekly Group 6 (n=10): Immediate release 5HT receptor agonist administered twice weekly Group 7 (n=10): Controlled release 5HT receptor agonist administered twice weekly Group 8 (n=10): Immediate release+controlled release 5HT receptor agonist administered twice weekly Group 9 (n=5): Placebo administered every other day Group 10 (n=10): Immediate release 5HT receptor agonist administered every other day Group 11 (n=10): Controlled release 5HT receptor agonist administered every other day Group 12 (n=10): Immediate release+controlled release 5HT receptor agonist administered every other day Group 13 (n=5): Placebo administered daily Group 14 (n=10): Immediate release 5HT receptor agonist administered daily Group 15 (n=10): Controlled release 5HT receptor agonist administered daily Group 16 (n=10): Immediate release+controlled release 5HT receptor agonist administered daily The study is performed using drug supplied as tablets, administered orally with water, e.g. 30 minutes after a standard meal. Matching placebo tablets are supplied.

Example 17: Psilocybin Dose and Efficacy Studies

Dose Finding Experiments

Psilocybin was tested at a dose range of 0.03-10.0 mg/kg administered sub-cutaneously (S.C.) Behavioral syndrome including wet dog shakes (WDS) and back muscle contractions (BMC) are characteristic of 5-$HT_{2A}$ receptor activity and potentially indicative of psychomotor signs. Psilocybin dosed 0.03-0.1 mg/kg S.C. produced no signs of behavioral syndrome, whereas doses of 0.3 mg/kg I.P and higher produced significant signs of behavior syndrome. These results suggest that a dose range of 0.03-0.1 mg/kg S.C. is preferred for examining procognitive or motivational-enhancing effects of psilocybin (FIG. 1). There is a parallel between behaviors such as WDS in rats and hallucination in humans (Behavioral Neurobiology of Psychedelic Drugs, Halberstadt, Adam, Vollenweider, Franz X., Nichols, David E. (Eds.), Springer, 2018, p 161).

Compared with stimulant drugs, low doses of psilocybin produce a mild stimulant effect, with distance travelled at low doses producing increases of ~0.3-0.4 fold in distance travelled (FIG. 2A) and high doses showing slightly decreased distanced travelled. Stimulant drugs cause far larger increases in distance travelled with escalating doses, reflective of a direct motor stimulant property not seen with psilocybin.

Efficacy Studies

Experiments were conducted to test psilocybin doses in the range of 0.05-0.2 mg/kg psilocybin administered S.C. across progressive ratio (PR) and 5-choice serial reaction time task (5CSRTT) to examine the effect of psilocybin on endophenotypes of motivation and attention. In each study, a population of out-bred Long Evans rats was first tested as a group for response to the PR and 5CSRTT. Each group was then divided into sub-groups by tertiles according to performance, and then exposed to various dose levels immediately prior to re-testing at various psilocybin dose levels. As explained below, rats in the lowest tertile sub-group displayed different responses than rats in the highest tertile.

The PR test is used to answer how willing the test subject is to work for food (i.e. test of motivation). A single 45 mg food pellet (i.e. reinforcer) is made available to the test animal based on lever press response. To obtain each successive pellet, the animal must make increasingly more lever presses. Typically, a progression of 2, 4, 6, 9, 12, 15, 20, 25, 32, 40, 50, 62, 77, 95, 118, etc. is used, derived from the equation:

$$\text{ratio} = \left[5 \times e^{(02 \times reinforcer\ \#)} - 5\right]$$

Hungry test animals do not find 45 mg food pellets sufficient and, therefore, there is a drive to repeatedly lever press to obtain multiple food pellets. At some point, the animal gives up as the motor demands to obtain a single pellet are not deemed worthwhile (i.e. animal reaches "break point" defined as animal's failure to earn a food pellet in 20 minutes).

Psilocybin was administered to rats S.C. at doses of 0.05, 0.1 and 0.2 mg/kg. None of these doses were observed to cause obvious changes in the number of lever presses or break points (i.e. rewards earned) when studied across entire study population of 36 rats.

Figure 2:
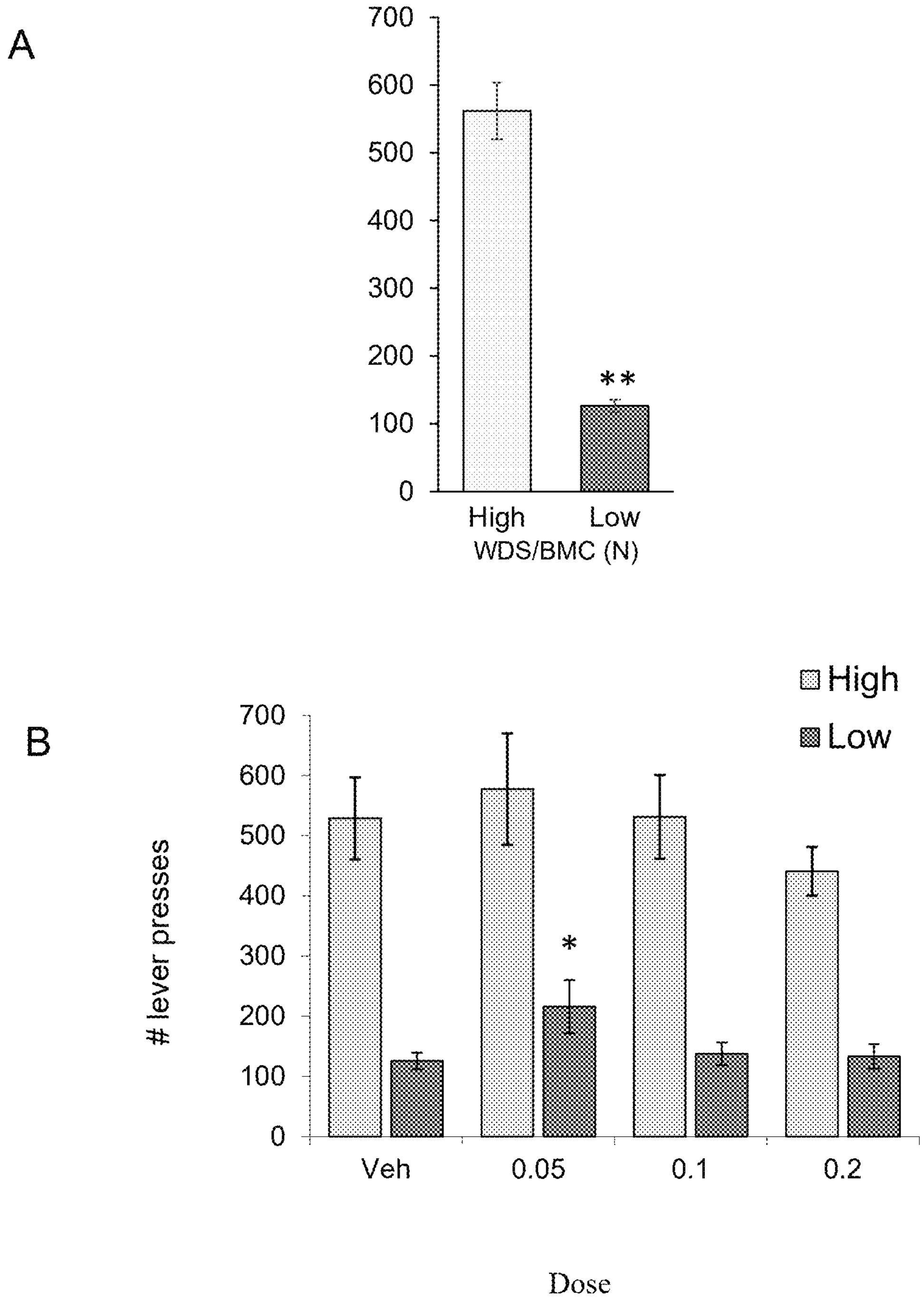
FIG. 2 shows the effects of psilocybin on progressive ratio (PR) test in treated rats. A) Graph shows number of lever presses prior to treatment with vehicle or psilocybin, by high and low responder rat groups, to establish pre-test PR baseline. B) Graph shows number of lever presses by high and low responder rat subgroups across psilocybin doses of 0.05 mg/kg, 0.1 mg/kg and 0.2 mg/kg. High responders are defined as rats completing the highest tertile of lever presses in the baseline test; low responders are rats completing the bottom tertile of lever presses in the baseline test. Asterisk (*) indicates statistical significance between high and low responders.

Rats were then sub-grouped into tertiles based on the number of lever presses for food at baseline, so that within the test population of 36 animals, 12 animals were identified as low responders, characterized by low motivation and potentially corresponding to low motivation endophenotype representative of clinical depression. Twelve animals were identified as high responders. There was a statistically significant difference between the high and low responders. Psilocybin doses of 0.05-0.2 mg/kg administered S.C. were observed to produce no effect on response in high responder subgroup (FIG. 2). However, 0.05 mg/kg psilocybin was observed to produce an increase in food responding in low responder subgroup, whereas the dose of 0.1 mg/kg did not produce an increase in food responding. This represents a motivational enhancing effect of psilocybin in the cohort corresponding to a low motivation endophenotype representative of clinical depression.

The 5CSRTT involves evaluating test subject response to a brief visual stimulus (Higgins, Guy & Silenieks, Leonardo. (2017). Rodent Test of Attention and Impulsivity: The 5-Choice Serial Reaction Time Task: The 5-Choice Serial Reaction Time Task. 10.1002/cpph.27). Animals are trained to make a nose-poke response to a stimulus location in order to collect a food reward. The task allows the experimenter to measure animal performance in multiple domains including:

- Attention
- Impulsivity
- Perseveration
- Speed of response

Figure 3:
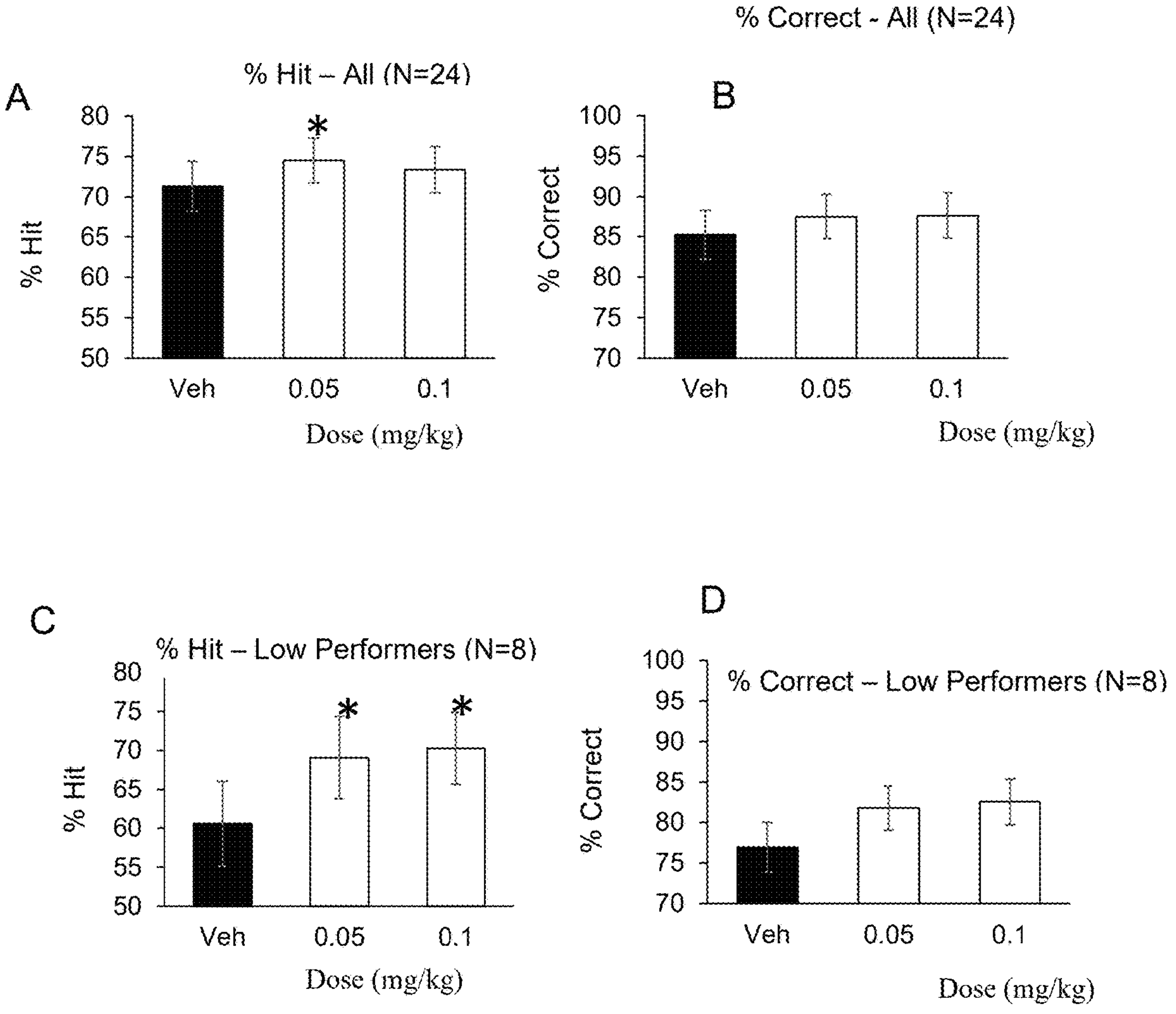
FIG. 3 shows the effects of psilocybin on cognition in rats using the 5-choice serial reaction time task (5-CSRTT) with 5 second inter-trial interval. A) Graph shows pro-cognitive effects (measured as % Hit regarding nose-poke to stimulation location to collect a food reward) of psilocybin 0.05 mg/kg dose versus vehicle and 0.1 mg/kg dose across all rats. Asterisk (*) indicates statistical difference vs. vehicle. B) Graph shows pro-cognitive effects (measured as % Correct regarding accuracy in nose-poke) of psilocybin 0.05 mg/kg dose versus vehicle and 0.1 mg/kg dose across all rats. C) Graph shows pro-cognitive effect of two different doses of psilocybin on low performer subgroup (% Hit). Asterisk (*) indicates statistical difference vs. vehicle D) Graph shows effect of two different doses of psilocybin on low performer subgroup (% Correct). High performers are defined as rats completing the highest tertile of Hits or Correct nose-pokes in the baseline test; low performers are rats completing the bottom tertile of Hits or Correct nose-pokes in the baseline test.

A strength of the test is its flexible configuration to challenge test subjects:

- Standard test conditions (0.75 s stimulus duration (SD), 5 s inter-trial interval (ITI), 100 trials)
- Multiple short stimulus duration (mSD) (0.03-1 s SD)
- Fixed long ITI (5 s vs. 10 s ITI)
- Multiple ultrashort ITI (2-5 s ITI)
- Extended 250 trials Psilocybin dose of 0.05 mg/kg administered S.C. was observed to produce an increased (p=0.05, t-test) pro-cognitive effect (measured as % hit, calculated as #correct/(#correct+#incorrect+#omissions)*100) when studied across a study population of 24 rats in a 5CSRTT with standard conditions, i.e., 75 s SD, 5 S ITI, 100 trials. Asterisk (*) indicates statistical significance vs. vehicle. (FIG. 3A). There was a slight non-significant increase in procognitive effect (measured as % correct, calculated as #correct/(#correct+ #incorrect)*100 (FIG. 3B). There was no effect on performance, e.g no effect on response speed, or number of trials completed. There was no effect on premature or perseverative responses in this experiment.

Figure 6:
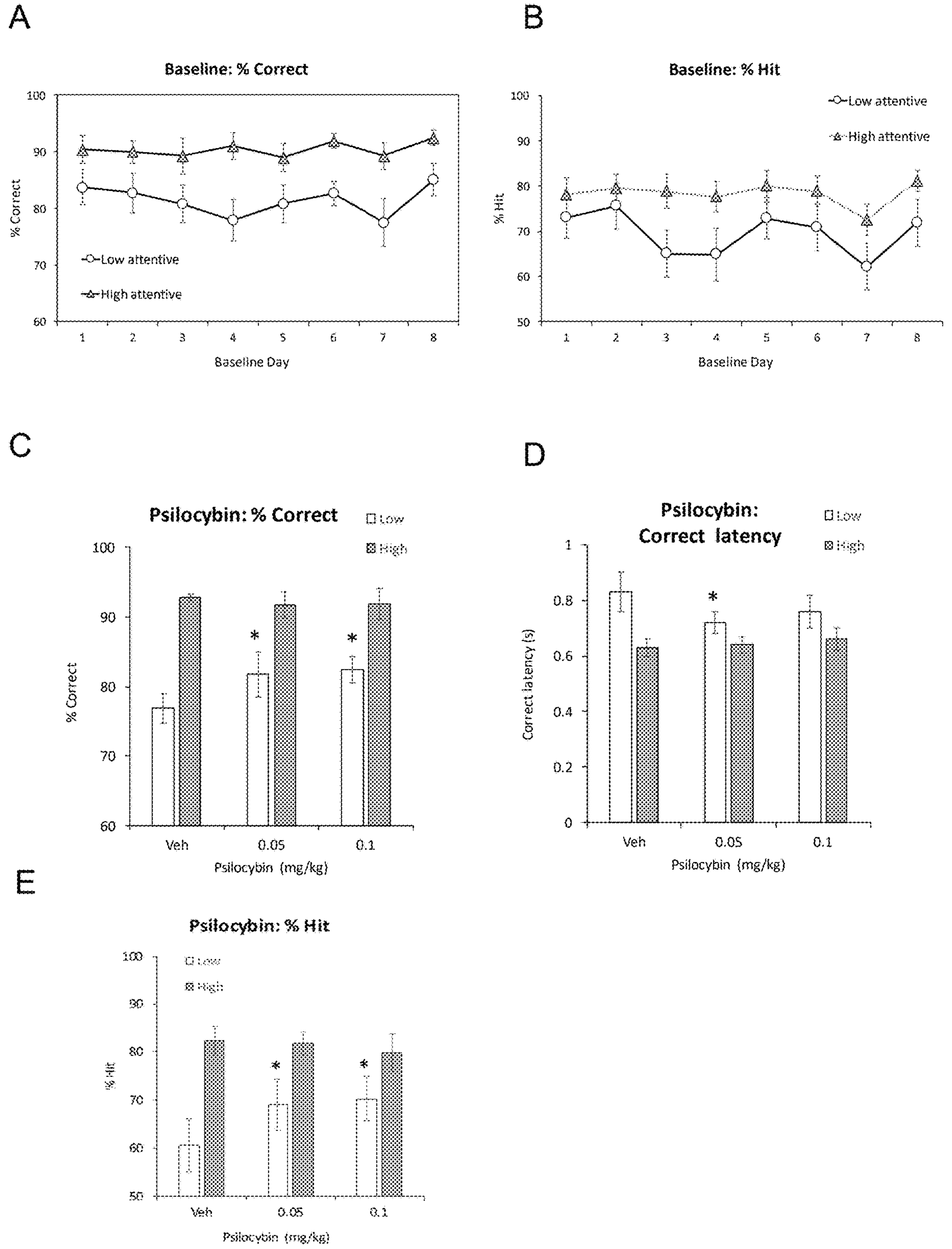
FIG. 6 shows the effects of psilocybin on cognition in rats. A) Graph shows the lowest performing tertile (N=8) low attentive and potentially representative of a low attentive endophenotype of depression. B) Graph shows % hit score for low attentive rats. D) Graph shows a slower response speed for low attentive rats. Similar to the PR test, the effect of 0.05 and 0.1 mg/kg psilocybin on accuracy (% correct and % hit) in the 5CSRTT was observed to be strongly evident in the low attentive subgroup compared with vehicle C) graph and E) graph. Asterisk (*) indicates statistical significance vs. vehicle. Psilocybin 0.05 mg/kg also increased response speed in the low attentive cohort compared with vehicle D) graph.

When this population is segmented into tertiles according to performance based on accuracy (% correct, calculated as #correct/(#correct+ #incorrect)*100), the lowest performing tertile (N=8) are considered to be low attentive and potentially representative of a low attentive endophenotype of depression (FIG. 6A). Low attentive rats also score poorly on % hit (FIG. 6B) and have a slower response speed (FIG. 6D). Similar to the PR test, the effect of 0.05 and 0.1 mg/kg psilocybin on accuracy (% correct and % hit) in the 5CSRTT was observed to be strongly evident in the low attentive subgroup compared with vehicle (FIGS. 6C and 6E). Asterisk (*) indicates statistical significance vs. vehicle. Psilocybin 0.05 mg/kg also increased response speed in the low attentive cohort compared with vehicle (FIG. 6D).

Figure 4:
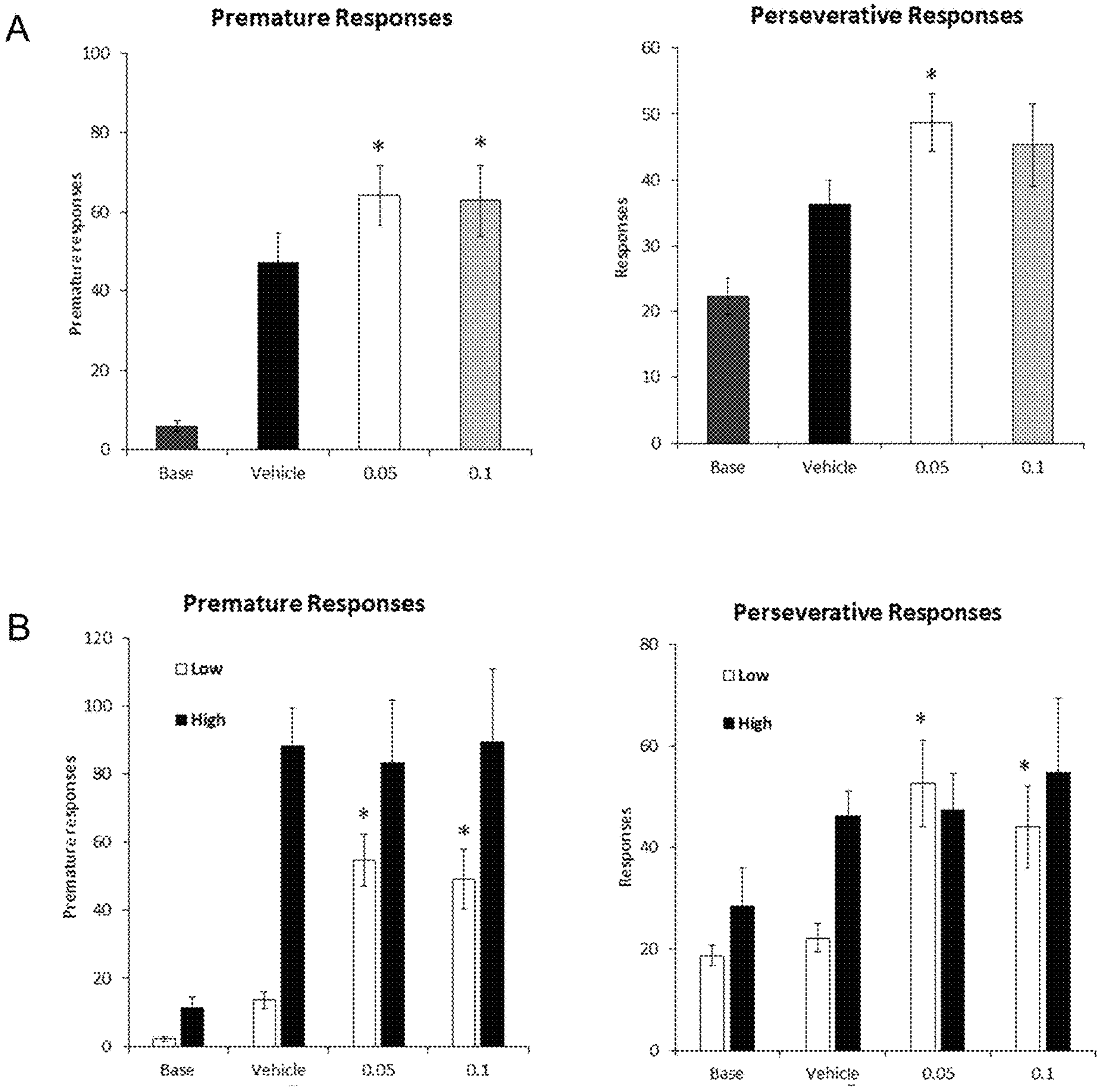
FIG. 4 shows the effects of psilocybin on cognition in rats using 5-choice serial reaction time task (5-CSRTT) and evaluating premature responses (PREM) and perseverative responses (PSV). A) Graphs show increase in PREM and PSV responses under a 5 second inter-trial interval (ITI) which establishes a baseline (Base) and a 10 second ITI across 24 animals across two doses of psilocybin (0.05 mg/kg and 0.1 mg/kg). Standard deviation is indicated by error bars; asterisks (*) indicate significance vs. vehicle (P=0.05) using T-test. B) Graphs show effects of psilocybin on PREM and PSV in low performer and high performer subgroups. Standard error of the mean is indicated by error bars; asterisks (*) indicate significance vs. vehicle ($P<0.01$) using T-test. High performers are defined as rats with the highest tertile of premature responses in the baseline test; low performers are rats with the bottom tertile of premature responses in the baseline test.

Using a longer duration between stimulus and reward, the 5CSRTT study measures premature (PREM) and perseverant (PSV) responses. PREM/PSV responses were increased by increasing the ITI from 5 s (baseline) to 10 s (test condition). A psilocybin dose of 0.05 mg/kg administered S.C. was observed to produce an increase (p=0.05, t-test) increase in PREM and PSV responses under a 10 s ITI when studied across a study population of 24 rats (FIG. 4A). Low responders (N=8) were observed to improve significantly from psilocybin administration at both 0.05 and 0.1 mg/kg doses (FIG. 4B, p<0.01, t-test), with marked increases in premature responses and perseverative responses in rats in that sub-group compared with vehicle. Both PREM and PSV behaviors are examples of executive cognitive function, likely involving areas of the prefrontal cortex, a brain region rich in $5\text{-HT}_{2A}$ receptors.

At doses that did not produce effects in animals indicative of hallucination, improved results were seen on low performing animals on measures of motivation, attention, accuracy, speed of response, perseveration, and cognitive engagement. The improvement in the low performing animals indicates utility of non-hallucinogenic doses of psilocybin in treatment of behavioral and cognitive disorders involving these behaviors, including but not limited to depression, anxiety, apathy and low motivation, attention disorders, disorders of executive function and cognitive engagement, obsessive compulsive disorder, and neurocognitive disorders. At these same doses, no detrimental effects of psilocybin were noted on performance, i.e. there was no evidence of reduced motivation, impaired motor control, or impaired attention or response speed. The positive effects of the low doses of psilocybin appear most evident in the low performer subgroups based on three tests: one PR (motivation) and two 5CSRTT (attention) studies were conducted, using psilocybin at 0.05-0.2 mg/kg (PR) and 0.05-0.1 mg/kg S.C. (5CSRTT). Significant improvements were noted in the low performing animals on:

- Number of lever presses and increased break point in PR test (0.05 mg/kg)
- % Correct and % Hit in 5CSRTT (0.05 and 0.1 mg/kg)
- Increased speed of responding in 5CSRTT (0.05 mg/kg)
- PREM/PSV in 5CSRTT 10 s ITI (0.05 and 0.1 mg/kg

Example 18: Psilocybin and Psilocin Pharmacokinetics (PK)

Figure 5:
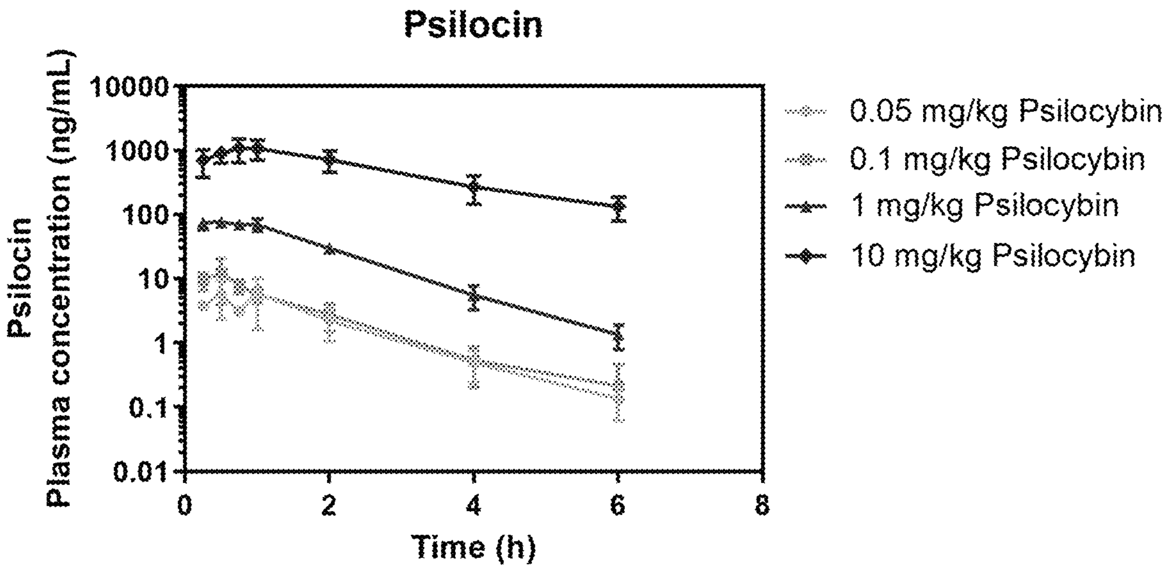
FIG. 5 shows the blood plasma levels over time of psilocin in rats dosed with psilocybin at several dose levels: 0.05 mg/kg ($C_{max}$ psilocin ~6±2 ng/ml (after 30 mins)) or 0.1 mg/kg ($C_{max}$ psilocin ~12±3 ng/ml (after 30 mins)), 1 mg/kg ($C_{max}$ psilocin ~83±5 ng/ml (after 30 mins)), 10 mg/kg ($C_{max}$ psilocin ~1106±164 ng/ml (after 30 mins)).

Psilocybin doses of 0.05, 0.1, 1, 10 mg/kg were used to evaluate psilocybin and psilocin PK in rats. For the doses of psilocybin that positively effect behaviors in the low performers in the PR and 5CSRTT, i.e. 0.05-0.1 mg/kg, the corresponding $C_{max}$ of psilocin was ~7±2 ng/ml at 30 minutes for 0.05 mg/kg, and at a dose of 0.1 mg/kg, the $C_{max}$ of psilocin was determined to be ~12±3 ng/ml at 30 minutes (FIG. 5).

Details of the plasma concentration studies are shown in Tables 1-8 (psilocybin) and 9-16 (psilocin). Values in italics are below the lower level of quantitation (BLQ, <1 ng/mL) but were included in calculations. Values in bold and underlined are considered to be outliers and were omitted from calculations. Measured dosing solution concentrations were 0.0460, 0.0967, 0.948 and 9.65 mg/mL for 0.05, 0.1, 1 and 10 mg/mL respectively.

TABLE 1

Plasma concentrations of psilocybin following 0.05 mg/kg s.c. administration.

| Experimental time (h) | Plasma concentration (ng/mL) Mean | SD |
|---|---|---|
| 0.25 | 6.20 | 7.27 |
| 0.5 | 12.5 | 16.9 |
| 0.75 | 1.07 | 0.348 |
| 1 | 19.2 | 26.3 |
| 2 | 0.594 | n/a |
| 4 | 1.95 | 0.508 |
| 6 | 2.12 | n/a |

n/a = not applicable

TABLE 2

Plasma concentration of psilocybin following 0.1 mg/kg s.c. administration.

| Experimental time (h) | Plasma concentration (ng/mL) Mean | SD |
|---|---|---|
| 0.25 | 21.7 | 27.4 |
| 0.5 | 28.9 | 45.0 |
| 0.75 | 2.96 | 1.32 |
| 1 | 2.19 | 0.605 |
| 2 | 1.76 | n/a |
| 4 | 2.55 | n/a |
| 6 | 0.921 | n/a |

TABLE 3

Plasma concentration of psilocybin following 1.0 mg/kg s.c. administration

| Experimental time (h) | Plasma concentration (ng/mL) Mean | SD |
|---|---|---|
| 0.25 | 75.2 | 39.8 |
| 0.5 | 47.3 | 24.4 |
| 0.75 | 35.8 | 13.2 |
| 1 | 35.1 | 30.4 |
| 2 | 2.19 | 1.26 |
| 4 | 1.12 | n/a |
| 6 | 0.929 | n/a |

TABLE 4

Plasma concentration of psilocybin following 10 mg/kg s.c. administration.

| Experimental time (h) | Plasma concentration (ng/mL) Mean | SD |
|---|---|---|
| 0.25 | 1030 | 832 |
| 0.5 | 1544 | 1898 |
| 0.75 | 344 | 132 |
| 1 | 269 | 93.4 |
| 2 | 101 | 172 |
| 4 | 1.80 | 0.985 |
| 6 | 1.32 | 1.02 |

TABLE 5

Plasma PK parameters summary for psilocybin following 0.05 mg/kg s.c. administration.

| Parameter | Mean | SD |
|---|---|---|
| $t_{max}$ (h) | 0.600 | 0.379 |
| $C_{max}$ (ng/mL) | 18.9 | 20.9 |
| $C_{max}$/Dose (kg*ng/mL/mg) | 377 | 419 |
| Apparent $t_{1/2}$ (h) | n/a[b] | n/a |
| $AUC_{0-tlast}$ (h*ng/mL) | 10.7 | 7.08 |
| $AUC_{0-inf}$ (h*ng/mL) | n/a | n/a |
| $AUC_{0-inf}$/Dose (h*kg*ng/mL/mg) | n/a | n/a |
| $MRT_{0-inf}$ (h) | n/a | n/a |

n/a = not applicable $T_{max}$ = time at which maximum concentration is observed $C_{max}$ = maximum observed concentration Apparent $t_{1/2}$ = apparent terminal half-life $AUC_{0-tlast}$ = Area Under the Concentration vs time curve from time 0 to the time of the last measurable concentration $AUC_{0-inf}$ = Area Under the Concentration vs time curve from time to infinity $MRT_{0-inf}$ = Mean Residence Time from time zero to infinity

TABLE 6

Plasma PK parameters summary for psilocybin following 0.1 mg/kg s.c. administration.

| Parameter | Mean | SD |
|---|---|---|
| $t_{max}$ (h) | 0.321 | 0.122 |
| $C_{max}$ (ng/mL) | 31.4 | 39.9 |
| $C_{max}$/Dose (kg*ng/mL/mg) | 314 | 399 |
| Apparent $t_{1/2}$ (h) | n/a[b] | n/a |
| $AUC_{0-tlast}$ (h*ng/mL) | 11.4 | 11.9 |
| $AUC_{0-inf}$ (h*ng/mL) | n/a | n/a |
| $AUC_{0-inf}$/Dose (h*kg*ng/mL/mg) | n/a | n/a |
| $MRT_{0-inf}$ (h) | n/a | n/a |

TABLE 7

Plasma PK parameters summary for psilocybin following 1.0 mg/kg s.c. administration.

| Parameter | Mean | SD |
|---|---|---|
| $t_{max}$ (h) | 0.357 | 0.283 |
| $C_{max}$ (ng/mL) | 78.3 | 39.8 |
| $C_{max}$/Dose (kg*ng/mL/mg) | 78.3 | 39.8 |
| Apparent $t_{1/2}$ (h) | 0.445 | 0.236 |
| $AUC_{0-tlast}$ (h*ng/mL) | 53.1 | 23.7 |
| $AUC_{0-inf}$ (h*ng/mL) | 47.9 | 17.6 |
| $AUC_{0-inf}$/Dose (h*kg*ng/mL/mg) | 47.9 | 17.6 |
| $MRT_{0-inf}$ (h) | 0.746 | 0.186 |

TABLE 8

Plasma PK parameters summary for psilocybin following 10 mg/kg s.c. administration.

| Parameter | Mean | SD |
|---|---|---|
| $t_{max}$ (h) | 0.500 | 0.289 |
| $C_{max}$ (ng/mL) | 3595 | 4663 |
| $C_{max}$/Dose (kg*ng/mL/mg) | 359 | 466 |
| Apparent $t_{1/2}$ (h) | 0.566 | 0.189 |
| $AUC_{0-tlast}$ (h*ng/mL) | 1707 | 2338 |
| $AUC_{0-inf}$ (h*ng/mL) | 2156 | 2704 |
| $AUC_{0-inf}$/Dose (h*kg*ng/mL/mg) | 216 | 270 |
| $MRT_{0-inf}$ (h) | 0.716 | 0.175 |

TABLE 9

Plasma concentrations of psilocin following 0.05 mg/kg s.c. administration of psilocybin.

| Experimental time (h) | Plasma concentration (ng/mL) Mean | SD |
|---|---|---|
| 0.25 | 3.76 | 0.560 |
| 0.5 | 5.68 | 3.38 |
| 0.75 | 3.11 | 0.245 |
| 1 | 5.91 | 4.31 |
| 2 | 2.23 | 1.18 |
| 4 | 0.490 | 0.253 |
| 6 | 0.136 | 0.0749 |

TABLE 10

Plasma concentrations of psilocin following 0.1 mg/kg s.c. administration of psilocybin.

| Experimental time (h) | Plasma concentration (ng/mL) Mean | SD |
|---|---|---|
| 0.25 | 9.35 | 2.79 |
| 0.5 | 12.3 | 8.29 |
| 0.75 | 7.73 | 1.87 |
| 1 | 5.70 | 1.52 |
| 2 | 2.78 | n/a |
| 4 | 0.535 | n/a |
| 6 | 0.215 | n/a |

TABLE 11

Plasma concentrations of psilocin following 1 mg/kg s.c. administration of psilocybin.

| Experimental time (h) | Plasma concentration (ng/mL) Mean | SD |
|---|---|---|
| 0.25 | 74.5 | 16.7 |
| 0.5 | 76.6 | 11.1 |
| 0.75 | 70.3 | 7.05 |
| 1 | 69.9 | 15.5 |
| 2 | 29.7 | 4.76 |
| 4 | 5.50 | 2.21 |
| 6 | 1.34 | 0.551 |

TABLE 12

Plasma concentrations of psilocin following 10 mg/kg s.c. administration of psilocybin.

| Experimental time (h) | Plasma concentration (ng/mL) Mean | SD |
|---|---|---|
| 0.25 | 704 | 327 |
| 0.5 | 898 | 266 |
| 0.75 | 1081 | 437 |
| 1 | 1067 | 367 |
| 2 | 713 | 255 |
| 4 | 269 | 126 |
| 6 | 132 | 53.3 |

TABLE 13

Plasma PK parameters summary for psilocin following 0.05 mg/kg s.c. administration of psilocybin.

| Parameter | Mean | SD |
|---|---|---|
| $t_{max}$ (h) | 0.600 | 0.379 |
| $C_{max}$ (ng/mL) | 7.14 | 4.02 |
| Apparent $t_{1/2}$ (h) | 1.00 | 0.227 |
| $AUC_{0-tlast}$ (h*ng/mL) | 10.1 | 3.96 |
| $AUC_{0-inf}$ (h*ng/mL) | 10.3 | 3.92 |
| $MRT_{0-inf}$ (h) | 1.73 | 0.177 |

TABLE 14

Plasma PK parameters summary for psilocin following 0.1 mg/kg s.c. administration of psilocybin.

| Parameter | Mean | SD |
|---|---|---|
| $t_{max}$ (h) | 0.536 | 0.267 |
| $C_{max}$ (ng/mL) | 11.7 | 6.81 |
| Apparent $t_{1/2}$ (h) | 0.918 | 0.22 |
| $AUC_{0-tlast}$ (h*ng/mL) | 12.5 | 6.42 |
| $AUC_{0-inf}$ (h*ng/mL) | 15.7 | 5.56 |
| $MRT_{0-inf}$ (h) | 1.42 | 0.337 |

TABLE 15

Plasma PK parameters summary for psilocin following 1 mg/kg s.c. administration of psilocybin.

| Parameter | Mean | SD |
|---|---|---|
| $t_{max}$ (h) | 0.571 | 0.313 |
| $C_{max}$ (ng/mL) | 83.3 | 14.4 |
| Apparent $t_{1/2}$ (h) | 0.878 | 0.0762 |
| $AUC_{0-tlast}$ (h*ng/mL) | 117 | 45.2 |
| $AUC_{0-inf}$ (h*ng/mL) | 143 | 20.4 |
| $MRT_{0-inf}$ (h) | 1.53 | 0.110 |

TABLE 16

Plasma PK parameters summary for psilocin following 10 mg/kg s.c. administration of psilocybin.

| Parameter | Mean | SD |
|---|---|---|
| $t_{max}$ (h) | 0.714 | 0.267 |
| $C_{max}$ (ng/mL) | 1106 | 434 |
| Apparent $t_{1/2}$ (h) | 1.65 | 0.325 |
| $AUC_{0-tlast}$ (h*ng/mL) | 2280 | 1524 |
| $AUC_{0-inf}$ (h*ng/mL) | 3376 | 1056 |
| $MRT_{0-inf}$ (h) | 2.66 | 0.395 |

While preferred embodiments have been shown and described herein, it will be obvious to those skilled in the art that such embodiments are provided by way of example only. Numerous variations, changes, and substitutions will now occur to those skilled in the art without departing from this disclosure. It should be understood that various alternatives to the embodiments described herein might be employed in practicing current disclosure.

NUMBERED EMBODIMENTS

Embodiment 1 is a pharmaceutical composition comprising:

a) a therapeutically effective amount of one or more 5HT receptor agonist or a pharmaceutically acceptable salt, solvate, metabolite, derivative, or prodrug thereof, b) a pharmaceutically acceptable excipient, and c) optionally one or more agents selected from the group consisting of surfactants, preservatives, flavoring agents, sweetening agents, and antifoaming agents.

Embodiment 2 is the pharmaceutical composition of embodiment 1, wherein the pharmaceutical composition is a low-dose pharmaceutical composition.

Embodiment 3 is the pharmaceutical composition of embodiment 2, wherein the therapeutically effective amount of 5HT receptor agonist or a pharmaceutically acceptable salt, solvate, metabolite, derivative, or prodrug thereof is present in an amount insufficient to provide an adverse side effect, such as hallucinogenic experience.

Embodiment 4 is the pharmaceutical composition of either one of embodiments 2 or 3, wherein following administration to an individual in need thereof, the low-dose pharmaceutical composition provides a maximum plasma concentration ($C_{max}$) of the 5HT receptor agonist or a pharmaceutically acceptable salt, solvate, metabolite, derivative, or prodrug thereof of less than 6 ng/mL in the individual in need thereof.

Embodiment 5 is the pharmaceutical composition of any one of the preceding embodiments, wherein following administration to an individual in need thereof, the low-dose pharmaceutical composition provides a maximum plasma concentration ($C_{max}$) of the 5HT receptor agonist or a pharmaceutically acceptable salt, solvate, metabolite, derivative, or prodrug thereof of at least 0.5 ng/ml and less than 6 ng/ml in the individual in need thereof (e.g. about 1 ng/ml to about 5.5 ng/ml, about 2 ng/ml to about 5 ng/mL, or the like).

Embodiment 6 is the pharmaceutical composition of any one of the preceding embodiments, wherein the pharmaceutical composition comprises a controlled release component.

Embodiment 7 is the pharmaceutical composition of any one of the preceding embodiments, wherein following administration to an individual in need thereof, the pharmaceutical composition provides a minimum plasma concentration ($C_{min}$) of the 5HT receptor agonist or a pharmaceutically acceptable salt, solvate, metabolite, derivative, or prodrug thereof of about 0.1 ng/ml or more in the individual, wherein the minimum plasma concentration ($C_{min}$) is determined at a time between 2 hours and 12 hours (or between 2 hours and 24 hours, or between 2 hours and 48 hours, or between 2 hours and 72 hours, or the like) after administration to the individual.

Embodiment 8 is the pharmaceutical composition of any one of the preceding embodiments, wherein following administration to an individual in need thereof, the pharmaceutical composition provides a minimum plasma concentration ($C_{min}$) of the 5HT receptor agonist or a pharmaceutically acceptable salt, solvate, metabolite, derivative, or prodrug thereof of about 0.1 ng/mL to about 0.5 ng/mL in the individual, wherein the minimum plasma concentration ($C_{min}$) is determined at a time between 2 hours and 12 hours (or between 2 hours and 24 hours, or between 2 hours and 48 hours, or between 2 hours and 72 hours, or the like) after administration to the individual.

Embodiment 9 is the pharmaceutical composition of any one of the preceding embodiments, wherein the pharmaceutical composition comprises a controlled release component and an immediate release component.

Embodiment 10 is the pharmaceutical composition of any one of the preceding embodiments, wherein the pharmaceutical composition is an oral formulation, a buccal formulation, a nasal formulation, or an inhalation formulation.

Embodiment 11 is the pharmaceutical composition of any one of the preceding embodiments, wherein the pharmaceutically acceptable excipient comprises water, purified water, saline, liposome, mineral oil, alcohol, or any combination thereof.

Embodiment 12 is the pharmaceutical composition of any one of the preceding embodiments, wherein the composition further comprises an effective amount of a vasoconstrictor.

Embodiment 13 is the pharmaceutical composition of embodiment 12, wherein the vasoconstrictor is epinephrine, phenylephrine, methoxamine, norepinephrine, zolmitriptan, tetrahydrozaline, naphazoline, or combinations thereof.

Embodiment 14 is the pharmaceutical composition of any one of embodiments 1-13, wherein the composition further comprises an effective amount of a stimulant, an antihistamine, an antiemetic, an antidepressant, an anti-inflammatory, a growth factor, a lithium compound, resveratrol, phosphatidylcholine, curcumin, magnesium, melatonin, pregnenolone, ginseng, tryptophan, lysergic acid diethylamide, a 5HT receptor antagonist, or combinations thereof.

Embodiment 15 is the pharmaceutical composition of any one of the preceding embodiments, wherein said composition is in a form selected from a spray, aerosol, mist, nebulae, ointment, cream, gel, paste, salve, solution, suspension, tincture, patch, and atomized vapor.

Embodiment 16 is the pharmaceutical composition of any one of the preceding embodiments, wherein the 5HT receptor agonist or a pharmaceutically acceptable salt, solvate, metabolite, derivative, or prodrug thereof is present in an amount of about 0.1 mg to about 50 mg (e.g. about 0.1 mg to about 10 mg, or about 0.2 mg to about 5 mg.

Embodiment 17 is the pharmaceutical composition of any one of the preceding embodiments, further comprising a controlled release matrix.

Embodiment 18 is the pharmaceutical composition of embodiment 17, wherein the maximum plasma concentration is between about 2 ng/ml and 6 ng/ml.

Embodiment 19 is the pharmaceutical composition of embodiment 17, wherein the maximum plasma concentration is between about 2 ng/ml and about 5 ng/ml.

Embodiment 20 is the pharmaceutical composition of embodiment 17, wherein the maximum plasma concentration is between about 4 ng/ml and 6 ng/ml.

Embodiment 21 is the pharmaceutical composition of embodiment 17, wherein the maximum plasma concentration is between about 2 ng/ml and about 4 ng/ml.

Embodiment 22 is the pharmaceutical composition of embodiment 17, wherein the maximum plasma concentration is about 1 ng/ml to about 4 ng/ml.

Embodiment 23 is the pharmaceutical composition of embodiment 17, wherein the maximum plasma concentration is about 1 ng/ml to about 4 ng/ml.

Embodiment 24 is the pharmaceutical composition of embodiment 17, wherein the maximum plasma concentration is about 1 ng/ml or more upon oral administration to a subject in need thereof.

Embodiment 25 is the pharmaceutical composition of any one of embodiments 17-24, wherein the minimum plasma concentration ($C_{min}$) is between about 0.1 ng/ml and about 0.4 ng/ml.

Embodiment 26 is the pharmaceutical composition of any one of embodiments 17-24, wherein the minimum plasma concentration ($C_{min}$) is between about 0.2 ng/ml and about 0.4 ng/ml.

Embodiment 27 is the pharmaceutical composition of any one of embodiments 17-24, wherein the minimum plasma concentration ($C_{min}$) is at most about 0.4 ng/ml.

Embodiment 28 is the pharmaceutical composition of any one of embodiments 17-27, wherein said composition comprises no more than 5 mg of the 5HT receptor agonist or a pharmaceutically acceptable salt, solvate, metabolite, derivative, or prodrug thereof.

Embodiment 29 is the pharmaceutical composition of any one of embodiments 17-27, wherein said composition comprises no more than 3 mg of the 5HT receptor agonist or a pharmaceutically acceptable salt, solvate, metabolite, derivative, or prodrug thereof.

Embodiment 30 is the pharmaceutical composition of any one of embodiments 17-27, wherein said composition comprises about 5 mg of the 5HT receptor agonist or a pharmaceutically acceptable salt, solvate, metabolite, derivative, or prodrug thereof.

Embodiment 31 is the pharmaceutical composition of any one of embodiments 17-27, wherein said composition comprises about 3 mg of the 5HT receptor agonist or a pharmaceutically acceptable salt, solvate, metabolite, derivative, or prodrug thereof.

Embodiment 32 is the pharmaceutical composition of any one of embodiments 17-31, wherein said composition is formulated to be administered to a subject in need thereof about once a week.

Embodiment 33 is the pharmaceutical composition of any one of embodiments 17-31, wherein said composition is formulated to be administered to a subject in need thereof about once every two weeks.

Embodiment 34 is the pharmaceutical composition of any one of embodiments 17-33, wherein the minimum plasma concentration ($C_{min}$) is determined at a time between 24 and 48 hours after administration.

Embodiment 35 is the pharmaceutical composition of any one of embodiments 17-33, wherein the minimum plasma concentration ($C_{min}$) is determined at a time between 48 and 72 hours after administration.

Embodiment 36 is the pharmaceutical composition of any one of embodiments 17-33, wherein the minimum plasma concentration ($C_{min}$) is determined at a time between 72 and 96 hours after administration.

Embodiment 37 is the pharmaceutical composition of any one of embodiments 17-33, wherein the minimum plasma concentration ($C_{min}$) is determined at a time between 96 to 120 hours after administration.

Embodiment 38 is the pharmaceutical composition of any one of embodiments 17-33, wherein said composition provides the minimum plasma concentration ($C_{min}$) is determined at a time between 120 to 144 hours after administration.

Embodiment 39 is the pharmaceutical composition of any one of embodiments 1-38, wherein the composition comprises an oral dosage form, the oral dosage form comprising a (e.g. immediate-release or controlled release) layer or coating and a controlled release core, the layer or coating comprising (i) one or more 5HT receptor agonist or a pharmaceutically acceptable salt, solvate, metabolite, derivative, or prodrug thereof and, optionally, (ii) one or more second agent, the one or more second agent being a stimulant, an antihistamine, an antiemetic, an antidepressant, an anti-inflammatory, a growth factor, a lithium compound, resveratrol, phosphatidylcholine, curcumin, magnesium, melatonin, pregnenolone, ginseng, tryptophan, or lysergic acid diethylamide, or a 5HT receptor antagonist, or any combination thereof; and the controlled release core comprising:

a) one or more 5HT receptor agonist or a pharmaceutically acceptable salt, solvate, metabolite, derivative, or prodrug thereof;
b) at least one pharmaceutically acceptable excipient;
c) optionally one or more agents selected from the group consisting of surfactants, preservatives, flavoring agents, sweetening agents, and antifoaming agents-; and
d) optionally one or more agents selected from the group consisting of stimulants, antihistamines, antiemetics, antidepressants, anti-inflammatories, growth factors, lithium compounds, resveratrol, phosphatidylcholine, curcumin, magnesium, melatonin, pregnenolone, ginseng, tryptophan, lysergic acid diethylamide, or a 5HT receptor antagonist, and any combination of one or more thereof.

Embodiment 40 is the pharmaceutical composition of any one of embodiments 1-38, wherein the composition comprises an oral dosage form, the oral dosage form comprising a (e.g. immediate-release or controlled release) layer or coating and a controlled release core, the layer or coating comprising (i) one or more 5HT receptor agonist or a pharmaceutically acceptable salt, solvate, metabolite, derivative, or prodrug thereof and, optionally, (ii) one or more second agent, the one or more second agent being a stimulant, an antihistamine, an antiemetic, an antidepressant, an anti-inflammatory, a growth factor, a lithium compound, resveratrol, phosphatidylcholine, curcumin, magnesium, melatonin, pregnenolone, ginseng, tryptophan, lysergic acid diethylamide, or a 5HT receptor antagonist; and the controlled release core comprising:

a) one or more 5HT receptor agonist or a pharmaceutically acceptable salt, solvate, metabolite, derivative, or prodrug thereof (e.g. and one or more additional active core agent, such as a stimulant, an antihistamine, an antiemetic, an antidepressant, an anti-inflammatory, a growth factor, a lithium compound, resveratrol, phosphatidylcholine, curcumin, magnesium, melatonin, pregnenolone, ginseng, tryptophan, lysergic acid diethylamide, a 5HT receptor antagonist, or any combination thereof);
b) a buffer;
c) water; and
d) optionally one or more agents selected from the group consisting of preservatives, flavoring agents, sweetening agents, surfactants, antifoaming agents, and suspension aids.

Embodiment 41 is the pharmaceutical composition of embodiment 39 or 40, wherein the immediate-release layer comprises at least about 1 mg of the 5HT receptor agonist or a pharmaceutically acceptable salt, solvate, metabolite, derivative, or prodrug thereof.

Embodiment 42 is the pharmaceutical composition of embodiment 39 or 40, wherein the immediate-release layer comprises at most about 50 mg of the 5HT receptor agonist or a pharmaceutically acceptable salt, solvate, metabolite, derivative, or prodrug thereof.

Embodiment 43 is the pharmaceutical composition of embodiment 39 or 40, wherein the immediate-release layer comprises from about 1 mg to about 50 mg of the 5HT receptor agonist or a pharmaceutically acceptable salt, solvate, metabolite, derivative, or prodrug thereof.

Embodiment 44 is the pharmaceutical composition of embodiment 39 or 40, wherein the immediate-release layer comprises from about 2 mg to about 40 mg of the 5HT receptor agonist or a pharmaceutically acceptable salt, solvate, metabolite, derivative, or prodrug thereof.

Embodiment 45 is the pharmaceutical composition of embodiment 39 or 40, wherein the immediate-release layer comprises from about 3 mg to about 30 mg of the 5HT receptor agonist or a pharmaceutically acceptable salt, solvate, metabolite, derivative, or prodrug thereof.

Embodiment 46 is the pharmaceutical composition of embodiment 39 or 40, wherein the immediate-release layer comprises from about 5 mg to about 20 mg of the 5HT receptor agonist or a pharmaceutically acceptable salt, solvate, metabolite, derivative, or prodrug thereof.

Embodiment 47 is the pharmaceutical composition of embodiment 39 or 40, wherein the immediate-release layer comprises from about 1 mg to about 10 mg of the 5HT receptor agonist or a pharmaceutically acceptable salt, solvate, metabolite, derivative, or prodrug thereof.

Embodiment 48 is the pharmaceutical composition of embodiment 39 or 40, wherein the immediate-release layer comprises about 1 mg, about 2 mg, about 3 mg, about 4 mg, about 5 mg, about 6 mg, about 7 mg, about 8 mg, about 9 mg, or about 10 mg of the 5HT receptor agonist or a pharmaceutically acceptable salt, solvate, metabolite, derivative, or prodrug thereof.

Embodiment 49 is the pharmaceutical composition of any one of embodiments 39-48, wherein the controlled release core comprises at least about 10 mg of the 5HT receptor agonist or a pharmaceutically acceptable salt, solvate, metabolite, derivative, or prodrug thereof.

Embodiment 50 is the pharmaceutical composition of any one of embodiments 39-48, wherein the controlled release core comprises at most about 300 mg of the 5HT receptor agonist or a pharmaceutically acceptable salt, solvate, metabolite, derivative, or prodrug thereof.

Embodiment 51 is the pharmaceutical composition of any one of embodiments 39-48, wherein the controlled release core comprises from about 10 mg to about 300 mg of the 5HT receptor agonist or a pharmaceutically acceptable salt, solvate, metabolite, derivative, or prodrug thereof.

Embodiment 52 is the pharmaceutical composition of any one of embodiments 39-48, wherein the controlled release core comprises from about 15 mg to about 250 mg of the 5HT receptor agonist or a pharmaceutically acceptable salt, solvate, metabolite, derivative, or prodrug thereof.

Embodiment 53 is the pharmaceutical composition of any one of embodiments 39-48, wherein the controlled release core comprises from about 20 mg to about 200 mg of the 5HT receptor agonist or a pharmaceutically acceptable salt, solvate, metabolite, derivative, or prodrug thereof.

Embodiment 54 is the pharmaceutical composition of any one of embodiments 39-48, wherein the controlled release core comprises from about 30 mg to about 150 mg of the 5HT receptor agonist or a pharmaceutically acceptable salt, solvate, metabolite, derivative, or prodrug thereof.

Embodiment 55 is the pharmaceutical composition of any one of embodiments 39-48, wherein the controlled release core comprises from about 40 mg to about 100 mg of the 5HT receptor agonist or a pharmaceutically acceptable salt, solvate, metabolite, derivative, or prodrug thereof.

Embodiment 56 is the pharmaceutical composition of any one of embodiments 39-48, wherein the controlled release core comprises from about 10 mg to about 50 mg of the 5HT receptor agonist or a pharmaceutically acceptable salt, solvate, metabolite, derivative, or prodrug thereof.

Embodiment 57 is the pharmaceutical composition of any one of embodiments 39-48, wherein the controlled release core comprises from about 10 mg to about 30 mg of the 5HT receptor agonist or a pharmaceutically acceptable salt, solvate, metabolite, derivative, or prodrug thereof.

Embodiment 58 is the pharmaceutical composition of any one of embodiments 39-48, wherein the controlled release core comprises about 10 mg, about 15 mg, about 20 mg, about 25 mg, about 30 mg, about 35 mg, about 40 mg, about 45 mg, or about 50 mg of the 5HT receptor agonist or a pharmaceutically acceptable salt, solvate, metabolite, derivative, or prodrug thereof.

Embodiment 59 is the pharmaceutical composition of any one of the preceding embodiments, wherein the pharmaceutically acceptable excipient is selected from the group consisting of fillers, binders, suspending agents, disintegrants, lubricants, and combinations thereof.

Embodiment 60 is the pharmaceutical composition of embodiment 59, wherein said composition comprises a filler.

Embodiment 61 is the pharmaceutical composition of embodiment 60, wherein the amount of the filler is from about 10% to about 20% by total weight of the composition.

Embodiment 62 is the pharmaceutical composition of embodiment 59, wherein said composition comprises a binder.

Embodiment 63 is the pharmaceutical composition of embodiment 62, wherein the amount of the binder is from about 5% to about 15% by total weight of the composition.

Embodiment 64 is the pharmaceutical composition of embodiment 59, wherein said composition comprises a suspending agent.

Embodiment 65 is the pharmaceutical composition of embodiment 64, wherein the amount of the suspending agent is from about 1% to about 5% by total weight of the composition.

Embodiment 66 is the pharmaceutical composition of embodiment 59, wherein said composition comprises a disintegrant.

Embodiment 67 is the pharmaceutical composition of embodiment 66, wherein the amount of the disintegrant is from about 1% to about 5% by total weight of the composition.

Embodiment 68 is the pharmaceutical composition of embodiment 59, wherein said composition comprises a lubricant.

Embodiment 69 is the pharmaceutical composition of embodiment 68, wherein the amount of the lubricant is from about 1% to about 5% by total weight of the composition.

Embodiment 70 is the pharmaceutical composition of any one of embodiments 39-69, wherein said composition additionally comprises a surfactant.

Embodiment 71 is the pharmaceutical composition of embodiment 70, wherein the amount of the surfactant is from about 0.1% to about 2% by total weight of the composition.

Embodiment 72 is the pharmaceutical composition of embodiment 70, wherein the amount of the surfactant is from about 1% to about 15% by total weight of the composition.

Embodiment 73 is the pharmaceutical composition of any one of embodiments 39-72, wherein said composition is a tablet or capsule.

Embodiment 74 is the pharmaceutical composition of embodiment 73, wherein said composition is a capsule.

Embodiment 75 is the pharmaceutical composition of embodiment 73, wherein said composition is a tablet.

Embodiment 76 is the pharmaceutical composition of any one of embodiments 39-75, wherein said composition additionally comprises a preservative.

Embodiment 77 is the pharmaceutical composition of embodiment 76, wherein the amount of preservative is about 0.1% to about 2% by total weight of the composition.

Embodiment 78 is the pharmaceutical composition of any one of embodiments 39-77, wherein said composition additionally comprises an antifoaming agent.

Embodiment 79 is the pharmaceutical composition of embodiment 78, wherein the amount of the antifoaming agent is about 0.1% to about 1% by total weight of the composition.

Embodiment 80 is the pharmaceutical composition of any one of embodiments 39-79, wherein said composition comprises a flavoring agent.

Embodiment 81 is the pharmaceutical composition of any one of embodiments 39-80, wherein said composition comprises a sweetener.

Embodiment 82 is the pharmaceutical composition of embodiment 39-81, wherein said composition is formulated and/or packaged to be repeatedly administered to a subject in need thereof about once a week (or more frequently, such as two or three times a week, daily, or the like).

Embodiment 83 is the pharmaceutical composition of embodiment 39-81, wherein said composition is formulated and/or packaged to be repeatedly administered to a subject in need thereof about once every two weeks (or less frequently).

Embodiment 84 is the pharmaceutical composition of embodiment 39-81, wherein said composition is repeatedly administered to a subject in need thereof about once a month.

Embodiment 85 is the pharmaceutical composition of any one of embodiments 1-38, wherein the composition comprises a buccal composition comprising:

(a) a 5HT receptor agonist or a pharmaceutically acceptable salt, solvate, metabolite, derivative, or prodrug thereof; and (b) a matrix which releases the 5HT receptor agonist or a pharmaceutically acceptable salt, solvate, metabolite, derivative, or prodrug thereof at a predetermined rate for transport across buccal membranes, wherein the matrix comprises one or more compounds selected from:

(i) taste masking agents, (ii) enhancers, (iii) complexing agents, and mixtures thereof; and (c) one or more of pharmaceutically acceptable excipients.

Embodiment 86 is the pharmaceutical composition of embodiment 85, wherein the composition comprises at least about 10 mg of the 5HT receptor agonist or a pharmaceutically acceptable salt, solvate, metabolite, derivative, or prodrug thereof.

Embodiment 87 is the pharmaceutical composition of embodiment 85, wherein the composition comprises at most about 300 mg of the 5HT receptor agonist or a pharmaceutically acceptable salt, solvate, metabolite, derivative, or prodrug thereof.

Embodiment 88 is the pharmaceutical composition of embodiment 85, wherein the composition comprises from about 10 mg to about 300 mg of the 5HT receptor agonist or a pharmaceutically acceptable salt, solvate, metabolite, derivative, or prodrug thereof.

Embodiment 89 is the pharmaceutical composition of embodiment 85, wherein the composition comprises from about 15 mg to about 250 mg of the 5HT receptor agonist or a pharmaceutically acceptable salt, solvate, metabolite, derivative, or prodrug thereof.

Embodiment 90 is the pharmaceutical composition of embodiment 85, wherein the composition comprises from about 20 mg to about 200 mg of the 5HT receptor agonist or a pharmaceutically acceptable salt, solvate, metabolite, derivative, or prodrug thereof.

Embodiment 91 is the pharmaceutical composition of embodiment 85, wherein the composition comprises from about 30 mg to about 150 mg of the 5HT receptor agonist or a pharmaceutically acceptable salt, solvate, metabolite, derivative, or prodrug thereof.

Embodiment 92 is the pharmaceutical composition of embodiment 85, wherein the composition comprises from about 40 mg to about 100 mg of the 5HT receptor agonist or a pharmaceutically acceptable salt, solvate, metabolite, derivative, or prodrug thereof.

Embodiment 93 is the pharmaceutical composition of embodiment 85, wherein the composition comprises from about 10 mg to about 50 mg of the 5HT receptor agonist or a pharmaceutically acceptable salt, solvate, metabolite, derivative, or prodrug thereof.

Embodiment 94 is the pharmaceutical composition of embodiment 85, wherein the composition comprises from about 10 mg to about 30 mg of the 5HT receptor agonist or a pharmaceutically acceptable salt, solvate, metabolite, derivative, or prodrug thereof.

Embodiment 95 is the pharmaceutical composition of embodiment 85, wherein the composition comprises about 10 mg, about 15 mg, about 20 mg, about 25 mg, about 30 mg, about 35 mg, about 40 mg, about 45 mg, or about 50 mg of the 5HT receptor agonist or a pharmaceutically acceptable salt, solvate, metabolite, derivative, or prodrug thereof.

Embodiment 96 is the pharmaceutical composition of any one of embodiments 85-95, wherein the enhancer is selected from the group consisting of surfactants, bile salts, bile salt derivatives, fatty acids, fatty acid derivatives, sulfoxides, chelators, alcohols, polyols, and polymers.

Embodiment 97 is the pharmaceutical composition of any one of embodiments 1-38, wherein the composition comprises a dosage form for nasal administration comprising:

(a) a therapeutically effective amount of a 5HT receptor agonist or a pharmaceutically acceptable salt, solvate, metabolite, derivative, or prodrug thereof;

(b) permeation enhancer, and (c) one or more of pharmaceutically acceptable excipients.

Embodiment 98 is the pharmaceutical composition of embodiment 97, wherein the dosage form comprises at most about 5 mg of the 5HT receptor agonist or a pharmaceutically acceptable salt, solvate, metabolite, derivative, or prodrug thereof.

Embodiment 99 is the pharmaceutical composition of embodiment 97, wherein the dosage form comprises at least about 0.5 mg of the 5HT receptor agonist or a pharmaceutically acceptable salt, solvate, metabolite, derivative, or prodrug thereof.

Embodiment 100 is the pharmaceutical composition of embodiment 97, wherein the dosage form comprises from about 0.5 mg to about 2 mg of the 5HT receptor agonist or a pharmaceutically acceptable salt, solvate, metabolite, derivative, or prodrug thereof.

Embodiment 101 is the pharmaceutical composition of embodiment 97, wherein the dosage form comprises from about 0.5 mg to about 5 mg of the 5HT receptor agonist or a pharmaceutically acceptable salt, solvate, metabolite, derivative, or prodrug thereof.

Embodiment 102 is the pharmaceutical composition of embodiment 97, wherein the dosage form comprises from about 1 mg to about 4 mg of the 5HT receptor agonist or a pharmaceutically acceptable salt, solvate, metabolite, derivative, or prodrug thereof.

Embodiment 103 is the pharmaceutical composition of embodiment 97, wherein the dosage form comprises from about 2 mg to about 3 mg of the 5HT receptor agonist or a pharmaceutically acceptable salt, solvate, metabolite, derivative, or prodrug thereof.

Embodiment 104 is the pharmaceutical composition of embodiment 97, wherein the dosage form comprises about 0.5 mg, about 1 mg, about 1.5 mg, about 2 mg, about 2.5 mg, about 3 mg, about 3.5 mg, about 4 mg, about 4.5 mg, or about 5 mg of the 5HT receptor agonist or a pharmaceutically acceptable salt, solvate, metabolite, derivative, or prodrug thereof.

Embodiment 105 is the pharmaceutical composition of any one of embodiments 97-104, wherein the permeation enhancer is selected from the group consisting of bile salts, surfactants, fatty acids, fatty acid derivatives, glycerides, chelators, salicylates, and polymers.

Embodiment 106 is the pharmaceutical composition of any one of embodiments 97-105, wherein the pharmaceutically acceptable excipient is selected from the group consisting of fillers, binders, suspending agents, disintegrants, lubricants, and combinations thereof.

Embodiment 107 is the pharmaceutical composition of any one of embodiments 1-38, wherein the composition comprises a patch comprising (i) a support layer and (ii) an adhesive agent layer, wherein the adhesive agent layer comprises (a) a 5HT receptor agonist or a pharmaceutically acceptable salt, solvate, metabolite, derivative, or prodrug thereof, and (b) a rubber-based adhesive agent and/or a silicone-based adhesive agent.

Embodiment 108 is the pharmaceutical composition of any one of the preceding embodiments, wherein the 5HT receptor agonist is a 5HT2 receptor agonist.

Embodiment 109 is the pharmaceutical composition of embodiment 108, wherein the 5HT2 receptor agonist is one or more of a 5HT2A receptor agonist, a 5HT2B receptor agonist and a 5HT2C receptor agonist.

Embodiment 110 is the pharmaceutical composition of embodiment 108, wherein the 5HT2 receptor agonist is a 5HT2A receptor agonist or a 5HT2C receptor agonist.

Embodiment 111 is the pharmaceutical composition of embodiment 108, wherein the 5HT2 receptor agonist is a 5HT2A receptor agonist and a 5HT2C receptor agonist.

Embodiment 112 is the pharmaceutical composition of any one of the preceding embodiments, wherein the 5HT receptor agonist is psilocin or a pharmaceutically acceptable salt, solvate, metabolite, derivative, or prodrug thereof.

Embodiment 113 is the pharmaceutical composition of any one of the preceding embodiments, wherein the 5HT receptor agonist is psilocybin or a pharmaceutically acceptable salt, solvate, metabolite, derivative, or prodrug thereof.

Embodiment 114 is a pharmaceutical composition comprising:

a) a therapeutically effective amount of one or more 5HT receptor agonist or a pharmaceutically acceptable salt, solvate, metabolite, derivative, or prodrug thereof, b) a pharmaceutically acceptable excipient, and c) optionally one or more agents selected from the group consisting of surfactants, preservatives, flavoring agents, sweetening agents, and antifoaming agents;

wherein the pharmaceutical composition is a low-dose pharmaceutical composition;

wherein following administration to an individual in need thereof, the pharmaceutical composition provides a maximum plasma concentration ($C_{max}$) of the 5HT receptor agonist or a pharmaceutically acceptable salt, solvate, metabolite, derivative, or prodrug thereof of less than 6 ng/mL in the individual in need thereof; and wherein the 5HT receptor agonist is psilocin or a pharmaceutically acceptable salt, solvate, metabolite, derivative, or prodrug thereof; or wherein the 5HT receptor agonist is psilocybin or a pharmaceutically acceptable salt, solvate, metabolite, derivative, or prodrug thereof.

Embodiment 115 is a pharmaceutical composition comprising an oral dosage form, the oral dosage form comprising an immediate-release top layer and a controlled release core, the immediate-release layer comprising (i) one or more 5HT receptor agonist or a pharmaceutically acceptable salt, solvate, metabolite, derivative, or prodrug thereof and (ii) one or more second agent, the one or more second agent being a stimulant, an antihistamine, an antiemetic, an antidepressant, an anti-inflammatory, a growth factor, a lithium compound, resveratrol, phosphatidylcholine, curcumin, magnesium, melatonin, pregnenolone, ginseng, or lysergic acid diethylamide; and the controlled release core comprising:

a) one or more 5HT receptor agonist or a pharmaceutically acceptable salt, solvate, metabolite, derivative, or prodrug thereof;

b) at least one pharmaceutically acceptable excipient; and c) optionally one or more agents selected from the group consisting of surfactants, preservatives, flavoring agents, sweetening agents, and antifoaming agents;

wherein the pharmaceutical composition is a low-dose pharmaceutical composition; and wherein following administration to an individual in need thereof, the pharmaceutical composition provides a maximum plasma concentration ($C_{max}$) of the 5HT receptor agonist or a pharmaceutically acceptable salt, solvate, metabolite, derivative, or prodrug thereof of less than 6 ng/ml in the individual in need thereof.

Embodiment 116 is the pharmaceutical composition of embodiment 115, wherein the 5HT receptor agonist is psilocin or a pharmaceutically acceptable salt, solvate, metabolite, derivative, or prodrug thereof.

Embodiment 117 is the pharmaceutical composition of embodiment 115, wherein the 5HT receptor agonist is psilocybin or a pharmaceutically acceptable salt, solvate, metabolite, derivative, or prodrug thereof.

What is claimed is:

1. A method of improving motivation or cognitive engagement in a subject in need thereof, the method comprising orally administering to the subject a pharmaceutical composition comprising:

(a) a therapeutically effective and non-hallucinogenic amount of psilocybin, wherein the psilocybin is in an amount of 0.5 mg to 4.5 mg; and (b) a pharmaceutically acceptable inert excipient; wherein the psilocybin is the only active agent, wherein the therapeutically effective and non-hallucinogenic amount of the psilocybin is provided to the subject in need thereof in an amount insufficient to provide a hallucinogenic experience, and wherein the subject is an adult human and the psilocybin improves motivation or cognitive engagement in the subject without the need for constant supervision by a healthcare worker.

2. The method of claim 1, wherein the pharmaceutical composition is not administered as a placebo.

3. The method of claim 1, wherein the psilocybin is deuterated.

4. The method of claim 1, wherein the therapeutically effective and non-hallucinogenic amount of the psilocybin is 1.5 mg to 4.5 mg.

5. The method of claim 1, wherein the therapeutically effective and non-hallucinogenic amount of the psilocybin is 1 mg to 4 mg.

* * * * *